US012668828B2

(12) United States Patent
Idelson

(10) Patent No.: US 12,668,828 B2
(45) Date of Patent: *Jun. 30, 2026

(54) PROKARYOTIC EXPRESSION SYSTEM AND METHODS OF USING THE SAME

(71) Applicant: SEEVIX MATERIAL SCIENCES LTD., Jerusalem (IL)

(72) Inventor: Gregory Idelson, Maale Adumim (IL)

(73) Assignee: SEEVIX MATERIAL SCIENCES LTD., Jerusalem (IL)

( * ) Notice: Subject to any disclaimer, the term of this patent is extended or adjusted under 35 U.S.C. 154(b) by 1120 days.

This patent is subject to a terminal disclaimer.

(21) Appl. No.: 17/624,670

(22) PCT Filed: Jul. 5, 2020

(86) PCT No.: PCT/IL2020/050752
§ 371 (c)(1),
(2) Date: Jan. 4, 2022

(87) PCT Pub. No.: WO2021/001840
PCT Pub. Date: Jan. 7, 2021

(65) Prior Publication Data
US 2022/0275418 A1     Sep. 1, 2022

Related U.S. Application Data

(60) Provisional application No. 62/870,750, filed on Jul. 4, 2019.

(51) Int. Cl.
*C12P 21/02* (2006.01)
*C07K 14/435* (2006.01)
*C12N 1/20* (2006.01)
*C12N 15/70* (2006.01)

(52) U.S. Cl.
CPC ........ *C12P 21/02* (2013.01); *C07K 14/43518* (2013.01); *C12N 1/20* (2013.01); *C12N 15/70* (2013.01); *C12N 2800/101* (2013.01)

(58) Field of Classification Search
None
See application file for complete search history.

(56) References Cited

U.S. PATENT DOCUMENTS

| | | | |
|---|---|---|---|
| 3,755,560 A | 8/1973 | Dickert et al. | |
| 4,421,769 A | 12/1983 | Dixon et al. | |
| 5,011,681 A | 4/1991 | Ciotti et al. | |
| 7,057,023 B2 | 6/2006 | Islam et al. | |
| 7,521,228 B2 | 4/2009 | Lewis et al. | |
| 7,674,882 B2 | 3/2010 | Kaplan et al. | |
| 7,754,851 B2 | 7/2010 | Scheibel et al. | |
| 8,030,024 B2 | 10/2011 | Scheibel et al. | |
| 8,222,479 B2 | 7/2012 | Zhao et al. | |
| 8,461,301 B2 | 6/2013 | Gat et al. | |
| 8,642,734 B2 | 2/2014 | Johansson | |
| 9,233,067 B2 | 1/2016 | Lammel et al. | |
| 9,475,852 B2 | 10/2016 | Bogush et al. | |
| 9,993,525 B2 | 6/2018 | Nazhat et al. | |
| 10,253,213 B2 | 4/2019 | Leimer et al. | |
| 10,981,959 B2 * | 4/2021 | Ittah ...................... | C12N 15/86 |
| 11,142,553 B2 | 10/2021 | Taniike et al. | |
| 11,376,329 B2 | 7/2022 | Kluge et al. | |
| 2005/0054830 A1 | 3/2005 | Islam et al. | |
| 2007/0113355 A1 | 5/2007 | Knight | |
| 2007/0196429 A1 | 8/2007 | Scheibel et al. | |
| 2009/0232963 A1 | 9/2009 | Kaplan et al. | |
| 2010/0143487 A1 | 6/2010 | Masters | |
| 2010/0317587 A1 | 12/2010 | Chung et al. | |
| 2011/0020409 A1 | 1/2011 | Altman et al. | |
| 2011/0189292 A1 | 8/2011 | Lebreton et al. | |
| 2012/0022005 A1 | 1/2012 | Gat et al. | |
| 2013/0109762 A1 | 5/2013 | Lammel | |
| 2014/0315828 A1 | 10/2014 | Pavlovic et al. | |
| 2015/0056256 A1 | 2/2015 | Essaidi | |
| 2015/0087046 A1 | 3/2015 | Hedhammar | |
| 2015/0165092 A1 | 6/2015 | Kaplan et al. | |
| 2015/0284565 A1 | 10/2015 | Scheibel et al. | |
| 2015/0376247 A1 | 12/2015 | Osawa et al. | |
| 2016/0046679 A1 | 2/2016 | Kluge et al. | |
| 2016/0298265 A1 | 10/2016 | Lewis et al. | |
| 2019/0002510 A1 | 1/2019 | Ittah et al. | |
| 2019/0040110 A1 | 2/2019 | Ittah et al. | |
| 2020/0270316 A1 | 8/2020 | Römer et al. | |
| 2021/0101946 A1 | 4/2021 | Lo et al. | |
| 2021/0138071 A1 | 5/2021 | Santos et al. | |

(Continued)

FOREIGN PATENT DOCUMENTS

| | | |
|---|---|---|
| CA | 3014537 A1 | 8/2017 |
| CN | 101133080 A | 2/2008 |

(Continued)

OTHER PUBLICATIONS

Heidebrecht et al., "Biomimetic Fibers Made of Recombinant Spidroins with the Same Toughness as Natural Spider Silk", Advanced Materials, 27: 2189-2194 (Year: 2015).*

Lammel AS, Hu X, Park SH, Kaplan DL, Scheibel TR. Controlling silk fibroin particle features for drug delivery. Biomaterials. Jun. 2010;31(16):4583-91. doi: 10.1016/j.biomaterials.2010.02.024. Epub Mar. 9, 2010. PMID: 20219241; PMCID: PMC2846964.

Huemmerich D, Helsen CW, Quedzuweit S, Oschmann J, Rudolph R, Scheibel T. Primary structure elements of spider dragline silks and their contribution to protein solubility. Biochemistry. Oct. 26, 2004;43(42):13604-12. doi: 10.1021/bi048983q. PMID: 15491167.

(Continued)

*Primary Examiner* — Anand U Desai

(74) *Attorney, Agent, or Firm* — The Roy Gross Law Firm, LLC; Roy D. Gross

(57)     ABSTRACT

A recombinant bacterium having the ability to/express MaSP-based proteins, nucleic acids encoding same and method for the preparation of synthetic dragline spider silk are provided.

18 Claims, 35 Drawing Sheets

Specification includes a Sequence Listing.

(56) References Cited

U.S. PATENT DOCUMENTS

| | | | |
|---|---|---|---|
| 2021/0155812 A1 | 5/2021 | Omenetto et al. |
| 2021/0401685 A1 | 12/2021 | Martínez Rovira et al. |
| 2022/0062335 A1 | 3/2022 | Tennican |
| 2022/0127768 A1 | 4/2022 | Yoshioka et al. |
| 2022/0177530 A1 | 6/2022 | Altman |
| 2022/0235099 A1 | 7/2022 | Kamikubo et al. |
| 2023/0042322 A1 | 2/2023 | Ittah et al. |

FOREIGN PATENT DOCUMENTS

| | | | |
|---|---|---|---|
| CN | 101395178 A | 3/2009 |
| CN | 102475909 A | 5/2012 |
| CN | 101253193 B | 11/2012 |
| CN | 101018806 B | 5/2014 |
| CN | 107595661 A | 1/2018 |
| CN | 109477252 A | 3/2019 |
| CN | 111214385 A | 6/2020 |
| EP | 1609801 A1 | 12/2005 |
| EP | 1773875 B1 | 9/2014 |
| EP | 1558444 B1 | 9/2016 |
| JP | 2002369878 A | 12/2002 |
| JP | 2008507260 A | 3/2008 |
| JP | 2009505668 A | 2/2009 |
| JP | 2011504374 A | 2/2011 |
| JP | 2012531889 A | 12/2012 |
| JP | 2013512265 A | 4/2013 |
| JP | 2015532690 A | 11/2015 |
| JP | 2018531040 A | 10/2018 |
| JP | 2019510541 A | 4/2019 |
| JP | WO2019082935 A1 | 1/2021 |
| JP | 2021054819 A | 4/2021 |
| JP | 2021155361 A | 10/2021 |
| TW | I290930 B | 12/2007 |
| WO | 2004090205 A2 | 10/2004 |
| WO | 2006002827 A1 | 1/2006 |
| WO | 2006002843 A1 | 1/2006 |
| WO | 2006002853 A1 | 1/2006 |
| WO | 2006008163 A2 | 1/2006 |
| WO | 2007025719 A1 | 3/2007 |
| WO | 2007078239 A3 | 12/2007 |
| WO | 2011063990 A2 † | 6/2011 |
| WO | 2011069643 A2 | 6/2011 |
| WO | 2011113592 A1 | 9/2011 |
| WO | 2012175153 A2 | 12/2012 |
| WO | 2013071107 A1 † | 5/2013 |
| WO | 2014037453 A1 | 3/2014 |
| WO | 2016038387 A1 | 3/2016 |
| WO | 2016057851 A1 | 4/2016 |
| WO | 2017025964 A1 | 2/2017 |
| WO | 2017138002 A1 | 8/2017 |
| WO | 2019067737 A1 | 4/2019 |
| WO | 2020014595 A1 | 1/2020 |
| WO | 2020183465 A1 | 9/2020 |
| WO | 2021001840 A1 | 1/2021 |
| WO | 2021011431 A1 | 1/2021 |
| WO | 2021121647 A1 | 6/2021 |
| WO | 2021214780 A1 | 10/2021 |
| WO | 2022020212 A2 | 1/2022 |

OTHER PUBLICATIONS

Yang, Yan-Xiang & Qian, Zhi-Gang & Zhong, Jian-Jiang & Xia, Xiao-Xia. (2016). Hyper-production of large proteins of spider dragline silk MaSp2 by *Escherichia coli* via synthetic biology approach. Process Biochemistry. 51. 10.1016/j.procbio.2016.01.006.

Ittah S, Barak N, Gat U. A proposed model for dragline spider silk self-assembly: insights from the effect of the repetitive domain size on fiber properties. Biopolymers. May 2010;93(5):458-68. doi: 10.1002/bip.21362. PMID: 20014164.

Ittah S, Michaeli A, Goldblum A, Gat U. A model for the structure of the C-terminal domain of dragline spider silk and the role of its conserved cysteine. Biomacromolecules. Sep. 2007;8(9):2768-73. doi: 10.1021/bm7004559. Epub Aug. 14, 2007. PMID: 17696395.

Ittah S, Cohen S, Garty S, Cohn D, Gat U. An essential role for the C-terminal domain of a dragline spider silk protein in directing fiber formation. Biomacromolecules. Jun. 2006;7(6):1790-5. doi: 10.1021/bm060120k. PMID: 16768399.

Huemmerich D, Scheibel T, Vollrath F, Cohen S, Gat U, Ittah S. Novel assembly properties of recombinant spider dragline silk proteins. Curr Biol. Nov. 23, 2004;14(22):2070-4. doi: 10.1016/j.cub.2004.11.005. PMID: 15556872.

Gatesy J, Hayashi C, Motriuk D, Woods J, Lewis R. Extreme diversity, conservation, and convergence of spider silk fibroin sequences. Science. Mar. 30, 2001;291(5513):2603-5. doi: 10.1126/science. 1057561. PMID: 11283372.

An B, Tang-Schomer M, Huang W, He J, Jones J, Lewis RV, Kaplan DL. Physical and biological regulation of neuron regenerative growth and network formation on recombinant dragline silks. Biomaterials. Apr. 2015;48:137-146. doi: 10.1016/j.biomaterials.2015.01.044. Epub Feb. 11, 2015. PMID: 25701039; PMCID: PMC4353650.

https://www.bioinformatics.org/sms/prot_mw.html, The Sequence Manipulation Suite: Protein Molecular Weight, accessed on Dec. 2, 2019.

Rising A, Widhe M, Johansson J, Hedhammar M. Spider silk proteins: recent advances in recombinant production, structure-function relationships and biomedical applications. Cell Mol Life Sci. Jan. 2011;68(2):169-84. doi: 10.1007/ s00018-010-0462-z. Epub Jul. 29, 2010. PMID: 20668909.

Lewicka M, Hermanson O, Rising AU. Recombinant spider silk matrices for neural stem cell cultures. Biomaterials. Nov. 2012;33(31):7712-7. doi: 10.1016/j.biomaterials.2012.07.021. Epub Aug. 3, 2012. PMID: 22863380.

Knight E, Przyborski S. Advances in 3D cell culture technologies enabling tissue-like structures to be created in vitro. J Anat. Dec. 2015;227(6):746-56. doi: 10.1111/joa.12257. Epub Nov. 20, 2014. PMID: 25411113; PMCID: PMC4694114.

B. Liebmann, D. Hümmerich, T. Scheibel, M. Fehr, Formulation of poorly water-soluble substances using self-assembling spider silk protein, Colloids and Surfaces A: Physicochemical and Engineering Aspects, vol. 331, Issues 1-2, 2008, pp. 126-132, ISSN 0927-7757, https://doi.org/10.1016/j.colsurfa.2008.04.005.

Murphy AR, Kaplan DL. Biomedical applications of chemically-modified silk fibroin. J Mater Chem. Jun. 23, 2009;19(36):6443-6450. doi: 10.1039/b905802h. PMID: 20161439; PMCID: PMC2790051.

Hardy JG, Bertin A, Torres-Rendon JG, Leal-Egana A, Humenik M, Bauer F, Walther A, Colfen H, Schlaad H, Scheibel TR. Facile Photochemical Modification of Silk Protein-Based Biomaterials. Macromol Biosci. Nov. 2018;18(11):e1800216. doi: 10.1002/mabi.201800216. Epub Sep. 19, 2018. PMID: 30230222.

Chen, J., Venkatesan, H. and Hu, J. (2018), Chemically Modified Silk Proteins. Adv. Eng. Mater., 20: 1700961. https://doi.org/10.1002/adem.201700961.

Doblhofer E, Heidebrecht A, Scheibel T. To spin or not to spin: spider silk fibers and more. Appl Microbiol Biotechnol. Nov. 2015;99(22):9361-80. doi: 10.1007/s00253-015-6948-8. Epub Sep. 11, 2015. PMID: 26362683.

Sequence—Reference Material 1—Cited in a Third Party Observation in Japan, Oct. 2021.

Sequence—Reference Material 2—Cited in a Third Party Observation in Japan, Oct. 2021.

Sequence—Reference Material 3—Cited in a Third Party Observation in Japan, Oct. 2021.

PCT International Search Report for International Application No. PCT/IL2020/050752, mailed Sep. 21, 2020, 6pp.

PCT Written Opinion for International Application No. PCT/IL2020/050752, mailed Sep. 21, 2020, 5pp.

PCT International Preliminary Report on Patentability for International Application No. PCT/IL2020/050752, issued Dec. 28, 2021, 6pp.

Huemmerich et al., Primary Structure Elements of Spider Dragline Silks and Their Contribution to Protein Solubility, Biochemistry 2004, 43, 42, 13604-13612, 2004. https://doi.org/10.1021/bi048983q.

(56) References Cited

OTHER PUBLICATIONS

Lammel et al, Controlling silk fibroin particle features for drug delivery, Biomaterials, vol. 31, Issue 16, 2010, pp. 4583-4591, ISSN 0142-9612. DOI: 10.1016/j.biomaterials.2010.02.024.

Stothard, P. Protein Molecular Weight. Protein molecular weight. [www.bioinformatics.org/sms/prot_mw.html], 2022.

Scheibel, Spider silks: recombinant synthesis, assembly, spinning, and engineering of synthetic proteins. Microb Cell Fact 3, 14 (2004), https://doi.org/10.1186/1475-2859-3-14.

Ayoub et al. Blueprint for a High-Performance Biomaterial: Full-Length Spider Dragline Silk Genes, PLoS One, Jun. 2007, Issue 6, https://doi.org/10.1371/journal.pone.0000514.

Galarneau A, Mehlhorn D, Guenneau F, Coasne B, Villemot F, Minoux D, Aquino C, Dath JP. Specific Surface Area Determination for Microporous/Mesoporous Materials: The Case of Mesoporous FAU-Y Zeolites. Langmuir. Nov. 27, 2018;34(47):14134-14142. doi: 10.1021/acs.langmuir.8b02144. Epub Nov. 14, 2018. PMID: 30379547.

Wong Po Foo C, Patwardhan SV, Belton DJ, Kitchel B, Anastasiades D, Huang J, Naik RR, Perry CC, Kaplan DL. Novel nanocomposites from spider silk-silica fusion (chimeric) proteins. Proc Natl Acad Sci U S A. Jun. 20, 2006;103(25):9428-33. doi: 10.1073/pnas. 0601096103. Epub Jun. 12, 2006. PMID: 16769898; PMCID: PMC1476692.

Heidebrecht A, Eisoldt L, Diehl J, Schmidt A, Geffers M, Lang G, Scheibel T. Biomimetic fibers made of recombinant spidroins with the same toughness as natural spider silk. Adv Mater. Apr. 1, 2015;27(13):2189-94. doi: 10.1002/adma.201404234. Epub Feb. 16, 2015. PMID: 25689835.

Amazon.com, "Amazon Brand—Solimo Sport Suncreen Lotion, Formulated without Octinoxate & Oxybenzone, 8 Fluid Ounce"— Product Page; Available online: [https://a.co/d/b8wTPxi]; 2019, 12pp.

Arcidiacono, S. et al. Aqueous Processing and Fiber Spinning of Recombinant Spider Silks. Macromolecules 2002, 35, 4, 1262-1266. https://doi.org/10.1021/ma0114710.

Carravetta, V. et al. An atomistic explanation of the ethanol-water azeotrope. Phys. Chem. Chem. Phys., 2022,24, 26037-26045. DOI: https://doi.org/10.1039/D2CP03145K.

Hardy, J. G. & Scheibel, T. R. Composite materials based on silk proteins. Progress in Polymer Science. vol. 35, Issue 9, Sep. 2010, pp. 1093-1115. https://doi.org/10.1016/j.progpolymsci.2010.04. 005.

Horsley, L. H. Table of Azeotropes and Nonazeotropes. Anal. Chem. 1947, 19, 8, 508-600. https://doi.org/10.1021/ac60008a002.

Huang X, Liu G, Wang X. New secrets of spider silk: exceptionally high thermal conductivity and its abnormal change under stretching. Adv Mater. Mar. 15, 2012;24(11):1482-6. doi: 10.1002/adma. 201104668. Epub Mar. 5, 2012. PMID: 22388863.

Koperska, M.A. et al. Fibroin degradation—Critical evaluation of conventional analytical methods. Polymer Degradation and Stability. vol. 120, Oct. 2015, pp. 357-367. https://doi.org/10.1016/j. polymdegradstab.2015.07.006.

Muhammad, R., Nah, Y. C., & Oh, H. (2023). Spider silk-derived nanoporous activated carbon fiber for CO2 capture and CH4 and H2 storage. Journal of CO2 Utilization, 69, 102401. https://doi.org/10. 1016/j.jcou.2023.102401.

Y. Park, Y. Lim and J. Lee, "n-Propanol aqueous solution shows nonlinearity in liquid level depending on water proportion," 2015 15th International Conference on Control, Automation and Systems (ICCAS), Busan, Korea (South), 2015, pp. 258-260, doi: 10.1109/ ICCAS.2015.7364917.

Roberts AD, Lee JM, Magaz A, Smith MW, Dennis M, Scrutton NS, Blaker JJ. Hierarchically Porous Silk/Activated-Carbon Composite Fibres for Adsorption and Repellence of Volatile Organic Compounds. Molecules. Mar. 7, 2020;25(5):1207. doi: 10.3390/ molecules25051207. PMID: 32156015; PMCID: PMC7179458.

Teagarden DL, Baker DS. Practical aspects of lyophilization using non-aqueous co-solvent systems. Eur J Pharm Sci. Mar. 2002;15(2):115-33. doi: 10.1016/s0928-0987(01)00221-4. PMID: 11849908.

Radu IC, Biru IE, Damian CM, Ion AC, Iovu H, Tanasa E, Zaharia C, Galateanu B. Grafting versus Crosslinking of Silk Fibroin-g-PNIPAM via Tyrosine-NIPAM Bridges. Molecules. Nov. 13, 2019;24(22):4096. doi: 10.3390/ molecules24224096. PMID: 31766195; PMCID: PMC6891396.

Chen, M., 2005. Amended final report of the safety assessment of t-Butyl Alcohol as used in cosmetics. International Journal of Toxicology, 24, pp. 1-20.

Lu, Z., Su, Z., Song, S., Zhao, Y., Ma, S. and Zhang, M., 2018. Toward high-performance fibrillated celluiose-based air filter via constructing spider-web like structure with the aid of TBA during freeze-drying process. Cellulose, 25(1), pp. 619-629.

Murphy, A.R., John, PS. and Kaplan, UL, 2008. Modification of silkfibroin using diazonium coupling chemistry and the effects on hMSC proliferation and differentiation. Biomaterials, 29(19), pp.2829-2838. doi: 10.1016/j.biomaterials.2008.03.039. Epub Apr 15, 2008.

Liebmann B, Hümmerich D, Scheibel T, Fehr M. Formulation of poorly water-soluble substances using self-assembling spider silk protein. Colloids and Surfaces A: Physicochemical and Engineering Aspects. Dec. 10, 2008;331(1-2):126-32.†

* cited by examiner
† cited by third party

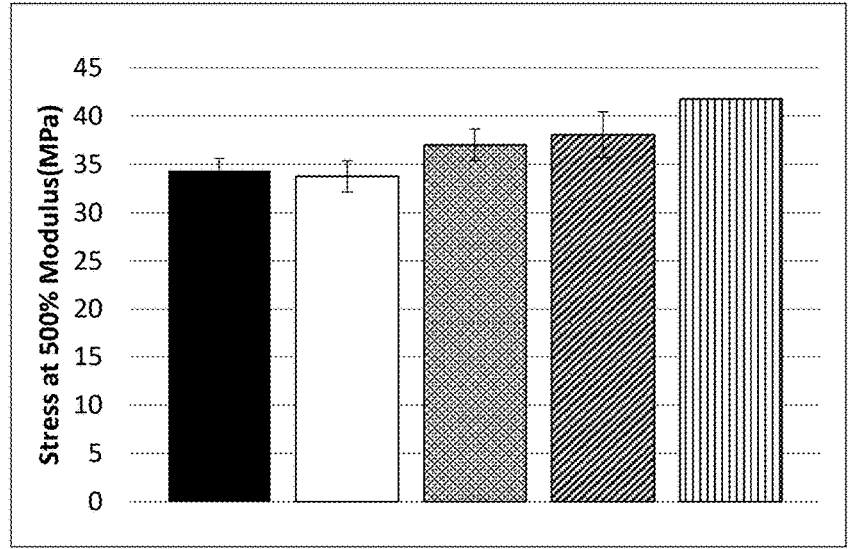
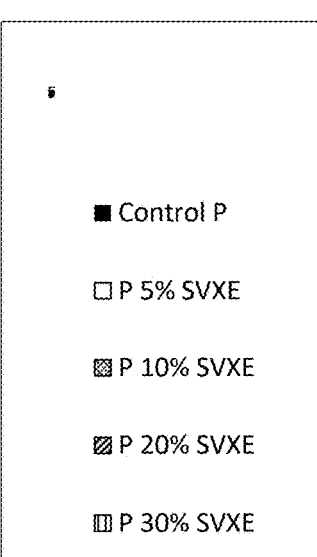
Figure 8A

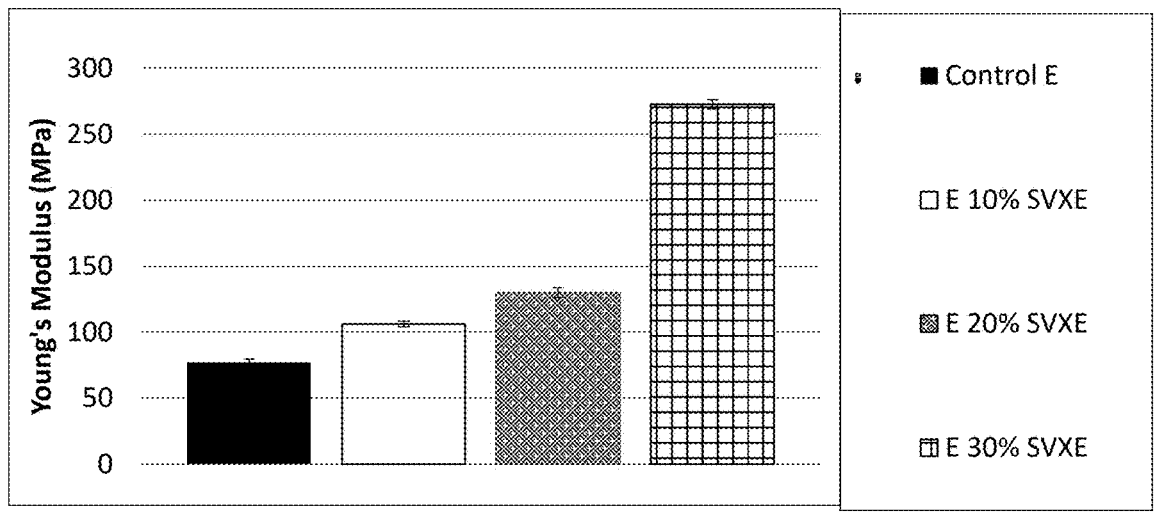
Figure 9A
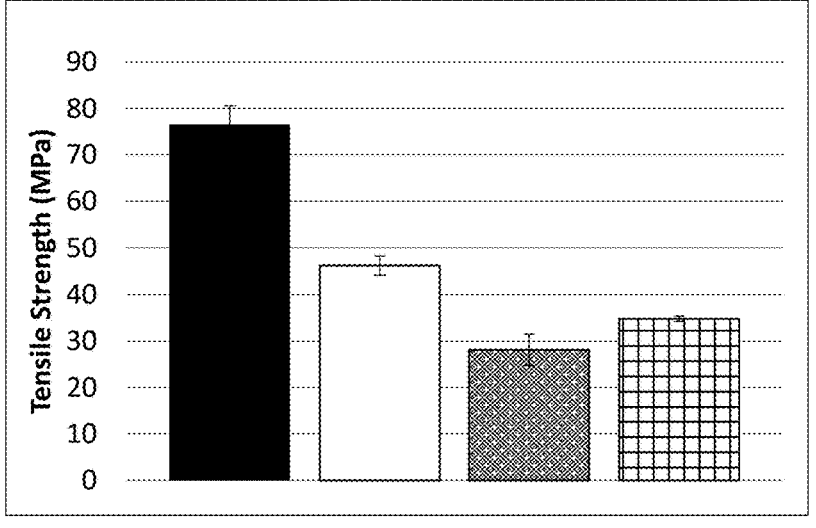
Figure 9B

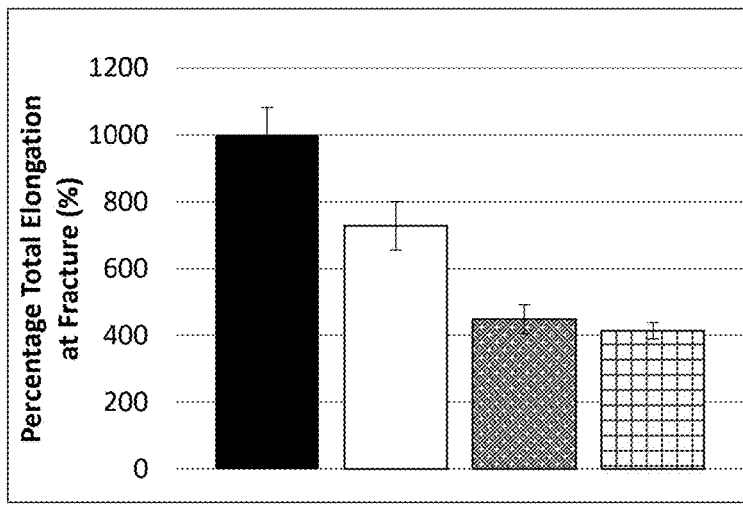
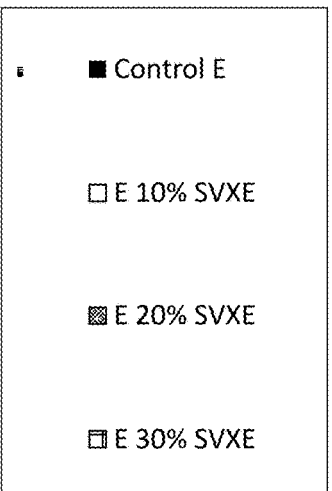
Figure 9C
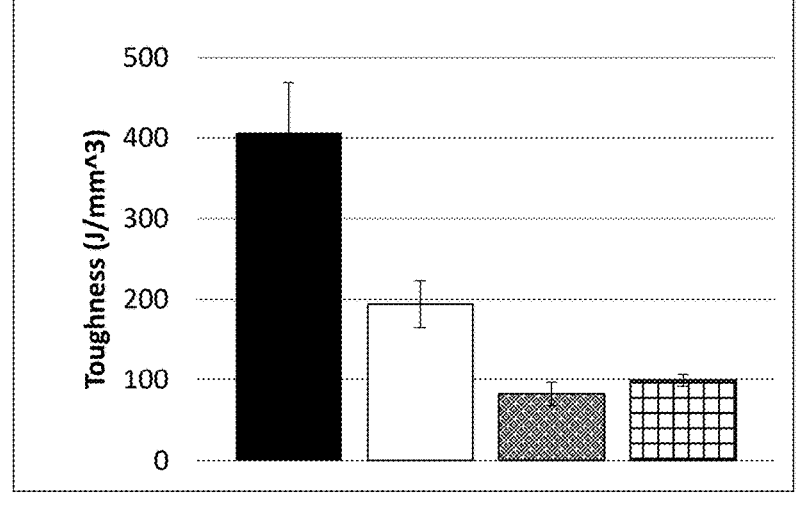
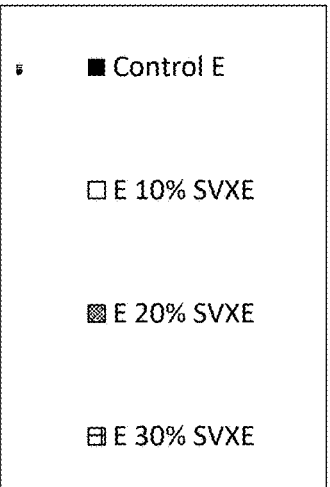
Figure 9D

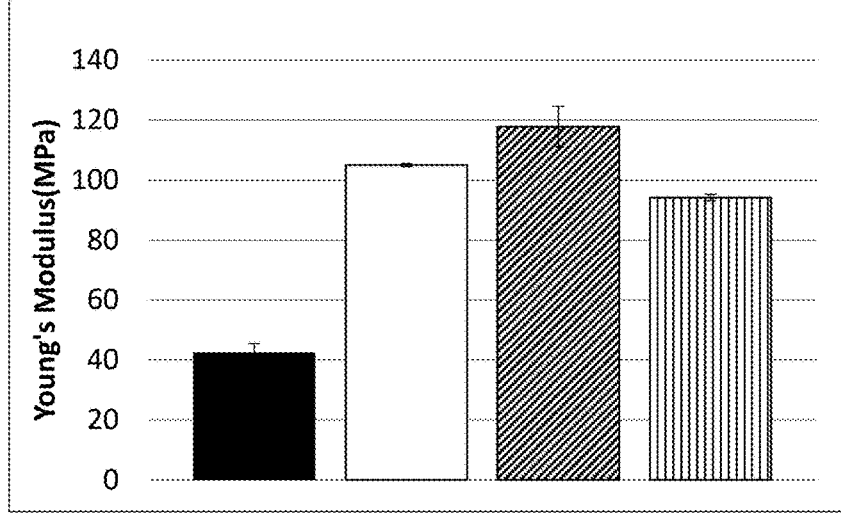
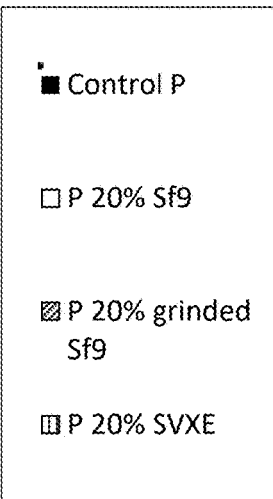
Figure 10A
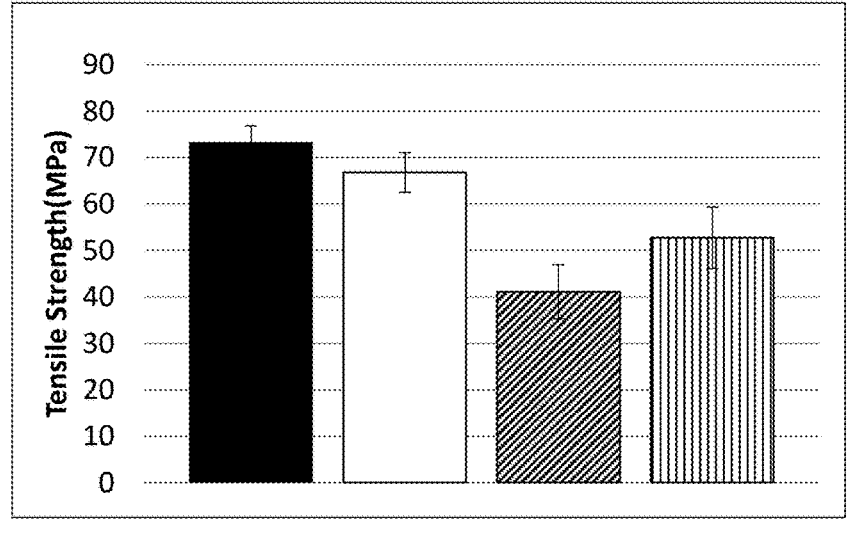
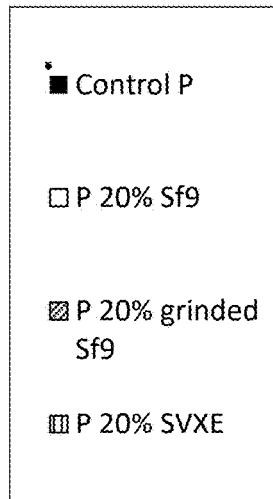
Figure 10B

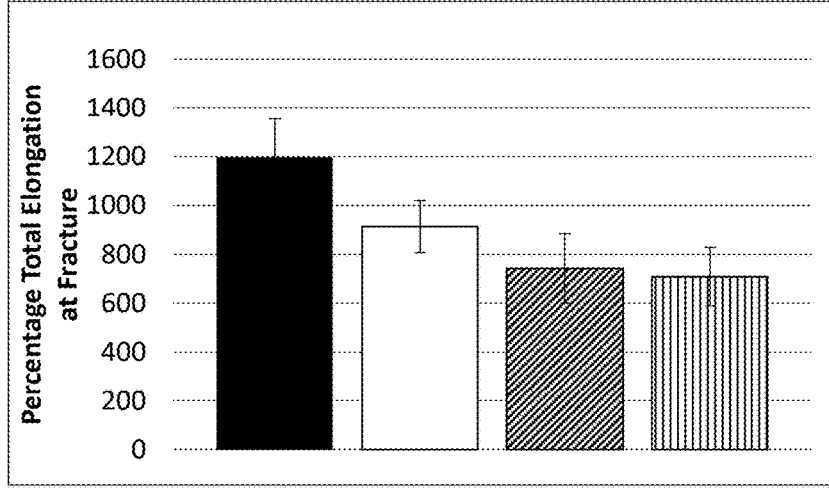
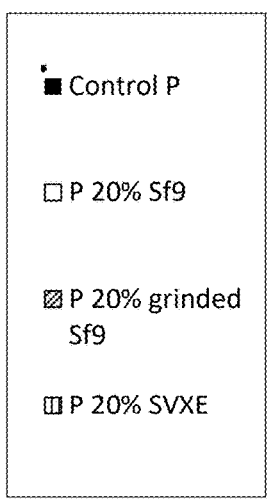
Figure 10C
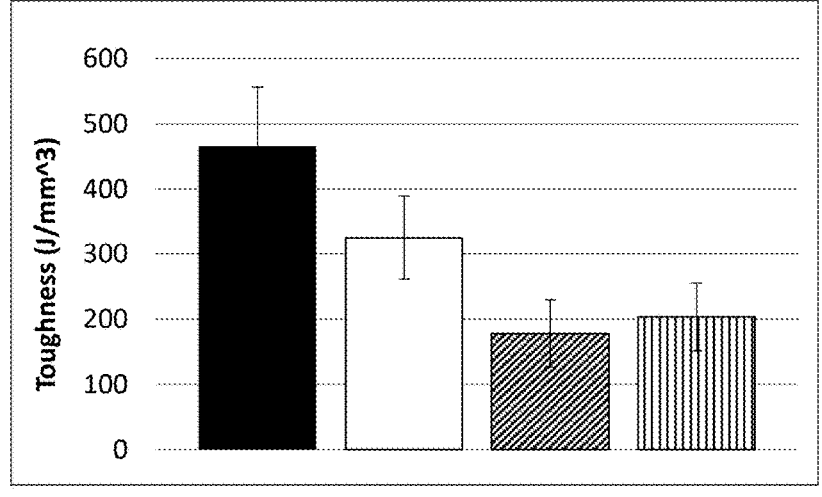
Figure 10D

| Film former | Young's modulus | UTS | Storage modulus | Loss modulus |
|---|---|---|---|---|
| Intansyl | - | - | Emergence of Stor. Modulus | 10% increase |
| SKI Nacture | - | - | Emergence of Stor. Modulus | 30% increase |
| TriK Fision | - | - | 20% increase | 25% increase |
| LiftLiss SB | - | - | 500% increase | 30% increase |
| Pullulan | 70% increase | 73% increase | 300% increase | 40% increase |
| Liftonin Xpress | 107% increase | 145% increase | 50% decrease | 40% decrease |
| Gosulin Agave | - | - | 500% increase | 60% increase |

Figure 14

SEQUENCE LISTING

```
<160> NUMBER OF SEQ ID NOS: 11

<210> SEQ ID NO 1
<211> LENGTH: 555
<212> TYPE: PRT
<213> ORGANISM: Artificial Sequence
<220> FEATURE:
<223> OTHER INFORMATION: Synthetic

<400> SEQUENCE: 1

Ala Ala Ala Ala Ala Ala Ala Ser Gly Ser Gly Gly Tyr Gly Pro Glu
1               5                   10                  15

Asn Gln Gly Pro Ser Gly Pro Val Ala Tyr Gly Pro Gly Gly Pro Val
            20                  25                  30

Ser Ser Ala Ala Ala Ala Ala Ala Ala Gly Ser Gly Pro Gly Gly Tyr
        35                  40                  45

Gly Pro Glu Asn Gln Gly Pro Ser Gly Pro Gly Gly Tyr Gly Pro Gly
    50                  55                  60

Gly Ser Gly Ser Ser Ala Ala Ala Ala Ala Ala Ala Ala Ser Gly Pro
65                  70                  75                  80

Gly Gly Tyr Gly Pro Gly Ser Gln Gly Pro Ser Gly Pro Gly Gly Ser
                85                  90                  95

Gly Gly Tyr Gly Pro Gly Ser Gln Gly Pro Ser Gly Pro Gly Ala Ser
                100                 105                 110

Ser Ala Ala Ala Ala Ala Ala Ala Ala Ser Gly Pro Gly Gly Tyr Gly
        115                 120                 125

Pro Gly Ser Gln Gly Pro Ser Gly Pro Gly Ala Tyr Gly Pro Gly Gly
    130                 135                 140

Pro Gly Ser Ser Ala Ala Ala Ser Gly Pro Gly Gly Tyr Gly Pro Gly
145                 150                 155                 160

Ser Gln Gly Pro Ser Gly Pro Gly Gly Ser Gly Gly Tyr Gly Pro Gly
                165                 170                 175

Ser Gln Gly Pro Ser Gly Pro Gly Gly Pro Gly Ala Ser Ala Ala Ala
            180                 185                 190

Ala Ala Ala Ala Ala Ala Ser Gly Pro Gly Gly Tyr Gly Pro Gly Ser
```

-continued

```
                195                 200                 205

Gln Gly Pro Ser Gly Pro Gly Ala Tyr Gly Pro Gly Gly Pro Gly Ser
    210                 215                 220

Ser Ala Ala Ala Ser Gly Pro Gly Gly Tyr Gly Pro Gly Ser Gln Gly
225                 230                 235                 240

Pro Ser Gly Pro Gly Ala Tyr Gly Pro Gly Gly Pro Gly Ser Ser Ala
                245                 250                 255

Ala Ala Ala Ala Ala Ala Gly Ser Gly Pro Gly Gly Tyr Gly Pro Gly
                260                 265                 270

Asn Gln Gly Pro Ser Gly Pro Gly Gly Tyr Gly Pro Gly Gly Pro Gly
                275                 280                 285

Ser Ser Ala Ala Ala Ala Ala Ala Ser Gly Pro Gly Gly Tyr Gly
                290                 295                 300

Pro Gly Ser Gln Gly Pro Ser Gly Pro Gly Val Tyr Gly Pro Gly Gly
305                 310                 315                 320

Pro Gly Ser Ser Ala Ala Ala Ala Ala Ala Gly Ser Gly Pro Gly
                325                 330                 335

Gly Tyr Gly Pro Gly Asn Gln Gly Pro Ser Gly Pro Gly Gly Tyr Gly
                340                 345                 350

Pro Gly Gly Ser Gly Ser Ser Ala Ala Ala Ala Ala Ala Ala Ala Ser
                355                 360                 365

Gly Pro Gly Gly Tyr Gly Pro Gly Ser Gln Gly Pro Ser Gly Pro Gly
    370                 375                 380

Gly Ser Gly Gly Tyr Gly Pro Gly Ser Gln Gly Pro Ser Gly Pro Gly
385                 390                 395                 400

Ala Ser Ser Ala Ala Ala Ala Ala Ala Ala Ser Gly Pro Gly Gly
                405                 410                 415

Tyr Gly Pro Gly Ser Gln Gly Pro Ser Gly Pro Gly Ala Tyr Gly Pro
                420                 425                 430

Gly Gly Pro Gly Ser Ser Ala Ala Ala Ser Gly Pro Gly Gly Tyr Gly
                435                 440                 445

Pro Gly Ser Gln Gly Pro Ser Gly Pro Gly Ala Tyr Gly Pro Gly Gly
    450                 455                 460

Pro Gly Ser Ser Ala Ala Ala Ala Ala Ala Ser Gly Pro Gly Gly
465                 470                 475                 480

Tyr Gly Pro Gly Ser Gln Gly Pro Ser Gly Pro Gly Gly Ser Arg Gly
                485                 490                 495

Tyr Gly Pro Gly Ser Gln Gly Pro Gly Gly Pro Gly Ala Ser Ala Ala
                500                 505                 510

Ala Ala Ala Ala Ala Ala Ser Gly Pro Gly Gly Tyr Gly Pro Gly
    515                 520                 525

Ser Gln Gly Pro Ser Gly Pro Gly Tyr Gln Gly Pro Ser Gly Pro Gly
    530                 535                 540

Ala Tyr Gly Pro Ser Pro Ser Ala Ser Ala Ser
545                 550                 555
```

<210> SEQ ID NO 2
<211> LENGTH: 27
<212> TYPE: PRT
<213> ORGANISM: Artificial Sequence
<220> FEATURE:
<223> OTHER INFORMATION: Synthetic

<400> SEQUENCE: 2

Ser Gly Pro Gly Gly Tyr Gly Pro Gly Ser Gln Gly Pro Ser Gly Pro

```
1              5              10             15

Gly Gly Tyr Gly Pro Gly Gly Pro Gly Ser Ser
                20                    25

<210> SEQ ID NO 3
<211> LENGTH: 35
<212> TYPE: PRT
<213> ORGANISM: Artificial Sequence
<220> FEATURE:
<223> OTHER INFORMATION: Synthetic

<400> SEQUENCE: 3

Ala Ala Ala Ala Ala Ala Ala Ala Ser Gly Pro Gly Gly Tyr Gly Pro
1               5                   10                  15

Gly Ser Gln Gly Pro Ser Gly Pro Gly Gly Tyr Gly Pro Gly Gly Pro
                20                  25                  30

Gly Ser Ser
        35

<210> SEQ ID NO 4
<211> LENGTH: 40
<212> TYPE: PRT
<213> ORGANISM: Artificial Sequence
<220> FEATURE:
<223> OTHER INFORMATION: Synthetic

<400> SEQUENCE: 4

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Arg Arg Arg Ala Gln Leu Val
        35                  40

<210> SEQ ID NO 5
<211> LENGTH: 50
<212> TYPE: PRT
<213> ORGANISM: Artificial Sequence
<220> FEATURE:
<223> OTHER INFORMATION: Synthetic

<400> SEQUENCE: 5

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Arg Arg Arg Ala Gln Leu Val Arg Pro Leu Ser Asn Leu Asp Asn
        35                  40                  45

Ala Pro
    50

<210> SEQ ID NO 6
<211> LENGTH: 54
<212> TYPE: PRT
<213> ORGANISM: Artificial Sequence
<220> FEATURE:
<223> OTHER INFORMATION: Synthetic

<400> SEQUENCE: 6

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
```

-continued

```
                20                    25                    30

Leu Arg Arg Arg Ala Gln Leu Val Asp Pro Pro Gly Cys Arg Asn Ser
        35                    40                    45

Ala Arg Ala Gly Ser Ser
    50

<210> SEQ ID NO 7
<211> LENGTH: 97
<212> TYPE: PRT
<213> ORGANISM: Artificial Sequence
<220> FEATURE:
<223> OTHER INFORMATION: Synthetic

<400> SEQUENCE: 7

Val Ala Ala Ser Arg Leu Ser Ser Pro Ala Ala Ser Ser Arg Val Ser
1               5                    10                   15

Ser Ala Val Ser Ser Leu Val Ser Ser Gly Pro Thr Asn Gly Ala Ala
            20                   25                    30

Val Ser Gly Ala Leu Asn Ser Leu Val Ser Gln Ile Ser Ala Ser Asn
        35                   40                    45

Pro Gly Leu Ser Gly Cys Asp Ala Leu Val Gln Ala Leu Leu Glu Leu
    50                   55                    60

Val Ser Ala Leu Val Ala Ile Leu Ser Ser Ala Ser Ile Gly Gln Val
65                   70                    75                    80

Asn Val Ser Ser Val Ser Gln Ser Thr Gln Met Ile Ser Gln Ala Leu
                85                    90                    95

Ser

<210> SEQ ID NO 8
<211> LENGTH: 35
<212> TYPE: PRT
<213> ORGANISM: Artificial Sequence
<220> FEATURE:
<223> OTHER INFORMATION: Synthetic

<400> SEQUENCE: 8

Ser Gly Pro Gly Gly Tyr Gly Pro Gly Ser Gln Gly Pro Ser Gly Pro
1               5                    10                   15

Gly Gly Tyr Gly Pro Gly Gly Pro Gly Ser Ser Ala Ala Ala Ala Ala
            20                   25                    30

Ala Ala Ala
        35

<210> SEQ ID NO 9
<211> LENGTH: 105
<212> TYPE: DNA
<213> ORGANISM: Artificial Sequence
<220> FEATURE:
<223> OTHER INFORMATION: Synthetic

<400> SEQUENCE: 9
tctggtcctg gaggttatgg cccaggaagc caaggaccat ctggtccagg aggatatggt      60
ccaggcggac ctggctctag tgcagcagct gccgcagcag ctgca                     105

<210> SEQ ID NO 10
<211> LENGTH: 37
<212> TYPE: PRT
<213> ORGANISM: Artificial Sequence
<220> FEATURE:
<223> OTHER INFORMATION: Synthetic
```

```
<400> SEQUENCE: 10

Met Ser Tyr Tyr His His His His His His Asp Tyr Asp Ile Pro Thr
1               5                   10                  15

Thr Glu Asn Leu Tyr Phe Gln Gly Ala Met Pro Arg Lys Ser Pro Phe
            20                  25                  30

Pro Arg Pro Glu Leu
        35

<210> SEQ ID NO 11
<211> LENGTH: 35
<212> TYPE: PRT
<213> ORGANISM: Artificial Sequence
<220> FEATURE:
<223> OTHER INFORMATION: Synthetic

<400> SEQUENCE: 11

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala
        35
```

PROKARYOTIC EXPRESSION SYSTEM AND METHODS OF USING THE SAME

CROSS REFERENCE TO RELATED APPLICATIONS

This application is a National Phase of PCT Patent Application No. PCT/IL2020/050752 having International filing date of Jul. 5, 2020, which claims the benefit of priority under 35 USC § 119(e) of U.S. Provisional Patent Application No. 62/870,750, filed Jul. 4, 2019, entitled "PROKARYOTIC EXPRESSION SYSTEM AND METHODS OF USING THE SAME", the contents of which are all incorporated herein by reference in their entirety.

FIELD OF INVENTION

The present invention is directed to synthetic dragline spider silk polymers.

BACKGROUND OF THE INVENTION

Dragline spider silk is known in the art as the silk used by the orb-web weaving spiders to construct the frame and radii of their webs as well a lifeline when they fall or escape danger. To be able to perform these tasks, the dragline fiber displays a remarkably high toughness due to combination of high elasticity and strength, which places it as the toughest fiber, whether natural or man-made. For instance, dragline is six times as strong as high-tensile steel in its diameter and three times tougher than Kevlar that is one of the strongest synthetic fibers ever made.

Dragline silk consists of two main polypeptides, mostly referred to as major ampullate spidroin (MaSp) 1 and 2, and also to ADF-3 and ADF-4 in *Araneus diadematus*. These proteins have apparent molecular masses in the range of 200-720 kDa, depending on sample age and conditions of analysis. The known dragline silk spidroins are composed of highly iterated blocks of alternating alanine-rich segments, forming crystalline β-sheets in the fiber, and glycine-rich segments which are more flexible and mainly lack ordered structure. The C-terminal region is non-repetitive, highly conserved between species, and adopts α-helical conformation. The N-terminal region of dragline silk proteins was also found to be highly conserved between different spidroins, and also between different spider species.

Numerous attempts have been made to synthetically create spider silk, such as through genetic engineering using bacteria, yeast, plants and mammalian cells in tissue culture and even transgenic goats.

U.S. Pat. No. 8,461,301 relates to, inter alia, isolated amino acid sequence comprising multiple repeats of a semi-synthetic spider silk protein domain, or any functional homolog, variant, derivative, fragment or mutant thereof. Additional publications relating to dragline spider silk include, but are not limited to, Ittah, S., et al. Biopolymers, 93 (5), 458-468, 2010; Ittah, S., et al. Biomacromolecules, 8 (9), 2768-2773, 2007; Ittah, S., et al., Biomacromolecules, 7 (6), 1790-1795, 2006; and Huemmerich, D., Ittah, S., et al., Current Biology, 14, 2070-2074, 2004.

There is an unmet need for improved compositions and methods for producing synthetic spider silk with mechanical properties similar to the natural spider silk.

SUMMARY OF THE INVENTION

The present invention is directed to a recombinant bacterium having the ability to produce a MaSp based protein organized in β-sheet crystalline structures, methods of producing MaSp-based polymers using same, and compositions comprising same.

According to one aspect, the present invention provides a composition comprising a synthetic major ampullate spidroin protein (MaSp)-based polymer in the form of particles having a size in the range of 0.5 μm to 1.5 μm.

In some embodiments, the MaSp-based polymer is a water insoluble polymer.

In some embodiments, the composition has a DSC pattern exhibiting at least an endothermic peak in the range of from 200° C. to 280° C.

In some embodiments, the particles are porous particles and are characterized by BET surface area of at least 10 m2/g.

In some embodiments, the particles comprise a plurality of nano-fibrils.

In some embodiments, the composition further comprising an additional compound in contact with the MaSp-based polymer.

In some embodiments, the compound is selected from a biologically active agent and a nutraceutical.

In some embodiments, a weight per weight (w/w) ratio of the MaSp-based polymer to said additional compound is between 10:1 and 1:10.

In some embodiments, the MaSp-based polymer comprises the amino acid sequence as set forth in SEQ ID NO: 2 (SGPGGYGPGSQGPSGPGGYGPGGPGSS).

In some embodiments, the MaSp-based polymer comprises the amino acid sequence as set forth in SEQ ID NO: 3 (AAAAAAAASGPGGYGPGSQGPSGPG-GYGPGGPGSS).

In some embodiments, the MaSp-based polymer comprises 10-20 repeats of SEQ ID NO: 3.

In some embodiments, the MaSp-based polymer comprises a single N-terminal region selected from the group consisting of: SEQ ID NO: 4 (MSYYHHHHHHDYDIPT-TENLYFQGAMDPEFKGLRRRAQLV).

In some embodiments, the MaSp-based polymer comprises a single C-terminal region selected from the group consisting of: SEQ ID NO: 7 (VAASRLSSPAASSRVS-SAVSSLVSSGPTNGAAVSGALNSLVSQ-ISASNPGLSGCDALVQALLELVSALVAILSSAS-IGQVNVSSVSQSTQMISQALS).

In some embodiments, the composition is obtained by expression of MaSp in a bacterium.

In some embodiments, the bacterium is *Escherichia coli*.

In another aspect, there is a composition comprising the MaSp-based polymer of the invention bound to an additional polymer, wherein a w/w ratio of said MaSp-based polymer to said additional polymer is between 1:1 and 1:100.

In some embodiments, a w/w concentration of said additional polymer is 50% to 95% (w/w) of the total composition.

In some embodiments, the additional polymer is selected from a synthetic polymer, a thermoplastic polymer, a thermoset, a film forming agent, an epoxy, a polyester a polyamide, a polyol, a polyurethane, polyethylene, a silicon, liquid crystal polymers, maleic anhydride grafted polypropylene, a polyacrylate, a polycarbonate, polyamides, Nylon 4,6, Nylon 6, Nylon 6,6, Nylon 11, Nylon 12, poly(arylamide), polyethylene, polybutylene terephthalate, polyethylene terephthalate, polyphenylene sulfide, polyphthalamide, polypropylene, poly(vinylidene fluoride), Poly(2-hydroxyethyl methacrylate) (pHEMA), polyurethane, polyvinyl butyral, ethylene vinyl alcohol copolymer, polylactide acid (PLA) or a copolymer thereof, polycaprolactone (PCL), xanthan, cellulose, collagen, elastin, keratin, cotton, rubber, cellulose, wool, and any combination thereof.

In some embodiments, the film forming agent is a solid film forming agent.

In some embodiments, a w/w ratio between said film forming agent and said MaSp based fiber is from 5:1 to 50:1.

In some embodiments, the composition is characterized by at least one improved mechanical property as compared to the property for the additional polymer free of the MaSp-based polymer, wherein the property is selected from the group consisting of: Young's modulus, tensile strength, fracture strain, yield point, toughness, work to failure, impact strength, tear strength, flexural modulus, flexural strain and stress at a specific percentage elongation, and abrasion.

According to another aspect, the present invention provides an article comprising the composition described herein, wherein the article is in a form of film, a suture, surgical mesh, medical adhesive strips, electrospun mesh, skin grafts, fat grafts, cosmetics, dermal fillers, drug eluting/ delivery device, replacement ligaments, clothing fabric, bullet-proof vest lining, cable, tube, film, rope, fishing line, tires, sports equipment, and reinforced plastics.

According to another aspect, the present invention provides a recombinant bacterium having the ability to express a MaSP-based polymer comprising the amino acid sequence as set forth in SEQ ID NO: 2 (SGPGGYGPGSQGPSGPG-GYGPGGPGSS).

According to another aspect, the present invention provides a process, comprising: (i) providing the recombinant bacterium described herein; (ii) providing conditions for expression of the MaSP by the bacterium; and (iii) isolating the expressed proteins, thereby fabricating the synthetic dragline spider silk.

In some embodiments, the step (ii) comprises providing a solution with a pH in the range of 5 to 6.5.

In some embodiments, the step (ii) comprises providing an expression inducer.

In some embodiments, the step (ii) comprises waiting during a period of time to obtain an insoluble polymer.

In some embodiments, the step (iii) further comprises drying of said synthetic dragline spider silk.

In some embodiments, the process further comprises an enrichment step with an additional polymer.

In some embodiments, the enrichment step comprises mixing a solution of the synthetic dragline spider silk, with solution of the second polymer.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 8A-B are graphs of the dose-dependent effect of SVXE on the mechanical properties of a polymer P490RSJT composite. FIG. 8A represents bar graphs showing an increased stress at 500% modulus (between 10 and 20% increase) of P490RSJT enriched with 10, 20, and 30% SVXE, compared to control (pristine P490RSJT polymer). FIG. 8B represents stress-strain curves of P490RSJT enriched with 5, 10, 20, and 30% SVXE, compared to control (pristine P490RSJT polymer).

FIGS. 9A-E are graphs of the dose-dependent effect of SVXE on the mechanical properties of a polymer E394POTA composite. FIG. 9A is a bar graph showing an increased Young's modulus (between about 50 and about 400% increase) of E394POTA enriched with 10, 20, and 30% SVXE, compared to control (pristine E394POTA polymer). FIGS. 9B-D are bar graphs showing a decrease in UTS (FIG. 9B), % elongation at break (FIG. 9C) and toughness (FIG. 9D) of E394POTA enriched with 10, 20, and 30% SVXE, compared to control (pristine E394POTA polymer). FIG. 9E represents stress-strain curves of E394POTA enriched with 10, 20, and 30% SVXE, compared to control (pristine E394POTA polymer).

FIGS. 10A-E are graphs of the comparison of mechanical properties of a polymer P490RSJT PU composite enriched with 20% SVX, grinded SVX & SVX-E. FIG. 10A is a bar graph showing an increased Young's modulus (between about 150 and about 300% increase) of the enriched P490RSJT PU, compared to control (pristine P490RSJT PU polymer). FIGS. 10B-D are bar graphs showing a decrease in UTS (FIG. 10B), % elongation at break (FIG. 10C) and toughness (FIG. 10D) of P490RSJT PU enriched with 10, 20, and 30% SVXE, compared to control (pristine P490RSJT PU polymer). FIG. 10E represents stress-strain curves of P490RSJT PU enriched with 20% SVX, grinded SVX & SVX-E, compared to control (pristine E394POTA polymer).

FIG. 14 is a table summarizing mechanical properties of film forming agents enriched with 10% w/w SVX-E.

FIG. 21A and FIG. 21B represent images of porous fibers. Arrow 1 points at the nanofibrils. FIG. 21C and FIG. 21D represent images of non-porous particles. FIG. 21E represent a fiber resulting from expression of a different sequence (SEQ ID NO: 10).

DETAILED DESCRIPTION OF THE INVENTION

In some embodiments, provided herein is a bacterium expressing a composition comprising a major ampullate spidroin protein (MaSp)-based protein, useful for the preparation of synthetic dragline spider silk. The invention further provides articles and composites comprising these compositions.

The present invention is based, in part, on the unexpected finding that a microorganism such as *E. coli* is unexpectedly efficient as a host for the production of the MaSp protein. The MaSp protein, is not only expressed in *E. coli*, but also self-assembles to form functional spider silk inside the bacterium. Surprisingly, this self-assembly occurs exclusively at external pH<7 but not at neutral pH 7-7.5.

The present invention is further based, in part, on the unexpected finding that the microorganism-produced MaSp protein (also used herein as SVX-E) unexpectedly possess exceptional mechanical properties compared to the natural dragline spider silk, or compared to the production of dragline spider silk proteins in other expression systems.

Figure 12:
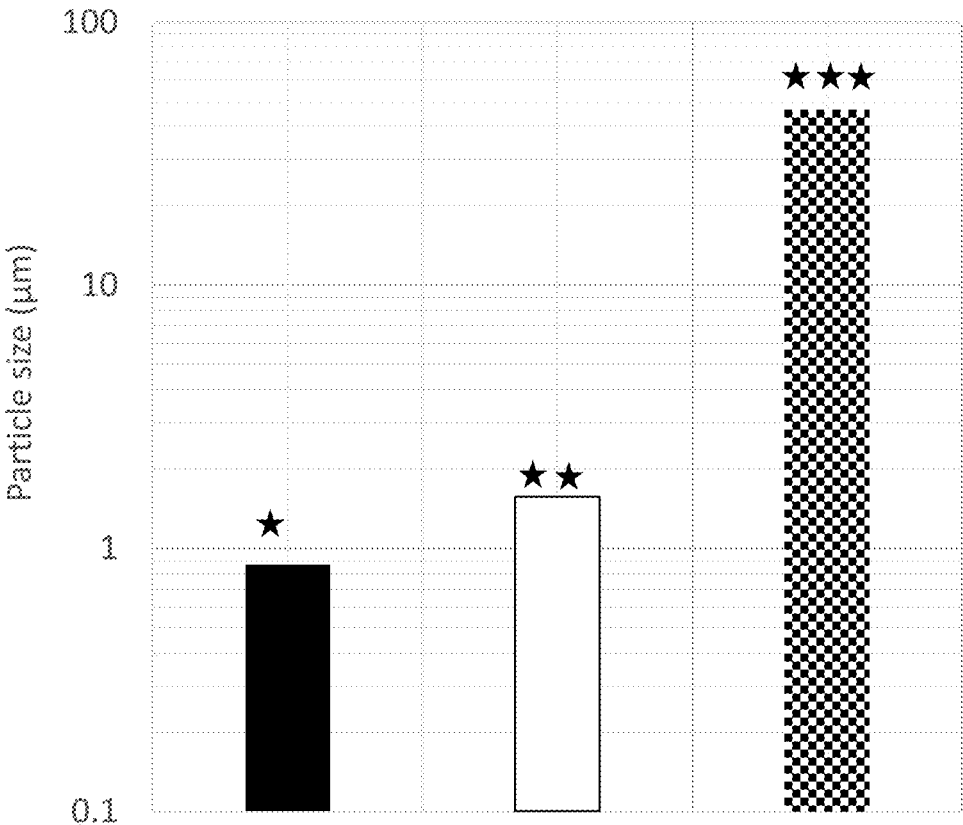
FIG. 12 is a bar graph exhibiting the size of SVX-E particles in an aqueous suspension as measured by LASER diffraction. * refers to an average size of SVX-E particles as isolated;  refers to an average size of porous or non-aggregated SVX-E particles after drying and resuspension; * refers to an average size of "non-porous" or aggregated SVX-E particles after drying and resuspension.

The present invention is further based, in part, on the unexpected finding that SVX-E-based fiber is in a form of particles having a size in the range of 0.5 μm to 1.5 μm. As exemplified herein (e.g. FIG. 12), these particles remain stable (e.g., substantially devoid of aggregates) in an aqueous dispersion, as opposed to control MaSp-based polymer. Furthermore, SVX-E-based fiber has been characterized by an increased porosity and by an extremely large BET surface area (e.g., of about 180 m²/g).

Compositions

According to some embodiments, there is provided a composition comprising a synthetic major ampullate spidroin protein (MaSp)-based polymer in the form of particles having a size in the range of 0.5 μm to 1.5 μm. In some embodiments, the MaSp-based polymer is an insoluble polymer. In some embodiments, the composition has a DSC pattern exhibiting at least an endothermic peak in the range of from 200° C. to 280° C. In some embodiments, the composition has an amide peak in the range of 1615 cm⁻¹ to 1635 cm⁻¹ as measured by FTIR analysis.

According to some embodiments, there is provided a composition comprising a synthetic MaSp-based polymer, wherein the MaSp-based polymer has at least one characterization selected from:
- a) being an insoluble polymer;
- b) being in the form of particles having a size in the range of 0.5 μm to 1.5 μm;
- c) having a BET surface area of at least 10 m²/g;
- d) having a DSC pattern exhibiting at least an endothermic peak in the range of from 200° C. to 280° C.; and
- e) having an amide peak in the range of 1615 cm⁻¹ and 1638 cm⁻¹ as measured by FTIR analysis.

According to some embodiments, there is provided a composition comprising a synthetic MaSp-based polymer in the form of particles. In some embodiments, the particles have a size in the range of 0.5 μm to 1.5 μm, 0.7 μm to 1.5 μm, 0.8 μm to 1.5 μm, 0.9 μm to 1.5 μm, 0.5 μm to 1 μm, 0.7 μm to 1 μm, 0.8 μm to 1 μm, 0.9 μm to 1 μm, 0.5 μm to 1.3 μm, 0.5 μm to 1.2 μm, 0.7 μm to 1.3 μm, 0.7 μm to 1.2 μm, or 0.9 μm to 1.2 μm, including any range therebetween. In some embodiments, particle size refers to an average particle size within an aqueous solvent (e.g. aqueous dispersion), as measured by laser diffraction (see Examples section). In some embodiments, particle size refers to a dry particle size (e.g. a size of a particle being substantially devoid of an outer shell comprising water molecules).

In some embodiments, there is provided a composition comprising an insoluble MaSp-based polymer. In some embodiments, the insoluble MaSp-based polymer is in the form of particles. In some embodiments, the insoluble MaSp-based polymer is insoluble in organic solvents. In some embodiments, the insoluble MaSp-based polymer is insoluble in aqueous solutions.

As used herein, the term "insoluble" refers to a material that, when exposed to an excess of solvent, does not dissolve, but may disperse to varying degrees. In some embodiments the term "insoluble" refers to a material that is less than 10%, less than 5%, less than 2%, or less than 1% soluble in a solvent. In some embodiments, "insoluble" refers to a material that can be partially dissolved in a solvent only at a concentration of less than 0.01% by weight. Solvents according to the present invention include organic solvents and aqueous solutions. In some embodiments, the solvent comprises an aqueous surfactant solution. Surfactants (e.g. ionic surfactants) are well-known in the art. In some embodiments, the solvent comprises urea aqueous solution.

In some embodiments, the disclosed composition is characterized by a defined differential scanning calorimetry (DSC) pattern. In some embodiments, by "DSC pattern" it is meant to refer to the position of the peaks. In some embodiments, by "peak" it is meant to refer to exothermic peak. Herein throughout, "the position of the peaks" or "peak position" refers to the peaks along the temperature axis in a thermogram pattern, and, in some embodiments, may refers to the peak position at any peak intensity. One skilled in the art will appreciate that the data obtained in DSC measurements depend, in part, on the instrument used and the environmental conditions at the time measurements are carried out (e.g., humidity).

In some embodiments, the disclosed composition is characterized by a DSC pattern exhibiting at least an endothermic peak in the range of from 200° C. to 280° C. In some embodiments, the disclosed composition is characterized by a DSC pattern exhibiting at least an endothermic peak in the range of from 200° C. to 270° C., 200° C. to 260° C., 200° C. to 250° C., 210° C. to 280° C., 212° C. to 280° C., 215° C. to 280° C., 216° C. to 280° C., 220° C. to 280° C., 210° C. to 250° C., 212° C. to 250° C., 215° C. to 250° C., 216° C. to 250° C., 220° C. to 250° C., 210° C. to 245° C., 210° C. to 242° C., or 215° C. to 245° C., including any range therebetween.

In some embodiments, the disclosed composition is characterized by a DSC pattern exhibiting at least an endothermic peak with at least 5° C. to 100° C., at least 10° C. to 100° C., at least 15° C. to 100° C., at least 12° C. to 100° C., at least 2° C. to 100° C., at least 5° C. to 80° C., at least 10° C. to 80° C., at least 15° C. to 80° C., at least 12° C. to 80° C., at least 25° C. to 80° C., at least 5° C. to 50° C., at least 10° C. to 50° C., at least 15° C. to 50° C., at least 12° C. to 5° C., or at least 25° C. to 50° C., lower than the DSC pattern of an corresponding composition comprising a (MaSp)-based fiber.

In some embodiments, the disclosed composition is devoid of DSC peaks in the range of about −100° C. to about 190° C. In some embodiments, the disclosed compound is devoid of DSC peaks in the range of about −100° C. to about 25° C. In some embodiments, the disclosed composition is characterized by at least a DSC pattern exhibiting devoid of an exothermic peak in the range of 40° C. to 70° C.

In some embodiments, the disclosed composition is devoid of DSC peaks in the range of about −100° C. to about −50° C. In some embodiments, the disclosed compound is devoid of DSC peaks in the range of about −50° C. to about 0° C. In some embodiments, the disclosed compound is devoid of DSC peaks in the range of about −0° C. to about −25° C.

In some embodiments, the disclosed composition is characterized by having an amide peak in the range of 1615 cm$^{-1}$ to 1635 cm$^{-1}$, as measured by FTIR analysis. In some embodiments, the disclosed composition is characterized by having an amide peak in the range of 1620 cm$^{-1}$ to 1635 cm$^{-1}$, 1620 cm$^{-1}$ to 1630 cm$^{-1}$, 1621 cm$^{-1}$ to 1630 cm$^{-1}$, or 1620 cm$^{-1}$ to 1625 cm$^{-1}$, including ay range therebetween, as measured by FTIR analysis.

In some embodiments, the disclosed composition is devoid of a peak in the range of 1700 cm$^{-1}$ to 1800 cm$^{-1}$, as measured by FTIR analysis.

By one embodiment, the MaSp-based polymer of the invention assembles by self-assembly. By "self-assembly" it is meant that monomers, i.e., the synthetic spider silk protein of the invention, bind each other spontaneously, in an energetically favorable manner, under normal physiologic conditions, or at room temperature, to create the macromolecular structure having the properties described herein. Furthermore, the MaSp-based polymers of the invention are extremely resilient, and once assembled, may withstand extreme chemical assaults, such as solubilization in 10% w/w surfactant solution and boiling for at least 1 hour.

"Tenacity" or "tensile strength" refers to the amount of weight a filament can bear before breaking. The maximum specific stress that is developed is usually in the filament, yarn or fabric by a tensile test to break the materials. According to specific embodiments, the MaSp-based polymer of the invention has tensile strength of about 100-3000 MPa (MPa=N/mm2), about 300-3000 MPa, about 500-2700 MPa, about 700-2500 MPa, about 900-2300 MPa, about 1100-2000 MPa, about 1200-1800 MPa, about 1300-1700 MPa or about 1400-1600 MPa. More specifically, about 1500 MPa.

"Toughness" refers to the energy needed to break the MaSp-based polymer. This is the area under the stress strain curve, sometimes referred to as "energy to break" or work to rupture. According to particular embodiments, the MaSp-based polymer of the invention a toughness of about 20-1000 MJ/m3, about 50-950 MJ/m3, about 100-900 MJ/m3, about 120-850 MJ/m3, about 150-800 MJ/m3, about 180-700 MJ/m3, about 180-750 MJ/m3, about 250-700 MJ/m3, about 280-600 MJ/m3, about 300-580 MJ/m3, about 310-560 MJ/m3, about 320-540 MJ/m3 or about 350-520 MJ/m3, most specifically about 350-520 MJ/m3.

"Elasticity" refers to the property of a body which tends to recover its original size and shape after deformation. Plasticity, deformation without recovery, is the opposite of elasticity. On a molecular configuration of the MaSp-based polymer, recoverable or elastic deformation is possible by stretching (reorientation) of inter-atomic and inter-molecular structural bonds. Conversely, breaking and re-forming of intermolecular bonds into new stabilized positions causes non-recoverable or plastic deformations.

"Extension" refers to an increase in length expressed as a percentage or fraction of the initial length.

By "fineness" is meant the mean diameter of a MaSp-based polymer or filament (e.g., a biofilament), which is usually expressed in microns (micrometers).

According to some aspects, the MaSp-based protein or the MaSp-based polymer which are used herein interchangeably, is in the form of a fiber. A "fiber" as used herein, is meant a fine cord of fibrous material composed of two or more filaments twisted together. By "filament" is meant a slender, elongated, threadlike object or structure of indefinite length, ranging from microscopic length to lengths of a mile or greater. Specifically, the synthetic spider silk filament is microscopic, and is proteinaceous. By "biofilament" is meant a filament created from a protein, including recombinantly produced spider silk protein. In some embodiments, the term "fiber" does not encompass unstructured aggregates or precipitates.

In some embodiments, the MaSp-based fiber comprises a plurality of MaSp-based polymers. In some embodiments, the plurality of MaSp-based polymers comprises polymers having a different chemical composition and/or a different molecular weight (MW). In some embodiments, the plurality of MaSp-based polymers comprises polymers having a different number of repetitive regions.

In some embodiments, the MaSp-based polymer or the MaSp-based fiber is substantially devoid of an additional non-MaSp-based protein. In one embodiment, the MaSp-based polymer or the MaSp-based fiber is substantially devoid of an additional polymer (e.g. a synthetic polymer, a non-MaSp-based peptide, non-MaSp-based protein).

In some embodiments, the fiber of the proteins is characterized by size of at least one dimension thereof (e.g., diameter, length). For example, and without limitation, the diameter of the fiber is between 10 nm-1 μm, 20-100 nm, or 10-50 nm.

Figure 21A:
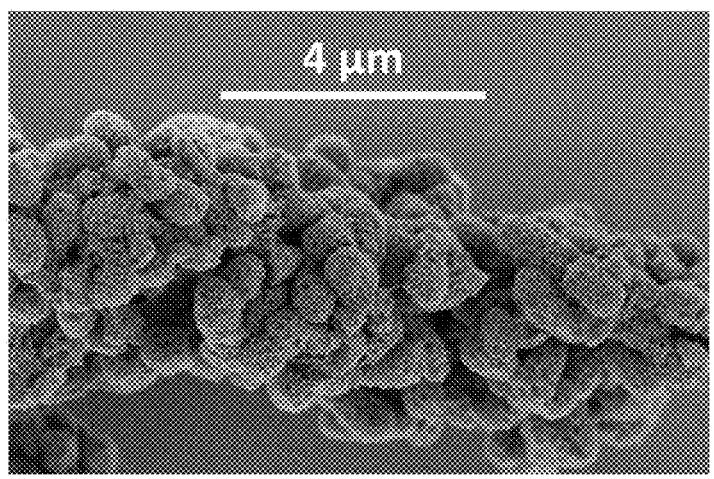
FIGS. 21A-E are scanning electron micrographs (SEM) of MaSp-based (SVX) fibers.
Figure 21B:
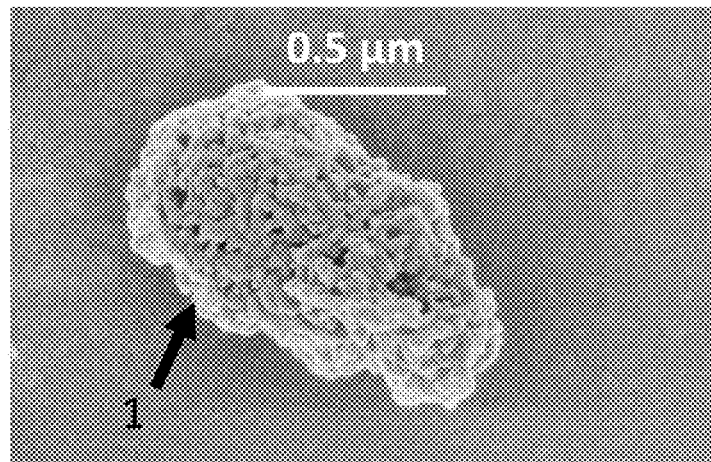

In one embodiment, the MaSp-based fiber is composed of monomers. In one embodiment, a plurality of MaSp-based polymers are arranged in a nanofibril. In one embodiment, a plurality of nanofibrils are arranged in a fiber or make-up a fiber. In one embodiment, a monomer or a nanofibril within the MaSp-based fiber has a diameter of 4 to 16 nm. In one embodiment, a monomer or a nanofibril within the MaSp-based fiber has a diameter of 6 to 14 nm. In one embodiment, a monomer or a nanofibril within the MaSp-based fiber has a diameter of 8 to 12 nm. In some embodiments, the MaSp-based fiber comprises a plurality of fibrils (e.g. nanofibrils), as exemplified hereinbelow (FIGS. 21A-B). In some embodiments, a fiber having a mutated amino acid sequence (e.g. an amino acid sequence as set forth in SEQ ID NO: 10 (MSYYHHHHHHDYDIPTTENLYFQGAMPRKSPFPR-PEL) is substantially devoid of nanofibrils, as exemplified by FIG. 21E. In some embodiments, a fiber having a mutated amino acid sequence (e.g. an amino acid sequence as set forth in SEQ ID NO: 10 (MSYYHHHHHHDYDIPTTEN-LYFQGAMPRKSPFPRPEL) is in a form of a non-porous particle, as exemplified by FIG. 21E.

In some embodiments, the nano-fibrils have a diameter of e.g., 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 40 nm, about 42 nm, about 44 nm, about 46 nm, about 48 nm, or about 50 nm, including any value or range therebetween. In one embodi-ment, the nano-fibrils have a diameter of 3-7 nm. In one embodiment, the nano-fibrils have a diameter of 4-6 nm.

In one embodiment, the MaSp-based fiber has a diameter of 70 to 450 nm. In one embodiment, the MaSp-based fiber has a diameter of 80 to 350 nm. In one embodiment, the MaSp-based fiber has a diameter of 80 to 300 nm. In one embodiment, the MaSp-based fiber has a diameter of 150 to 250 nm. In one embodiment, the MaSp-based fiber or the MaSp-based polymer is arranged as a coil. In one embodi-ment, a single fiber or one the MaSp-based polymer is arranged as a coil. In one embodiment, a coil has a diameter of 5 to 800 micrometers. In one embodiment, a coil has a diameter of 5 to 500 micrometers. In one embodiment, a coil has a diameter of 5 to 30 micrometers. In one embodiment, a coil has a diameter of 5 to 20 micrometers. In one embodiment, the MaSp-based fiber or the MaSp-based poly-mer has a length of 5 to 800 micrometers. In one embodi-ment, the MaSp-based fiber or the MaSp-based polymer has a length of 30 to 300 micrometers. In some embodiments, the length of the MaSp-based fiber is between 1-200 μm, 10-100 μm, 100 to 500 μm or 200-500 μm, including any range therebetween.

In some embodiments, the MaSp-based fiber comprises a plurality of pores. In some embodiments, the MaSp-based fiber is in a form of a particle, as described herein. In some embodiments, the composition comprises a plurality of MaSp-based fibers. In some embodiments, the plurality of MaSp-based fibers comprises fibers having a different chemical composition. In some embodiments, the plurality of MaSp-based fibers are in a form of particles having different size and/or different structure. In some embodi-ments, the plurality of MaSp-based fibers are in a form of particles having different porosity (expressed by BET sur-face area).

In some embodiments, the MaSp-based fiber is charac-terized by a porous structure. In some embodiments, the MaSp-based fiber is a porous fiber. In some embodiments, the porous structure or the porous MaSp-based fiber is characterized by a porosity of at least 30% (e.g., from 30 to 99%). In some embodiments, the porous structure is char-acterized by a porosity of at least 50% (e.g., from 50 to 99%). In some embodiments, the porous structure is char-acterized by a porosity of at least 60% (e.g., from 60 to 99%). In some embodiments, the porous structure is char-acterized by a porosity of at least 70% (e.g., from 70 to 99%). In some embodiments, the porous structure is char-acterized by a porosity of at least 80% (e.g., from 80 to 99%). In some embodiments, the porous structure is char-acterized by a porosity of at least 90% (e.g., from 90 to 99%). In some embodiments, the porous structure is char-acterized by a porosity of about 90%.

Herein, the term "porosity" refers to a percentage of the volume of a substance (e.g., a "sponge-like" material) which consists of voids. In another embodiment, porosity is mea-sured according to voids within the surface area divided to the entire surface area (porous and non-porous).

In some embodiments, the porous structure of the dis-closed fibers allows absorbing water efficiently on the fiber surface. That is, and without being bound by any particular theory, this surprising discovery can be explained in view of the disclosed fiber structure and its porosity which is in sharp distinction from native spider silk found in nature.

In some embodiments, the porous MaSp-based fiber is in a form of a particle, as described herein. In some embodi-ments, the particle is a porous particle. In some embodi-ments, the particle is substantially non-aggregated particle. In some embodiments, the particle comprising a plurality of pores (i.e. a space or lumen) formed by the intertwisted polymeric chains of the MaSp-based polymer. In some embodiments, the entangled or intertwined MaSp-based polymers form a matrix. In some embodiments, the cosmetic active ingredient fills at least a portion of the pores within the matrix or within the particle. In some embodiments, the cosmetic active ingredient is encapsulated by the plurality of pores.

In some embodiments, the MaSp-based fiber is a porous MaSp-based fiber characterized by a BET surface area of at least 10 m$^2$/g, at least 20 m$^2$/g, at least 30 m$^2$/g, at least 40 m$^2$/g, at least 50 m$^2$/g, at least 60 m$^2$/g, at least 70 m$^2$/g, at least 80 m$^2$/g, at least 100 m$^2$/g, at least 130 m$^2$/g, at least 150 m$^2$/g, at least 160 m$^2$/g, at least 170 m$^2$/g, at least 180 m$^2$/g, including any range or value therebetween.

In some embodiments, the porous MaSp-based fiber is characterized by a BET surface area between 10 and 200 m$^2$/g, between 10 and 50 m$^2$/g, between 10 and 20 m$^2$/g, between 20 and 50 m$^2$/g, between 50 and 70 m$^2$/g, between 70 and 100 m$^2$/g, between 100 and 120 m$^2$/g, between 120 and 150 m$^2$/g, between 150 and 170 m$^2$/g, between 170 and 190 m$^2$/g, between 150 and 190 m$^2$/g, between 160 and 190 m$^2$/g, between 170 and 190 m$^2$/g, between 100 and 190 m$^2$/g, between 180 and 190 m$^2$/g, between 170 and 180 m$^2$/g, between 180 and 200 m$^2$/g, between 190 and 200 m$^2$/g, including any range or value therebetween. In some embodiments, the porous MaSp-based fiber is characterized by a BET surface area between 100 and 200 m$^2$/g, between 150 and 200 m$^2$/g, including any range or value therebe-tween.

In some embodiments, the MaSp-based fiber is in a form of a non-porous MaSp-based fiber or a non-porous particle. In some embodiments, the MaSp-based fiber is in a form of an aggregated particle. In some embodiments, the non-porous MaSp-based fiber is characterized by a BET surface area of at most 10 m$^2$/g, at most 8 m$^2$/g, at most 6 m$^2$/g, at most 5 m$^2$/g, at most 3 m$^2$/g, at most 2 m$^2$/g, at most 1 m$^2$/g, at most 0.5 m$^2$/g, at most 0.3 m$^2$/g, at most 0.1 m$^2$/g, including any range or value therebetween. In some embodi-ments, the non-porous MaSp-based fiber or a non-porous particle is characterized by a BET surface area between 0.01 and 1 m$^2$/g.

It should be understood that the particle characterized by a large surface area (e.g. a porous particle) has an increased encapsulation ability, compared to a non-porous particle (e.g. a particle having a BET surface area of less than 10

$m^2/g$). Comparative SEM images of porous or non-aggregated and non-porous or aggregated particles are represented in FIGS. 21A-D.

In some embodiments, the term "porous particle" and the term "non-aggregated particle" are used herein interchangeably. In some embodiments, the term "non-porous particle" and the term "aggregated particle" are used herein interchangeably.

In some embodiments, the porous particle is stable in a dispersion. In some embodiments, porous particles are significantly more stable in a dispersion, compare to non-porous particles. In some embodiments, the dispersion is an aqueous dispersion. In some embodiments, a dry porous particle substantially maintains its size upon redispersion in an aqueous solution. In some embodiments, porous particles are devoid of agglomeration within an aqueous dispersion. In some embodiments, porous particles are devoid of aggregates within an aqueous dispersion.

In some embodiments, non-porous particles are characterized by a particle size of more than 10 μm, more than 20 μm, more than 30 μm, more than 40 μm, more than 50 μm, more than 60 μm, more than 70 μm, more than 80 μm, including any range between. In some embodiments, the particle size is as described herein. In some embodiments, non-porous particles are in a form of aggregates or agglomerates within an aqueous solution. In some embodiments, non-porous particles (e.g. dry non-porous particles) form aggregates upon redispersion in an aqueous solution.

As exemplified herein below (FIG. 12), dry non-porous (or aggregated) particles tend to form aggregates upon redispersion in an aqueous solution. Such aggregates may have a particle size of tens of micrometers (up to 100 μm). Without being bound to any particular theory or mechanism, it is postulated that the exceptional stability of porous particles within a dispersion, may be related to increased interactions with the aqueous solvent due to the increased surface area of the porous particles. One skilled in the art will appreciate, that the stability of porous particles within a dispersion may be advantageous with respect to a shelf-life of the composition, a maximum concentration of the particles within a composition (e.g. aqueous dispersion), and/or with respect to a loading capacity of the composition (e.g. a composition comprising an active substance incorporated within or encapsulated by the plurality of particles). Furthermore, it is postulated that porous particles may be formed exclusively by any one of the bacterial expression systems described herein.

In some embodiments, the porous particles have a size in the range of 0.5 μm to 1.5 μm, 0.7 μm to 1.5 μm, 0.8 μm to 1.5 μm, 0.9 μm to 1.5 μm, 0.5 μm to 1 μm, 0.7 μm to 1 μm, 0.8 μm to 1 μm, 0.9 μm to 1 μm, 0.5 μm to 1.3 μm, 0.5 μm to 1.2 μm, 0.7 μm to 1.3 μm, 0.7 μm to 1.2 μm, or 0.9 μm to 1.2 μm, including any range therebetween. In some embodiments, size or the particle size is as described hereinabove.

Figure 13:
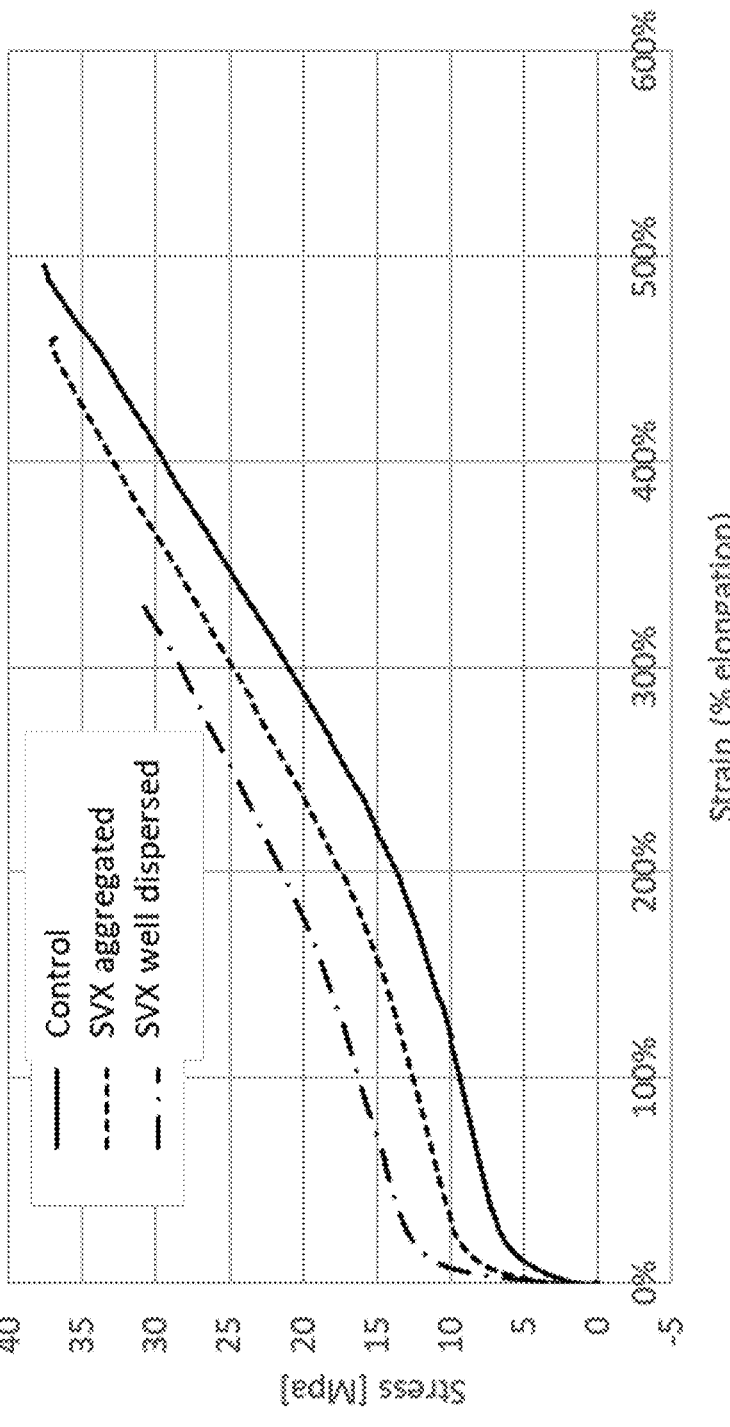
FIG. 13 is a graph showing comparative stress-strain curves of PU samples enriched with 15% w/w of SVX-E. The graph shows stress-strain behavior of PU samples enriched with non-porous or aggregated particles (SVX aggregated), with porous or non-aggregated particles (SVX well dispersed), compared to control PU samples (solid).

In some embodiments, a material (e.g. a polymeric material) enriched with porous particles is characterized by at least one improved mechanical property, compared to the material enriched with non-porous (or aggregated) particles (see FIG. 13). In some embodiments, the mechanical property is as described herein. Without being bound to any particular theory or mechanism, it is postulated that porous particles are advantageous over non-porous particles, with respect to the material enrichment by the MaSp-based fibers (e.g. a polymer enriched with the MaSp-based fiber, as described hereinbelow). It is postulated that the material enriched with porous (or non-aggregated) particles, may have a greater enrichment percentage compared to non-porous (or aggregated) particles, thereby enhancing the reinforcement performance of the MaSp-based fibers.

Encapsulation

In some embodiments, the composition further comprises an additional compound in contact with the MaSp-based polymer or with the MaSp-based fiber. In some embodiments, the additional compound is bound to the MaSp-based polymer or to the MaSp-based fiber. In some embodiments, the composition comprises the additional compound substantially bound to the porous MaSp-based fiber via a non-covalent bond, a physical interaction or both. In some embodiments, the cosmetic active ingredient fills at least a portion of the pores within the matrix or within the particle, wherein the matrix is formed by the intertwisted polymeric chains of the MaSp-based polymer. In some embodiments, the additional compound is encapsulated by the plurality of pores.

In some embodiments, the porous particle is characterized by an increased encapsulation ability, compared to a non-porous particle. In some embodiments, the encapsulation ability is referred to the capability of the particle to incorporate the additional compound. In some embodiments, the increased encapsulation ability is related to a large surface area of the particle, as described hereinabove.

In some embodiments, the additional compound is stably encapsulated within the plurality of pores of the particle. In some embodiments, the encapsulated additional compound is characterized by a gradual release profile (e.g. on the application site, in a solution or in a dispersion). In some embodiments, the particle encapsulating the additional compound substantially prevents a rapid release of the additional compound therefrom.

As used herein, the term "stably encapsulated" refers to the ability of the composition to substantially prevent a release of the active ingredient therefrom (e.g. the additional compound). As used herein, the term "substantially prevent" is referred to a total amount of the active ingredient released from the composition, such as upon subsequent washings (as described in the Examples section).

In some embodiments, substantially comprises at least 50%, at least 60%, at least 70%, at least 75%, at least 80%, at least 85%, at least 90%, at least 95%, at least 97%, at least 99%, by weight of the additional compound. In some embodiments, substantially comprises at least 50%, at least 60%, at least 70%, at least 75%, at least 80%, at least 85%, at least 90%, at least 95%, at least 97%, at least 99%, by weight of additional compound is bound to the MaSp-based fiber via a non-covalent bond, via a physical interaction or both. Non-covalent bonds are well-known in the art and include inter alia hydrogen bonds, p-p stacking, Van der Waals interactions, etc.

In some embodiments, the physical interaction is referred to the encapsulation (i.e. entrapment) of the additional compound within a matrix formed by the MaSp-based polymer. In some embodiments, the matrix is bound or in contact with the additional compound.

In some embodiments, the additional compound is selected from biological agent, a pharmaceutical agent, a nutrient, and a dietary supplement.

The term "biological agent (also designated as biological material)", as used herein, relates to any substance or material having a biological origin. For example, the term "biological agent" covers cells (including stem cells), proteins, peptides, or nucleic acids (including analogs of nucleic acids). The term "pharmaceutical agent (also designated as pharmaceutical compound)", as used herein, refers to any biological or chemical substance, which may be used in the treatment, cure, prophylaxis, prevention, or diagnosis of a pathological condition, e.g. a disease or disorder, or which may be used to otherwise enhance the physical, psychical, or mental well-being. Accordingly, the term "pharmaceutical agent" envisaged in the context of the present invention includes any agent with therapeutic, diagnostic, or prophylactic effects, i.e. any therapeutic agent, diagnostic agent, or prophylactic agent.

The pharmaceutical agent may be an agent that affects or participates in tissue growth, cell growth, cell differentiation, an agent that is able to invoke a biological action such as an immune response, or an agent that can play any other role in one or more biological processes.

Non-limiting examples of pharmaceutical agents include but are not limited to an anti-microbial agent, such as an antibacterial agent (e.g. an antibiotic), an anti-viral agent or an anti-fungal agent, an immunosuppressive agent, an anti-inflammatory agent, an anti-allergic agent, an anti-coagulant, an anti-rheumatic agent, an anti-psoriatic agent, a sedative agent, a muscle relaxant, an anti-migraine agent, an anti-depressant, an insect repellent, a growth factor, a hormone, a hormone antagonist, an antibody, an adjuvant, e.g. in combination with an immunological active compound such as an antibody, an antioxidant, a protein, such as a glycoprotein, lipoprotein, or an enzyme (e.g. hyaluronidases), a polysaccharide, a free radical scavenger, a radiotherapeutic agent, a photodynamic therapy agent, a dye (e.g. fluorescent dye), a contrast agent, a disinfectant, a preservative, or any combination thereof.

The pharmaceutical agent may also be a small molecule compound. The term "small molecule compound" refers to a molecule that can act to affect biological processes. Small molecules can include any number of therapeutic agents presently known and used, or can be small molecules synthesized in a library of such molecules for the purpose of screening for biological function(s). The small molecule compound usually has a molecular weight less than about 5,000 daltons (Da), preferably less than about 2,500 Da, more preferably less than 1,000 Da, most preferably less than about 500 Da.

As used herein, a "nutrient" is a chemical that an organism needs to live and grow or a substance used in an organism's metabolism which must be taken in from its environment. Organic nutrients include carbohydrates, fats, proteins (amino acids), and vitamins. Inorganic nutrients are dietary minerals, water, and oxygen. Preferred nutrients are macronutrients such as carbohydrates, amino acids or proteins and micronutrients such as vitamins.

Non-limiting examples of carbohydrates include but are not limited to monosaccharides such as, glyceraldehyde, erythrose, threose, ribose, arabinose, xylose, lyxose, allose, altrose, glucose, mannose, gulose, idose, galactose, talose, dihydroxacetone, erythrulose, ribulose, xylulose, psicose, fructose, sorbose, tagatose or stereoisomers thereof, amino sugars such as galactosamine, glucosamine, sialic acid, N-acetylglucosamine, sulfo sugars such as sulfoquinovose, disaccharides such as sucrose, lactulose, lactose, maltose, trehalose or maltobiose, and oligosacharides such as Fructooligosaccharides (FOS), Galactooligosaccharides (GOS) or Mannan-oligosaccharides (MOS).

The term "dietary supplement" (also designated as food supplement or nutritional supplement), as used herein, refers to a preparation intended to provide nutrients such as vitamins, minerals, fiber, fatty acids or amino acids, that are missing or are not consumed in sufficient quantity in a person's diet.

Non-limiting examples of dietary supplements include, but are not limited to, steroids such as dehydroepiandrosterone (DHEA), pregnenolone, or derivatives therof, hormones such as melatonin, and other substances such as hydrrazine sulfate, caffeine, catechins, soy isoflavones, glucosamine, coenzyme-$Q_{10}$, or ephedrine-type alkaloids such as ephedrine, synephrine, norephedrine, or pseudodoephedrine.

The active agent may be positively or negatively charged. The active agent may also be electroneutral. Preferably, the active agent is positively or negatively charged. The terms "positive charge" and "cationic" as well as "negative charge" and "anionic" can be used interchangeably.

In some embodiments, a weight per weight (w/w) ratio of the MaSp-based polymer to the additional compound is from 10:1 to 1:10, from 10:1 to 8:1, from 8:1 to 6:1, from 6:1 to 4:1, from 4:1 to 3:1, from 3:1 to 2:1, from 2:1 to 1:1, from 1:1 to 1:2, from 1:2 to 1:3, from 1:3 to 1:5, from 1:5 to 1:10 including any range therebetween.

Polymer Enrichment

In another aspect, there is a composition comprising the MaSp based polymer and an additional polymer. In some embodiments, the additional polymer is in contact with the MaSp-based fiber or with the MaSp-based polymer. In some embodiments, the additional polymer is bound to the MaSp-based fiber or to the MaSp-based polymer.

In some embodiments, the composition comprises the additional polymer bound to the MaSp-based fiber, so as to form a composite. In some embodiments, in contact comprises bound or adhered, wherein bound is as described herein.

In some embodiments, the additional polymer fills 50% to 100% of the volume of the pores. In some embodiments, the additional polymer substantially fills 50% to 100% of the volume of the pores, wherein substantially is as described hereinabove. In some embodiments, the additional polymer fills 55% to 100%, 60% to 100%, 55% to 100%, 70% to 100%, 75% to 100%, 80% to 100%, 85% to 100%, 90% to 100%, 95% to 100%, 50% to 99%, 50% to 98%, 50% to 97%, 50% to 95%, 50% to 90%, 70% to 90%, or 70% to 95% of the volume of the pores, including any range therebetween.

In some embodiments, the composition comprising the MaSp-based polymer of the invention bound to an additional polymer, wherein a w/w ratio of the MaSp-based polymer to the additional polymer is between 1:1 and 1:100, between 1:1 and 1:5, between 1:1 and 1:3, between 1:3 and 1:5, between 1:5 and 1:10, between 1:5 and 1:7, between 1:7 and 1:10, between 1:10 and 1:2, between 1:12 and 1:15, between 1:15 and 1:20, between 1:20 and 1:30, between 1:30 and 1:40, between 1:40 and 1:50, between 1:50 and 1:70, between 1:70 and 1:100, including any range or value therebetween.

In some embodiments, the additional polymer is a synthetic polymer. In some embodiments, the synthetic polymer is selected from, a thermoplastic polymer and a thermoset polymer. Non-limiting examples of synthetic polymers include but are not limited to an epoxy, a polyester, a polyamide, a polyol, a polyurethane, polyethylene, a silicon, liquid crystal polymers, maleic anhydride grafted polypropylene, a polyacrylate, a polycarbonate, polyamides, Nylon 4,6, Nylon 6, Nylon 6,6, Nylon 11, Nylon 12, poly(arylamide), polyethylene, polybutylene terephthalate, polyethylene terephthalate, polyphenylene sulfide, polyphthalamide, polypropylene, poly(vinylidene fluoride), Poly(2-hydroxyethyl methacrylate) (pHEMA), polyurethane, polyvinyl butyral, ethylene vinyl alcohol copolymer, polylactide acid (PLA) or a copolymer thereof, polycaprolactone (PCL), xanthan, cellulose, collagen, elastin, keratin, cotton, rubber, cellulose, wool, and a film forming agent or any combination thereof.

In some embodiments, the additional polymer is the synthetic polymer. In some embodiments, the additional polymer is the film forming agent. In some embodiments, the w/w content of the MaSp-based fiber within the composition is 0.1 and 20%, between 0.1 and 1%, between 1 and 2%, between 2 and 5%, between 5 and 7%, between 4 and 6%, between 6 and 8%, between 8 and 10%, between 10 and 12%, between 12 and 15%, between 15 and 20%, including any range or value therebetween. In some embodiments, the composition comprising more than 20% w/w of the MaSp-based is a non-homogenous composition. In some embodiments, the composition comprising more than 20% w/w of the MaSp-based is characterized by aggregates formation.

In some embodiments, the film-forming agent is selected from a liquid film-forming agent and/or a solid film-forming agent. In some embodiments, the film-forming agent is a solid film-forming agent.

In some embodiments, a w/w concentration of the film forming agent within the composition comprising the film forming agent and the MaSp based fiber is between 20 and 95%, between 20 and 30%, between 30 and 40%, between 40 and 50%, between 50 and 60%, between 60 and 70%, between 70 and 80%, between 80 and 85%, between 85 and 90%, between 90 and 95%, including any range or value therebetween.

Non-limiting examples of film forming agents include but are not limited to polysaccharides, such as pullulan, agave-based polysaccharide (Gosulin Agave®); Intensyl®, Osilift®, Liftonin Xpress®, LiftLiss®, Trik Fision®, polyvinyl alcohol (PVA), polyvinylpyrrolidone (PVP), polyvinyl acetate, polyalkyl acrylate; dextrin, cellulose derivatives such as alkyl cellulose and nitrocellulose, siliconized polysaccharides such as pullulan tri(trimethylsiloxy)silylpropylcarbamate; a polyphenol, a gum, an acrylic-silicone graft copolymer such as alkyl acrylate-dimethicone copolymers, a silicone resin such as trimethylsiloxysilicic acid or fluorine-modified silicone resin, silicone-modified polynorbonene, fluorocarbon resin, aromatic hydrocarbon resin, polymer emulsion resin, terpene resin, polybutene, polyisoprene, alkylated resin, polyvinylpyrrolidone-modified polymer, rosin-modified resin and polyurethane or any combination thereof.

Other non-limiting examples of film forming agents include but are not limited to pullulan tri(trimethylsiloxy) silylpropylcarbamate (e.g. TSPL-30-D5), alkyl acrylate-dimethicone copolymers (e.g. KP-543, 545, 549, 550 and 545 L), trimethylsiloxysilicic acid (e.g. KF-7312) and X-21-5250), and silicone-modified polynorbonene or any combination thereof. In some embodiments, the film-forming agent is at least one of pullulan, Osilift®, agave-based polysaccharide (Gosulin Agave®), and Intensyl® (manioca based polysaccharide).

In some embodiments, the film-forming agent is in a form of a purified compound, a plant extract, at least partially enriched plant extract or any combination thereof. In some embodiments, the film-forming agent at an appropriate concentration within the composition provides pliability thereto. In some embodiments, the film-forming agent at an appropriate concentration enables applying (e.g. by spreading) the composition on the skin of a subject. In some embodiments, the film-forming agent at an appropriate concentration facilitates film forming properties of the composition. In some embodiments, the appropriate concentration of the film-forming agent is as described herein. Exemplary compositions comprising the film-forming agent are provided in the Examples section.

In some embodiments, the composition comprises the MaSp-based polymer bound to the film-forming agent. In some embodiments, a w/w ratio between the film forming agent and said MaSp based fiber within the composition is from 5:1 to 50:1, from 5:1 to 7:1, from 7:1 to 8:1, from 8:1 to 9:1, from 9:1 to 10:1, from 10:1 to 11:1, from 11:1 to 12:1, from 12:1 to 15:1, from 15:1 to 20:1, from 20:1 to 30:1, from 30:1 to 40:1, from 40:1 to 50:1 including any range therebetween. In some embodiments, the composition is in a form of a film. In some embodiments, the composition is pliable. In some embodiments, the composition is capable of forming a film (e.g. a layer) when applied on top of a substrate. In some embodiments, the MaSp-based polymer at an appropriate concentration within the composition enhances the pliability of the composition. In some embodiments, the appropriate concentration of the MaSp-based polymer is as described herein. In some embodiments, the MaSp-based polymer improves at least one mechanical property of the composition comprising the film-forming agent (as exemplified by FIGS. 14). Exemplary compositions comprising the film-forming agent and the MaSp-based polymer are provided in the Examples section.

In some embodiments, the content of the additional polymer is 10% to 99% (w/w), 10% to 90% (w/w), 10% to 80% (w/w), 30% to 99% (w/w), 30% to 98% (w/w), 30% to 95% (w/w), 30% to 90% (w/w), 30% to 85% (w/w), 30% to 80% (w/w), 30% to 75% (w/w), 30% to 70% (w/w), 30% to 65% (w/w), 30% to 50% (w/w), 30% to 45% (w/w), 30% to 40% (w/w), 40% to 70% (w/w), 40% to 65% (w/w), 40% to 50% (w/w), 40% to 45% (w/w), 50% to 70% (w/w), 50% to 80% (w/w), 50% to 90% (w/w), 50% to 95% (w/w), 70% to 80% (w/w), 70% to 90% (w/w), or 70% to 95% (w/w), of the total composition, including any range therebetween.

In some embodiments, the additional polymer according to the present invention is enriched with an insoluble MaSp-based polymer described herein. In some embodiments, the additional polymer is enriched with more than 1% (w/w), more than 2% (w/w), more than 4% (w/w), more than 5% (w/w), more than 10% (w/w), more than 12% (w/w), more than 15% (w/w), more than 20% (w/w), more than 25% (w/w), more than 30% (w/w), more than 40% (w/w), more than 45% (w/w), or more than 50% (w/w), of an insoluble MaSp-based polymer.

In some embodiments, the additional polymer is bound to the MaSp-based fiber via a non-covalent bond, via a physical interaction or both. Non-covalent bonds are well-known in the art and include inter alia hydrogen bonds, p-p stacking, Van der Waals interactions, etc.

In some embodiments, the physical interaction is referred to the additional polymer entangled or intertwined with the MaSp-based fiber, entrapped within a mesh or a matrix formed by the MaSp-based fiber. In some embodiments, the matrix is formed by the cosmetic active ingredient filling at least a portion of the pores within the MaSp-based fibers.

In some embodiments, the composition is a composite, wherein the composite comprises the MaSp based fiber bound to the additional polymer, wherein bound is via a non-covalent bond, a covalent bond, a physical interaction or any combination thereof.

In some embodiments, the additional polymer is in contact with or bound to the fibrils. In some embodiments, the MaSp-based fiber is incorporated within the additional polymer. In some embodiments, the MaSp-based fiber is embedded within the additional polymer. In some embodiments, the additional polymer is doped by the MaSp-based fiber. In some embodiments, the MaSp-based fiber is encapsulated by the additional polymer.

In some embodiments, at least a part of the additional polymer fills 20% to 100% of the volume (e.g. lumen) of the particle. In some embodiments, at least a part of the additional polymer fills 55% to 100%, 60% to 100%, 55% to 100%, 70% to 100%, 75% to 100%, 80% to 100%, 85% to 100%, 90% to 100%, 95% to 100%, 50% to 99%, 50% to 98%, 50% to 97%, 50% to 95%, 50% to 90%, 70% to 90%, or 70% to 95% of the volume of the particle, including any range therebetween.

In some embodiments, the additional polymer is substantially devoid of any additional biologically active ingredient. In some embodiments, the additional polymer is substantially devoid of a protein, such as MaSp-based protein. In some embodiments, the additional polymer of the invention consisting essentially of the polymers listed hereinabove.

In some embodiments, the composition of the invention is substantially homogenous.

In some embodiments, the composition or the composite is a solid. In some embodiments, the composition or the composite is a semisolid. In some embodiments, the composition or the composite is a gel. In some embodiments, composition (e.g. the solid composition) is substantially devoid of any one of a solvent, a surfactant, a carrier, a particle, wherein substantially is at least 80%, at least 90%, at least 92%, at least 95%, at least 97%, at least 98%, at least 99% by weight of the composition.

In some embodiments, the composition is characterized by at least one improved mechanical property as compared to the property for the additional polymer free of the MaSp-based polymer.

In some embodiments, the property is selected from the group consisting of: Young's modulus, tensile strength, fracture strain, yield point, toughness, work to failure, impact strength, tear strength, flexural modulus, flexural strain and stress at a specific percentage elongation, and abrasion. In some embodiments, the mechanical property is selected from storage modulus and loss modulus or any combination thereof.

In some embodiments, the present invention provides an abrasion resistant composition. In some embodiments, the present invention provides a composition with improved abrasion resistance. As used herein, the term "abrasion resistance" refers to the ability of a material to stop the displacement when exposed to a relative movement of the hard particles or projections. Abrasion resistance can be measured through a variety of tests known in the art, such as for example, burned off (Taber) wear test, Gardner scrubber (Gardner scrubber) test, a sand-fall (falling sand) tests.

In some embodiments, one or more properties selected from Young's modulus, tensile strength, yield point, abrasion resistance, and stress at elongation, is enhanced by e.g., at least 1%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, one or more properties selected from Young's modulus, tensile strength, yield point, abrasion resistance, and stress at elongation, is enhanced by e.g., at least 100%, at least 150%, at least 250%, at least 250%, at least 260%, at least 270%, at least 280%, at least 290%, at least 300%, at least 350%, at least 400%, at least 450%, at least 500%, at least 550%, at least 600%, at least 650%, at least 700%, at least 750%, at least 800%, at least 850%, at least 900%, at least 1000%, at least 1500%, at least 2000%, at least 2500%, or at least 3000%.

In some embodiments, the composition is characterized by a Young's modulus in the range of 50 MPa to 170 MPa, 52 MPa to 170 MPa, 60 MPa to 170 MPa, 68 MPa to 170 MPa, 90 MPa to 170 MPa, 100 MPa to 170 MPa, 101 MPa to 170 MPa, 105 MPa to 170 MPa, 101 MPa to 160 MPa, or 105 MPa to 160 MPa, including any range therebetween.

In some embodiments, at least two properties selected from Young's modulus, tensile strength, yield point, abrasion resistance, and stress at elongation, is enhanced by e.g., at least 1%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, at least three properties selected from Young's modulus, tensile strength, yield point, abrasion resistance, and stress at elongation, are enhanced by e.g., at least 1%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, the Young's modulus is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 50%, at least 100%, at least 200%, or at least 500%.

In some embodiments, the tensile strength is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, or at least 50%.

In some embodiments, the yield point is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, or at least 50%.

In some embodiments, the abrasion resistance is enhanced by e.g., at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, or at least 50%.

In some embodiments, the composition is characterized by a structural strength, wherein more than 20% of the structural strength results from the incorporated MaSp-based polymer. In some embodiments, the composite is characterized by a structural strength, wherein more than 30% of the structural strength results from the incorporated MaSp-based polymer.

In some embodiments, the composition is characterized by a structural strength, wherein more than 1% of the tensile strength results from the incorporated MaSp-based polymer. In some embodiments, the composite is characterized by a structural strength, wherein more than 5% of the tensile strength results from the incorporated MaSp-based polymer. In some embodiments, the composite is characterized by a structural strength, wherein more than 10% of the tensile strength results from the incorporated MaSp-based polymer. In some embodiments, the composite is characterized by a structural strength, wherein more than 20% of the tensile strength results from the incorporated MaSp-based polymer. In some embodiments, the composite is characterized by a tensile strength, wherein more than 30% of the structural strength results from the incorporated MaSp-based polymer.

In some embodiments, the phrase "structural strength", as used herein, refers to the mechanical properties such as, without being limited thereto, elastic modulus, tensile stress, elongation (strain) and toughness [e.g., combination of tensile stress and elongation (strain)].

In some embodiments, the MaSp-based polymer improves at least one mechanical property of the composition comprising the film-forming agent, wherein the mechanical property is as described herein. Experimental results of mechanical properties of the exemplary compositions comprising the MaSp-based polymer and the film-forming agent are summarized in FIG. 14.

Production Methods

In some embodiments, there is provided a method for producing the spider silk (MaSp)-based polymer of the invention. In some embodiments, the bacteria used under the composition and/or the method of the invention is a recombinant bacterium. Recombinant bacteria proteins can be created artificially by recombinant DNA technology known in the art.

As used herein, a "recombinant nucleic acid" is a molecule where the nucleic acid molecule which encodes a polypeptide of interest has been modified in vitro, so that its sequence is not naturally occurring, or corresponds to naturally occurring sequences that are not positioned as they would be positioned in a genome which has not been modified.

In one embodiment, a bacterium as described herein is a genetically modified bacterium. In one embodiment, the artificial dragline spider silk is not endogenously produced in a bacterium such as described herein. The artificial dragline spider silk of the invention produced in a bacterium as described herein has unexpected and unique properties.

In some embodiments, the method of the invention comprises the steps of:

a. providing an expression vector comprising a nucleic acid sequence encoding the amino acid sequence, wherein the nucleic acid is under expression control of an operably linked promoter and, optionally, regulatory sequences;

b. transforming a microorganism (e.g. bacterium) host with the expression vector of (a);

c. providing conditions for expression of heterologous proteins by the microorganism of (b); and d. isolating the expressed proteins, thereby obtaining the synthetic amino acid sequences of the invention.

According to some embodiments, there is provided a process (e.g., of fabricating a synthetic dragline spider silk) comprising:

(i) providing the microorganism (e.g. recombinant bacterium) as described herein;

(ii) providing conditions for expression of the MaSp by the microorganism; and (iii) isolating the expressed proteins, thereby fabricating the synthetic dragline spider silk.

In some embodiments, step (ii) of providing condition for expression of MaSp by the bacterium, comprises providing a solution with a pH in the range of 5 to 6.5. In some embodiments, step (ii) comprises providing a solution with a pH lower than 6.5.

In some embodiments, step (ii) of providing condition for expression of MaSp by the bacterium, comprises providing an expression inducer. In some embodiments, the expression inducer comprises lactose. In some embodiments, the expression inducer comprises isopropyl β-D-1-thiogalactopyranoside (IPTG). As used herein, the term "inducer" refers to a compound that induces and/or increases protein expression. In some embodiment, the expression is constitutive expression.

In some embodiments, step (ii) of providing condition for expression of MaSp by the bacterium, comprises waiting during a period of time to obtain an insoluble MaSp-based polymer. In some embodiments, a period of time is in the rage of 15 h to 48 h, 17 h to 48 h, 18 h to 48 h, 18 h to 24 h, 20 h to 48 h, 22 h to 48 h, 24 h to 48 h, 22 h to 36 h, 24 h to 36 h, or 24 h to 32 h, including any range therebetween. In some embodiments, waiting a period of time allows for the formation of synthetic dragline spider silk in two phases. In some embodiments, in a first phase soluble spidroin protein are formed. Once a critical intracellular concentration of the soluble protein has accumulated, self-assembly of the SVX-E takes place, forming the desired insoluble MaSp-based polymer.

In some embodiments, step (iii) of isolating the expressed proteins, comprises the step of solubilizing the bacterium with solution of between 0.1 and 10% of a surfactant, and centrifuging the mixture. In some embodiments, step (iii) of isolating the expressed proteins, comprises the step of solubilizing the bacterium with solution of between 0.1 and 5% of a surfactant, and centrifuging the mixture. In some embodiments, the obtained pellet is suspended in a 6 M Urea solution. In some embodiments, after further centrifugation, the pellet is suspended in 0.07% of a surfactant solution. In some embodiments, after resuspension in the surfactant solution and Urea, the protein is separated from cell debris according to well-known procedure (e.g. by using a 10-90% w/w of a mono-, or a disaccharide solution).

In some embodiments, the process further comprises an enrichment step with an additional polymer and/or with an additional compound. In some embodiments, the additional polymer and the additional compound are as described herein. In some embodiments, the enrichment step comprises mixing a solution of the synthetic dragline spider silk, with solution of the additional polymer.

In some embodiments, the enrichment step comprises degasing the mixture of the solutions comprising synthetic dragline spider silk and an additional polymer.

In some embodiments, degassing is done by letting the obtained suspension to stand at a temperature between 20 and 50° C. without shaking for a certain period of time. In some embodiments, the period of time is in the range of 30 minutes to 24 hours, 1 hour to 24 hours, or 1 hour to 12 hours, including any range therebetween.

In some embodiments, the synthetic dragline spider silk (e.g. MaSp-based polymer or MaSp-based fiber) and the additional polymer are used in a ratio of 1:4 to 4:1, 1:3.9 to 4:1, 1:3.8 to 4:1, 1:3.5 to 4:1, 1:3 to 4:1, 1:2.8 to 4:1, 1:2.5 to 4:1, 1:2 to 4:1, 1.5:4 to 4:1, 1.5:3.9 to 4:1, 1.5:3.8 to 4:1, 1.5:3.5 to 4:1, 1.5:3 to 4:1, 1.5:2.8 to 4:1, 1.5:2.5 to 4:1, 1.5:2 to 4:1, 2:4 to 4:1, 2:3.9 to 4:1, 2:3.8 to 4:1, 2:3.5 to 4:1, 2:3 to 4:1, 2:2.8 to 4:1, 2:2.5 to 4:1, 2:2 to 4:1, 1:4 to 3:1, 1:3.9 to 3:1, 1:3.8 to 3:1, 1:3.5 to 3:1, 1:3 to 3:1, 1:2.8 to 3:1, 1:2.5 to 3:1, 1:2 to 3:1, 1:4 to 4:3, 1:3.9 to 4:3, 1:3.8 to 4:3, 1:3.5 to 4:3, 1:3 to 4:3, 1:2.8 to 4:3, 1:2.5 to 4:3, or 1:2 to 4:3, including any range therebetween.

In some embodiments, the synthetic dragline spider silk (e.g. MaSp-based polymer or MaSp-based fiber) and the additional polymer are used in a ratio of 1:1 and 1:100, between 1:1 and 1:5, between 1:1 and 1:3, between 1:3 and 1:5, between 1:5 and 1:10, between 1:5 and 1:7, between 1:7 and 1:10, between 1:10 and 1:2, between 1:12 and 1:15, between 1:15 and 1:20, between 1:20 and 1:30, between 1:30 and 1:40, between 1:40 and 1:50, between 1:50 and 1:70, between 1:70 and 1:100, including any range therebetween.

In some embodiments, the synthetic dragline spider silk (e.g. MaSp-based polymer or MaSp-based fiber) and the additional compound are used in a ratio from 10:1 to 1:10, from 10:1 to 8:1, from 8:1 to 6:1, from 6:1 to 4:1, from 4:1 to 3:1, from 3:1 to 2:1, from 2:1 to 1:1, from 1:1 to 1:2, from 1:2 to 1:3, from 1:3 to 1:5, from 1:5 to 1:10, including any range therebetween.

In some embodiments, the polymer is selected from a synthetic polymer, a thermoplastic polymer, a thermoset, a film forming agent, an epoxy, a polyester a polyamide, a polyol, a polyurethane, polyethylene, Nylon, a polyacrylate, a polycarbonate, polylactic acid (PLA) or a copolymer thereof a silicon, a liquid crystal polymer, a maleic anhydride grafted polypropylene, polycaprolactone (PCL), rubber, cellulose, or any combination thereof.

In some embodiments, step (iii) further comprises drying of the synthetic dragline spider silk (e.g. SVX-E based fiber). In some embodiments, drying comprises a partial drying of the fiber. In some embodiments, drying is by evaporating of at least 30%, at least 50%, at least 60%, at least 70%, at least 80%, at least 90%, at least 95%, at least 97% per weight of the solvent (e.g. an aqueous solvent). In some embodiments, drying is by exposing the fiber to a temperature between −180 and 200° C. In some embodiments, drying is by exposing the fiber to electromagnetic radiation in a visible and/or infrared-light spectrum.

In some embodiments, drying is by exposing the fiber to a temperature between 40 and 200° C., between 40 and 50° C., between 40 and 60° C., between 60 and 80° C., between 40 and 80° C., between 60 and 100° C., between 100 and 150° C., between 150 and 200° C., including any range or value therebetween.

In some embodiments, drying is by exposing the fiber to microwave radiation. In some embodiments, drying is performed by convection drying, such as by applying a hot gas stream to the fiber. In some embodiments, drying is performed by cold drying, such as by applying a de-humidified gas stream to the fiber. In some embodiments, drying is performed by lyophilization. Generally, the drying method and exact drying conditions selected will depend upon, among other things, chemical and/or physical stability of the fiber (e.g. thermal stability).

MaSp-Based Fibers

The terms "major ampullate spidroin protein" and "spidroin protein" are used interchangeably throughout the description and encompass all known major ampullate spidroin proteins, typically abbreviated "MaSp", or "ADF" in the case of *Araneus diadematus*. These major ampullate spidroin proteins are generally of two types, 1 and 2. These terms furthermore include non-natural proteins, as disclosed herein, with a high degree of identity and/or similarity to at least the repetitive region of the known major ampullate spidroin proteins. Additional suitable spider silk proteins include MaSp2, MiSp, MiSp2, AcSp, FLYS, FLAS, and flagelliform.

As used herein, the term "repetitive region", "repetitive sequence" or "repeat" refer to a recombinant protein sequence derived from repeat units which naturally occur multiple times in spider silk amino acid sequences (e.g., in the MaSp-1 protein). One skilled in the art will appreciate that the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. In some embodiments, the synthetic spider silks of the invention are made wherein the primary structure of the protein comprises a number of exact repetitions of a single unit repeat. In additional embodiments, synthetic spider silks of the invention comprise a number of repetitions of one unit repeat together with a number of repetitions of a second unit repeat. Such a structure would be similar to a typical block copolymer. Unit repeats of several different sequences may also be combined to provide a synthetic spider silk protein having properties suited to a particular application. The term "direct repeat" as used herein is a repeat in tandem (head-to-tail arrangement) with a similar repeat. In another embodiment, the repeat used to form the synthetic spider silk of the invention is a direct repeat. In some embodiments, the repeat is not found in nature (i.e., is not a naturally occurring amino acid sequences).

An exemplary sequence comprising repetitive sequences is ADF-4: AAAAAAASGSGGYG-PENQGPSGPVAYGPGGPVSSAAAAAAAGSGPGGYG-PENQGPS GPGGYGPGGSGSSAAAAAAAAASGPG-GYGPGSQGPSGPGGSGGYGPGSQGPSGPGASS AAAAAAAASGPGGYGPGSQGPSGP-GAYGPGGPGSAAASGPGGYGPGSQGPSGPGGS GGYGPGSQGPSGPGGPGASAAAAAAAAAASGPG-GYGPGSQGPSGPGAYGPGGPGSSAA ASGPG-GYGPGSQGPSGPGAYGPGGPGSSAAAAAAAGSGPG-GYGPGNQGPSGPGGYGP GGPGSSAAAAAAA SGPGGYGPGSQGPGPGVYGPGGPGS-SAAAAAAAGSGPGGYGPG NQGPSGPG-GYGPGGSGSSAAAAAAAASGPG-GYGPGSQGPSGPGGSGGYGPGSQGPSG PGASSAAAAAAAAASGPGGYGPGSQGPSGP-GAYGPGGPGSSAAASGPGGYGPGSQGPS GPGAYGPGGPGSSAAAAAAASGPG-GYGPGSQGPSGPGGSRGYGPGSQGPGGPGASAA AAAAAASGPGGYGPGSQGPSGPGYQGPSGP-GAYGPSPSASAS (SEQ ID NO: 1). In some embodiments, the synthetic repetitive sequence of the invention is based on (e.g., has a high percentage identity, as defined hereinbelow) one or more repetitive sequences derived from ADF-4 (SEQ ID NO: 1). As used herein, the term "based on" refers to a sequence having a high percentage of homology to a repetitive sequence.

In some embodiments, each repetitive sequence comprises up to 60 amino acids, up to 55 amino acids, up to 50 amino acids, up to 49 amino acids, up to 48 amino acids, up to 47 amino acids, up to 46 amino acids, up to 45 amino acids, up to 44 amino acids, up to 43 amino acids, up to 42 amino acids, up to 41 amino acids, up to 40 amino acids, up to 39 amino acids, up to 38 amino acids, up to 37 amino acids, up to 36 amino acids or up to 35 amino acids, wherein possibility represents a separate embodiment of the present invention. In some embodiments, each repetitive sequence comprises 5 to 60 amino acids, 10 to 55 amino acids, 15 to 50 amino acids, 20 to 45 amino acids, 25 to 40 amino acids, acids, 25 to 39 amino acids or 28 to 36 amino acids, wherein possibility represents a separate embodiment of the present invention. In some embodiments, each repetitive sequence comprises 30 to 40 amino acids, 31 to 39 amino acids, 32 to 38 amino acids, 33 to 37 amino acids, 34 to 36 amino acids, wherein each possibility represents a separate embodiment of the present invention. In an additional embodiment, each repetitive sequence comprises 35 amino acids.

In some embodiments, the repetitive region comprises, independently, an amino acid sequence as set forth in Formula 1

$$(X_1)_z X_2 GPGGYGPX_3 X_4 X_5 GPX_6 GX_7 GGX_8 GPGGPGX_9 X_{10};$$

wherein $X_1$ is, independently, at each instance A or G.

In some embodiments, at least 50% of $(X_1)_z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G.

In another embodiment, the repetitive region of a MaSP1 protein comprises the amino acid sequence as set forth in SEQ ID NO: 2 (SGPGGYGPGSQGPSGPG-GYGPGGPGSS). In another embodiment, the repetitive region of a MaSP1 protein comprises the amino acid sequence as set forth in SEQ ID NO: 3 (AAAAAAAASGPGGYGPGSQGPSGPG-GYGPGGPGSS).

In another embodiment, there is provided a homolog of the repetitive region of a MaSP1 protein sharing at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 1.

In another embodiment, the homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 2.

In another embodiment, the repetitive region of a MaSP1 protein has the amino acid sequence as set forth in SEQ ID NO: 1.

In another embodiment, the MaSP1 protein comprises a single N-terminal region selected from the group consisting of: SEQ ID NO: 4 (MSYYHHHHHHDYDIPTTEN-LYFQGAMDPEFKGLRRRAQLV); SEQ ID NO: 5 (MSYYHHHHHHDYDIPTTENLYFQGAMDPE-FKGLRRRAQLVRPLSNLDNAP); SEQ ID NO: 6 (MSYYHHHHHHDYDIPTTENLYFQGAMDPE-FKGLRRRAQLVDPPGCRNSARAGSS), or any functional homolog, variant, derivative, or fragment thereof. In another embodiment, the homolog of the C-terminal region shares at least 70% homology with any one of SEQ ID NOs: 4-6.

In another embodiment, the MaSP1 protein further comprises a single C-terminal region selected from the group consisting of: SEQ ID NO: 7 (VAASRLSSPAASSRVS-SAVSSLVSSGPTNGAAVSGALNSLVSQ-ISASNPGLSGCDALVQ ALLELVSALVAILSSAS-IGQVNVSSVSQSTQMISQALS); and SEQ ID NO: 8 (GPSGPGAYGPSPSASASVAASRLSSPAASSRVS-SAVSSLVSSGPTNGAAVSGALNSLVS QISASNPGLSGCDALVQALLELVSALVAILSSAS-IGQVNVSSVSQSTQMISQALS), or any functional homolog, variant, derivative, fragment or mutant thereof. In another embodiment, the homolog of the N-terminal region shares at least 70% homology with SEQ ID NO: 7-8.

In some embodiments, the MaSp-based fibers comprising a mixture of proteins, as disclosed under WO2017025964, which is incorporated herein by reference in its entirety.

In some embodiments, the MaSP1 protein further comprises at least one tag sequence. Non-limiting examples of tags which may be used in the present invention include a His tag, a HA tag, a T7 tag, and the like. The skilled person is well aware of alternative suitable tags or other fusion partners.

"Amino acid" as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Amino acid sequence" or "peptide sequence" is the order in which amino acid residues, connected by peptide bonds, lie in the chain in peptides and proteins. The sequence is generally reported from the N-terminal end containing free amino group to the C-terminal end containing free carboxyl group Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, sulfhydryl bond formation, cleavage and the likes.

As used herein, "isolated" or "substantially purified", in the context of synthetic spider silk amino-acid sequences or nucleic acid molecules encoding the same, as exemplified by the invention, means the amino-acid sequences or polynucleotides have been removed from their natural milieu or have been altered from their natural state. As such "isolated" does not necessarily reflect the extent to which the amino-acid sequences or nucleic acid molecules have been purified. However, it will be understood that such molecules that have been purified to some degree are "isolated". If the molecules do not exist in a natural milieu, i.e. it does not exist in nature, the molecule is "isolated" regardless of where it is present. By way of example, amino-acid sequences or polynucleotides that do not naturally exist in humans are "isolated" even when they are present in humans.

The term "isolated" or "substantially purified", when applied to an amino acid sequence or nucleic acid, denotes that the amino acid sequence or nucleic acid is essentially free of other cellular components with which they are associated in the natural state. It may be in a homogeneous state, or alternatively in either a dry or aqueous solution. Purity and homogeneity are typically determined using analytical chemistry techniques such as polyacrylamide gel electrophoresis or high-performance liquid chromatography. An amino acid sequence or nucleic acid which is the predominant species present in a preparation is substantially purified.

In some embodiments, the repeats are of a homolog, variant, derivative of a repetitive region of a MaSp1 protein or fragment thereof. In some embodiments, the repeats are of a homolog, variant, derivative of a repetitive region of an ADF-4 protein or fragment thereof.

As used herein, the term "functional" as in "functional homolog, variant, derivative or fragment", refers to an amino acid sequence which possesses biological function or activity that is identified through a defined functional assay. More specifically, the defined functional assay is the formation of self-assembling fibers in cells expressing the functional homolog, variant, derivative or fragment.

An amino acid sequence or a nucleic acid sequence is the to be a homolog of a corresponding amino acid sequence or a nucleic acid, when the homology is determined to be at least 50%, at least 55%, at least 60%, at least 65%, at least 70%, at least 75%, at least 80%, at least 85%, at least 90%, at least 92%, at least 94%, at least 96%, at least 98% or at least 99%.

The terms "identical", "substantial identity", "substantial homology" or percent "identity", in the context of two or more amino acids or nucleic acids sequences, refer to two or more sequences or subsequences that are the same or have a specified percentage of amino acid residues or nucleotides that are the same (i.e., about 60% identity, or at least 65%, at least 70%, at least 75%, at least 80%, at least 85%, at least 90%, at least 91%, at least 92%, at least 93%, at least 94%, at least 95%, at least 96%, at least 97%, at least 98%, or 99% identity over a specified region (e.g., amino acid sequence SEQ ID NO: 2 or 3), when compared and aligned for maximum correspondence over a comparison window or designated region) as measured using a BLAST or BLAST 2.0 sequence comparison algorithms with default parameters described below, or by manual alignment and visual inspection. Such sequences are then to be "substantially identical". This definition also refers to, or may be applied to, the compliment of a test sequence. The definition also includes sequences that have deletions and/or additions, as well as those that have substitutions. The preferred algorithms can account for gaps and the like.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

It should be appreciated that the invention further encompasses amino acid sequence comprising n repeats of a variant of any one of SEQ ID NO: 1, 2, or 3. As used herein, the term "variant" or "substantially similar" comprises sequences of amino acids or nucleotides different from the specifically identified sequences, in which one or more (e.g., 1, 2, 3, 4, 5, 6, 7, 8, 9, 10, 20 or 25) amino acid residues or nucleotides are deleted, substituted or added. The variants may be allelic variants occurring naturally or variants of non-natural origin. The variant or substantially similar sequences refer to fragments of amino acid sequences or nucleic acids that may be characterized by the percentage of the identity of their amino acid or nucleotide sequences with the amino acid or nucleotide sequences described herein, as determined by common algorithms used in the state-of-the-art. The preferred fragments of amino acids or nucleic acids are those having a sequence of amino acids or nucleotides with at least around 40 or 45% of sequence identity, preferentially around 50% or 55% of sequence identity, more preferentially around 60% or 65% of sequence identity, more preferentially around 70% or 75% of sequence identity, more preferentially around 80% or 85% of sequence identity, yet more preferentially around 90%, 91%, 92%, 93%, 94%, 95%, 96%, 97%, 98% or 99% of sequence identity when compared to the sequence of reference.

The terms derivatives and functional derivatives as used herein mean the amino acid sequence of the invention with any insertions, deletions, substitutions and modifications.

It should be appreciated that by the term "insertions", as used herein it is meant any addition of amino acid residues to the sequence of the invention, of between 1 to 50 amino acid residues, specifically, between 20 to 1 amino acid residues, and more specifically, between 1 to 10 amino acid residues. Most specifically, 1, 2, 3, 4, 5, 6, 7, 8, 9 and 10 amino acid residues. Further, the amino acid sequence of the invention may be extended at the N-terminus and/or C-terminus thereof with various identical or different amino acid residues.

Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

In another embodiment, the repeat sequence of the invention has 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions to the sequence of any one of SEQ ID NO: 2 or 3. In one embodiment, the repeat sequence of the invention has at least 2, at least 3, at least 4, at least 5, at least 6, at least 7, at least 8, at least 9, at least 10, at least 11, at least 12, or at least 13 amino acid substitutions to the sequence of any one of SEQ ID NO: 1, 2 or 3.

With respect to amino acid sequences, one of skill will recognize that individual substitutions, deletions or additions to an amino acid, nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Conservative nucleic acid substitutions are nucleic acid substitutions resulting in conservative amino acid substitutions as defined above.

Variants of the amino acid sequences of the invention may have at least 80% sequence similarity, at least 85% sequence similarity, 90% sequence similarity, or at least 95%, 96%, 97%, 98%, or 99% sequence similarity at the amino acid level, with a repeating unit denoted by aby one of SEQ ID NO: 1, 2 or 3.

The amino acid sequence of the invention may comprise a fragment of SEQ ID NO. 1. A "fragment" constitutes a fraction of the amino acid or DNA sequence of a particular region. An amino acid fragment may comprise at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 24, at least 26, at least 27, at least 28, at least 29, at least 30, at least 31, at least 32, at least 33 or at least 34 amino acids of SEQ ID NO: 1, 2 or 3.

Mutants of the amino acid sequences of the invention are characterized in the exchange of one (point mutant) or more, about up to 10, of its amino acids against one or more of another amino acid. They are the consequence of the corresponding mutations at the DNA level leading to different codons.

Still further, the invention concerns derivatives of the amino acid sequence of the invention. Derivatives of the amino acid sequences of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol. Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

It is appreciated that while the invention generally relates to synthetic spider silk proteins or any fragments or parts thereof derived from *Araneus diadematus* dragline silk, many other spider species may be used to derive synthetic spider silk in a similar manner. More preferably, the dragline proteins are derived from one or more of the following spiders: *Arachnura higginsi, Araneus circulissparsus, Ara-*

*neus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis*(elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat *Anepsion* (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island *Cyclosa* Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied *Cyclosa* Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet *Acusilas* (*Acusilas coccineus*), Silver *Argiope* (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), *Nephila* species, e.g. *Nephila clavipes, Nephila senegalensis, Nephila madagascariensis* and many more.

Furthermore, the synthetic spider silk may be enhanced not only by selection of a different spider species to be derived from, but also by the use of various compounds other than protein. Pyrrolidine has hygroscopic properties and helps to keep the thread moist. It occurs in especially high concentration in glue threads. Potassium hydrogen phosphate releases protons in aqueous solution, resulting in a pH of about 4, making the silk acidic and thus protecting it from fungi and bacteria that would otherwise digest the protein. Potassium nitrate is believed to prevent the protein from denaturing in the acidic milieu.

In some embodiments, the bacterial systems of the present invention may utilize a number of expression vectors that are advantageously selected depending upon the use intended for the proteins expressed. In one embodiment, large quantities of proteins are desired. In one embodiment, vectors that direct the expression of high levels of the protein product, possibly as a fusion with a hydrophobic signal sequence, which directs the expressed product into the periplasm of the bacteria or the culture medium where the proteins product is readily purified are desired. In one embodiment, certain fusion protein engineered with a specific cleavage site to aid in recovery of the polypeptide. In one embodiment, vectors adaptable to such manipulation include, but are not limited to, the pET series expression vectors.

"Nucleic acid" refers to a molecule which can be single stranded or double stranded, composed of monomers (nucleotides) containing a sugar, phosphate and either a purine or pyrimidine. In bacteria, "deoxyribonucleic acid" (DNA) refers to the genetic material while "ribonucleic acid" (RNA) is involved in the translation of the information from DNA into proteins.

Due to the degenerative nature of the genetic code it is clear that a plurality of different nucleic acid sequences can be used to code for the amino acid sequences of the invention. It should be appreciated that the codons comprised in the nucleic acid sequence of the invention may be optimized for expression in a bacterium host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Within the context of the present invention, genes and DNA coding regions are codon-optimized for optimal expression in host bacterial cells.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

In some embodiments, the invention relates to one or more expression vectors comprising a nucleic acid sequence encoding the proteins of the invention.

As used herein, a "vector", "expression vector" or "plasmid" as referred to herein is an extra-chromosomal element often carrying exogenous gene/s which is/are not part of the central metabolism of the bacterial cell, and usually in the form of circular double-stranded DNA molecules. It may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. As used herein, "transformation" or "transfection" is the acquisition of new genes in a cell by the incorporation of nucleic acid. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined, namely, the expression of the synthetic spider silk proteins.

As indicated above, the expression vector of the invention is operably linked to a promoter. The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene. The term "suitable promoter" will refer to any prokaryotic promoter capable of driving the expression of a synthetic spider silk variant gene.

Promoters which are useful to drive expression of heterologous DNA fragments in the bacterium are numerous and familiar to those skilled in the art. Virtually any bacterial promoter capable of driving the gene encoding a silk variant protein is suitable for the present invention.

A coding sequence and regulatory sequences are the to be "operably linked" or "operably joined" when they are covalently linked in such a way as to place the expression or transcription of the coding sequence under the influence or control of the regulatory sequences. If the regulatory sequence is positioned relative to the gene such that the regulatory sequence is able to exert a measurable effect on the amount of gene product produced, then the regulatory sequence is operably linked to the gene. If it is desired that the coding sequences be translated into a functional protein, two DNA sequences are the to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence. Especially, such 5' non-transcribing regulatory sequences will include a promoter region which includes a promoter sequence for transcriptional control of the operably joined gene. Regulatory sequences may also include enhancer sequences or upstream activator sequences, as desired.

"Regulation" and "regulate" refer to the modulation of gene expression controlled by DNA sequence elements located primarily, but not exclusively upstream of (5' to) the transcription start of a gene. Regulation may result in an all or none response to stimulation, or it may result in variations in the level of gene expression.

In a further aspect, the invention provides a host cell transformed with the expression vector according to the invention.

"Cells", "host cells" or "recombinant host cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

"Host cell" as used herein refers to cells which can be recombinantly transformed with naked DNA or expression vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

The host cells of the invention are transformed or transfected with the expression vector descried herein to express the synthetic spider silk protein of the invention. "Transformation", as used herein, refers to a process in which a cell's genotype is changed as a result of the cellular uptake of exogenous DNA or RNA, and, for example, the transformed cell expresses a recombinant form of the desired synthetic spider silk protein. The term "transfection" means the introduction of a nucleic acid, e.g., naked DNA or an expression vector, into a recipient cells by nucleic acid-mediated gene transfer.

In some embodiments, the spider silk protein of the invention is devoid of post translational modifications.

According to some aspects, the invention provides an expression vector comprising the nucleic acid sequence of the present invention, wherein the nucleic acid sequence is under expression control of an operably linked promoter and, optionally, regulatory sequences.

General

As used herein the term "about" refers to ±10%.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments. The word "optionally" is used herein to mean "is provided in some embodiments and not provided in other embodiments". Any particular embodiment of the invention may include a plurality of "optional" features unless such features conflict.

As used herein and in the appended claims, the singular forms "a," "and," and "the" include plural referents unless the context clearly dictates otherwise. Thus, for example, reference to "MaSp" includes a plurality of such genes and variants and reference to "the peptide" includes reference to one or more peptides known to those skilled in the art, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

EXAMPLES

Experimental Procedures

Synthesis of a Sequence Encoding for a Single Repeat Unit of a Dragline Spider Silk Protein: A 35 amino acid long sequence representing an average consensus sequence of the 15 repeats constituting the repetitive region of (MaSp)-based polymer (Genbank entry U47856) was designed. The average consensus sequence peptide sequence is: SGPG-GYGPGSQGPSGPGGYGPGGPGSSAAAAAAAA (SEQ ID NO: 11), which is encoded by the 105 DNA base pair sequence: 5'-TCTGGTCCTGGAGGTTATGGCCCAG-GAAGCCAAGGACCATCTGGTCCAGGAGGAT ATGGTCCAGGCGGACCTGGCTCTAGTGCAGCAGCT GCCGCAGCAGCTGCA-3' (SEQ ID NO: 9). The above synthetic DNA was obtained in a pPCR-ScriptAmpSK(+) plasmid.

Bacterial Growth

The pET24R-expressing bacteria were seeded into 3 mL starter of LB medium with chloramphenicol and kanamycin, grew until the OD~0.6 (measured in 100 μL in the 96-well plate), and seeded into a growth medium.

The bacteria was grown at 37° C. under shaking, the OD600 and beta sheet specific staining was performed after ~20 h. Significant beta sheet staining appeared after 24 h.

Lysis and Purification

The bacteria were centrifuged and re-suspended in deionized water. Then, a solution of a surfactant was added and the resulting suspension was shaken overnight at 37° C. After centrifugation, the pellet was re-suspended in 6 M Urea. After the centrifugation, the pellet were re-suspended and washed several times with a surfactant solution.

For quantification, 1 mL of a polymer suspension was washed with deionized water, and dried on a microscope glass. The glass was weighed before and after the application of the (MaSp)-based polymer, the residual was calculated.

UV Spectroscopy

Spider silk (MaSp)-based polymer expressed in bacteria SVXE was dissolved by heating in 8 M LiBr, diluted 1:10 with 6 M Urea, and the UV spectrum was measured in Ultrospec 2100 spectrophotometer at 240-350 nm in disposable UV cuvettes. The 8 M LiBr, diluted 1:10 with 6 M Urea, was used as a control.

Staining

The beta sheet specific stain was dissolved at 0.8 mg/mL in dimethyl sulfoxide (DMSO) and stored at room temperature protected from light. To the E. coli suspension in the medium, 1-30% Triton X-100 was added, and the bacteria were centrifuged. The bacterial pellet was re-suspended in PBS, and 1-50 μL/mL of beta sheet specific stain was added. The suspension was incubated for 30 min at room temperature, then centrifuged, and the bacterial pellet was re-suspended in the same volume of PBS. If necessary, the stained pellet was stored at 4° C. The fluorescence was read in the 96-well plate in Cytation fluorimeter. In parallel, the OD600 was measured, and the fluorescence was normalized to the OD600 values. For staining the final preparation of SVX-E, the MaSp-based polymer were re-suspended in PBS. The rest of the procedure was the same as for staining the bacteria.

Differential Scanning Calorimetry (DSC)

A sample of SVX-E or Sf9-derived SVX was washed with water of the remaining surfactant, the suspension was dried. About 5 mg were weighed in the capsule, and scanning calorimetry was performed in the range 25-300° C., with the speed 10°/min, on Star calorimeter (Mettler Toledo). In parallel, the sample of SVX-E was dissolved in 6 M Guanidine thiocyanate, dialyzed into 6 M urea, and then into deionized water (in water, it partially precipitated). The denatured protein was dried, and the scanning calorimetry was performed according to the same conditions.

TEM

The Spider silk fibers SVX or Spider silk polymers expressed in bacteria SVX-E suspension was deposited on carbon-coated copper grids, and left for 5 min. The grids were washed with distilled water and stained with 2% (w/v) uranyl acetate for another 2 min. The analysis was performed in TEM 120 KeV.

SEM

Scanning electron microscopy (SEM) of various samples was performed according to a standard protocol.

Dynamic Light Scattering (DLS)

The SVX or SVX-E suspensions were diluted 1:100 with 0.07% surfactant solution that was filtered through 0.22 μm filter. The DLS analysis was performed using a Malvern Zetasizer Nano device.

Mass-Spectrometry Analysis

The SVX or SVX-E suspensions were precipitated by centrifugation, dissolved with 6 M Guanidine thiocyanate, and dialyzed into two changes of 6 M Urea. For analysis, the samples were diluted 1:10 (final urea concentration 0.6 M), the possible disulfide bonds were reduced with DTT and blocked with iodo-acetamide, and the protein in two separate tubes was cleaved either with trypsin or with chemotrypsin.

The sequence of the resulting peptides was analyzed by Q Exactive mass spectrograph, and the sequences were analyzed versus the expected sequence of SVX and the database of baculovirus proteins and Spodoptera frugiperda (sf9 source) for SVX, and the database of E coli proteins for SVX-E.

Amino Acid Analysis

For Amino acid analysis, the SVX or SVXE sample was hydrolysed with 6 M HCl for 18-24 h at 110° C.

FTIR

The SVX or SVX-E samples were dried on microscope slides at 100° C., and IR spectrum of the dried material was measured using Nicolet iS5 FTIR Spectrometer (Thermo Fisher Scientific). The Amide I and Amide II peaks were used as markers of the presence of protein, and the exact location of the Amide I peak was used for the evaluation of the secondary structure. The peak location at 1610-1630 cm$^{-1}$ is characteristic foe amyloid-like β-sheets.

Generic Protocol for Enrichment of Polyurethane with Spider Silk Polymer

1. Dispersion in an organic solvent: differential amount (Table 1) of spider silk polymer in an aqueous suspension were centrifuged and re-suspended in DDW (Double distilled water). The suspension was allowed to stabilize for 3 minutes. Then it was centrifuged and re-suspended in ethanol Then it was centrifuged and re-suspended in a sufficient amount of a dry ether-based solvent) twice (the suspension was allowed to stabilize). Then the suspension was filtered through a 40 μm filter. Then it was centrifuged and re-suspended in dry ether-based solvent. The suspension was placed on a rotary shaker at for 10-200 minutes (at R.T.).

In the case of cellulose, powder cellulose was dispersed directly in a sufficient amount of ether-based solvent without prior centrifugation and resuspension in water and ethanol steps.

2. Solubilization of polymer: differential amount (Table 1) of polyurethane was dissolved in a sufficient amount of ether-based solvent in a transparent glass vial with a cork screw (shaker: 37° C., 200 rpm, 1-24 hours).

3. Mixing spider silk suspension with polymer solution: The spider silk polymer suspension was centrifuged and re-suspended in a sufficient amount of ether-based solvent. Then sonicated in a sonicator. The size, breaking and aggregation state of the spider silk polymer suspension was tested using a light microscope. The suspension was poured into the polymer solution. The polymer and spider silk polymer suspension was mixed thoroughly until homogeneity was achieved, then placed in a rotary shaker (R.T., 50 rpm) for 60 minutes.

4. Degassing: The suspension was allowed to stand at 20-60° C. without shaking for 0.5-5 hours (degassing).

In case any bubbles were visible longer degassing continued overnight in a closed vessel.

5. Casting: The size, breaking and aggregation state of the spider silk polymer suspension was tested using a light microscope. The content of the flask was fully casted (18.2 g) in a 9 cm diameter glass petri dish for 14 hours. The petri dish was covered with cardboard and placed under a plastic box in a hood. Then the enriched polyurethane sheet was extracted from the petri dish and placed under vacuum at 80° C. for 90 minutes. The enriched polyurethane sheet was kept at R.T., for 2 days, then cut into 60×7 mm strips.

6. Mechanical properties measurements: The composite materials were analyzed in Lloyd LS5 universal testing machine. The strips pulled at tension rate (mm/min) at 50 mm/min. 50N load cell was used for accurate young's modulus evaluation and 5 kN load cell was used for elongation and (ultimate tensile strength) UTS.

TABLE 1

| | Dispersed SS type | Amount dispersed | Polyurethane: P490RSJT (TOSOH) |
|---|---|---|---|
| 5% | SVX-E | 50 mg in 10 ml ether based solvent | 950 mg in 9 ml ether based solvent |
| 10% | SVX-E | 100 mg in 10 ml ether based solvent | 900 mg in 9 ml ether based solvent |
| 20% | SVX-E, SVX, SVX homogenized | 200 mg in 10 ml ether based solvent | 800 mg in 9 ml ether based solvent |
| 30% | SVX-E | 300 mg in 10 ml ether based solvent | 700 mg in 9 ml ether based solvent |
| 20% | Cellulose (Sigma C6288) | 200 mg in 5 ml ether based solvent | |

| | Dispersed | | Polyurethane: E394POTA (TOSOH) |
|---|---|---|---|
| 10% | SVX-E | 50 mg in 10 ml ether based solvent | 900 mg in 9 ml ether based solvent |
| 20% | SVX-E, SVX, SVX homogenized | 100 mg in 10 ml ether based solvent | 800 mg in 9 ml ether based solvent |
| 30% | SVX-E | 300 mg in 10 ml ether based solvent | 700 mg in 9 ml ether based solvent |

| | Dispersed | | Polyurethane: PE399 (KRYSTALFLEX) |
|---|---|---|---|
| 5% | SVX-E purified, SVX-E non-purified, SVX. SVX homogenized | 50 mg in 5 ml ether based solvent | 950 mg in 10 gr ether based solvent |
| 10% | SVX-E purified, SVX-E non-purified, SVX. SVX homogenized | 100 mg in 5 ml ether based solvent | 900 mg in 10 gr ether based solvent |

SVX-Spider silk fibers; SVX-E-Spider silk polymers expressed in bacteria.

Protocol for Dissolution Profiles of SVX and SVX-E in Various Denaturing Agents

Stock solutions of 8 M Guanidine thiocyanate, 7.5 M Guanidine hydrochloride, and 6 M Urea were prepared in DDW, and different concentrations of the appropriate compounds were dispersed in 80 μL volume in the 96-well plate. 20 μL of SVX (6.3 mg/mL) or SVXE (10 mg/mL) were added, mixed well, and the OD600 was measured in each well. The results were not different, if the same wells were measured repeatedly after 2 h or overnight.

Example 1

Protein Expression in Bacteria

The bacteria express Lysozyme that destroys the cell wall. Bacteria expressing only Lysozyme were used as a control. The medium pH is 5.8.

Staining of β-sheets was used for tracking the formation of insoluble polymer. After purification, the resulting product is a protein. The average yield (before optimization) is 105 mg/L medium.

Figure 1A:
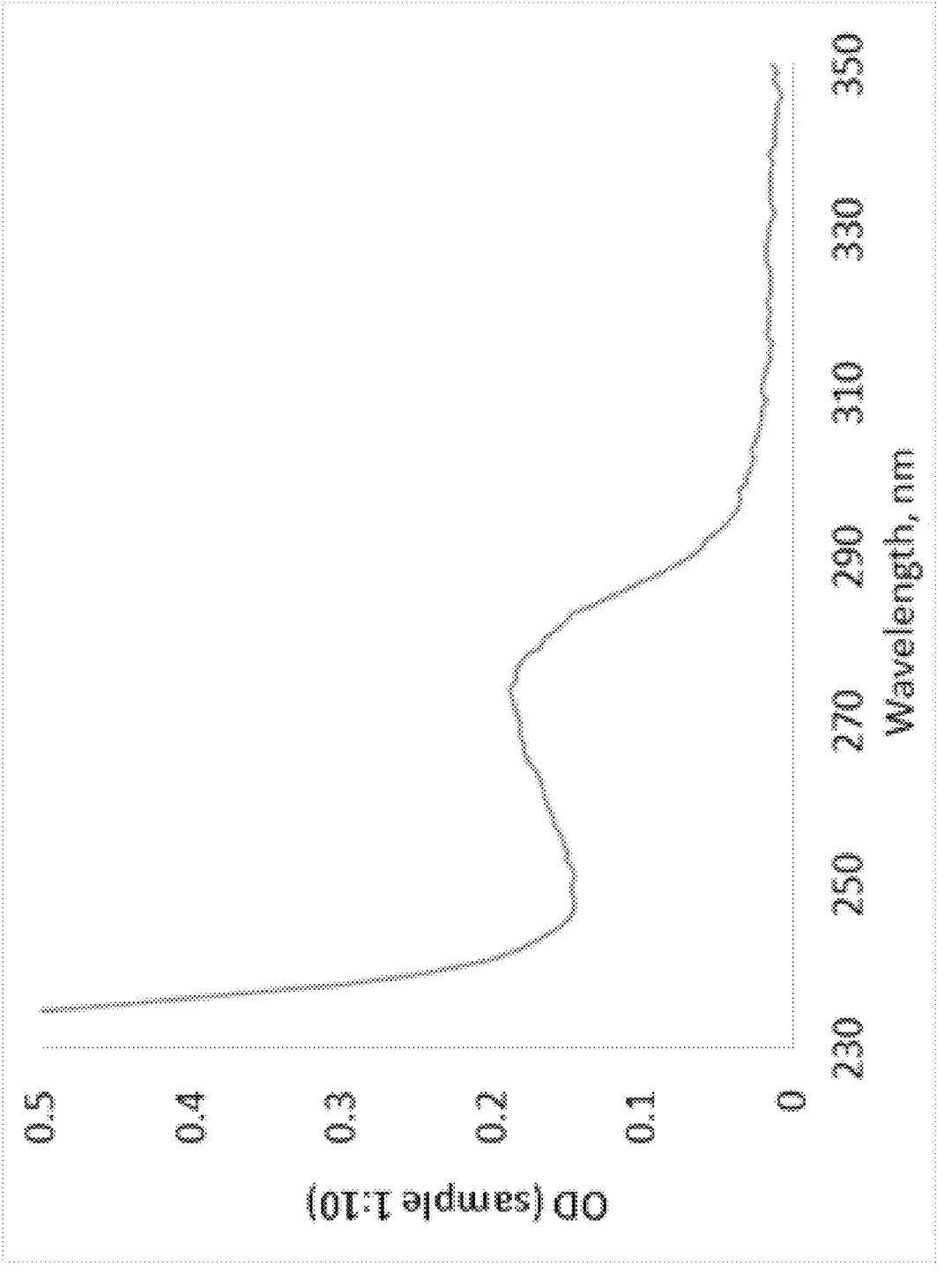
FIGS. 1A-C are UV spectrum of the resulting protein (FIG. 1A), a graph displaying the measured amino acid content vs expected (FIG. 1B) and Fourier-transform infrared spectroscopy (FTIR) spectrum of the resulting protein (SVX-E) (FIG. 1C).

After solubilization in 6 M GuaSCN and dialysis to urea, the UV spectrum is characteristic to tyrosine-containing protein, with maximum at 276 nm (FIG. 1A).

Figure 1B:
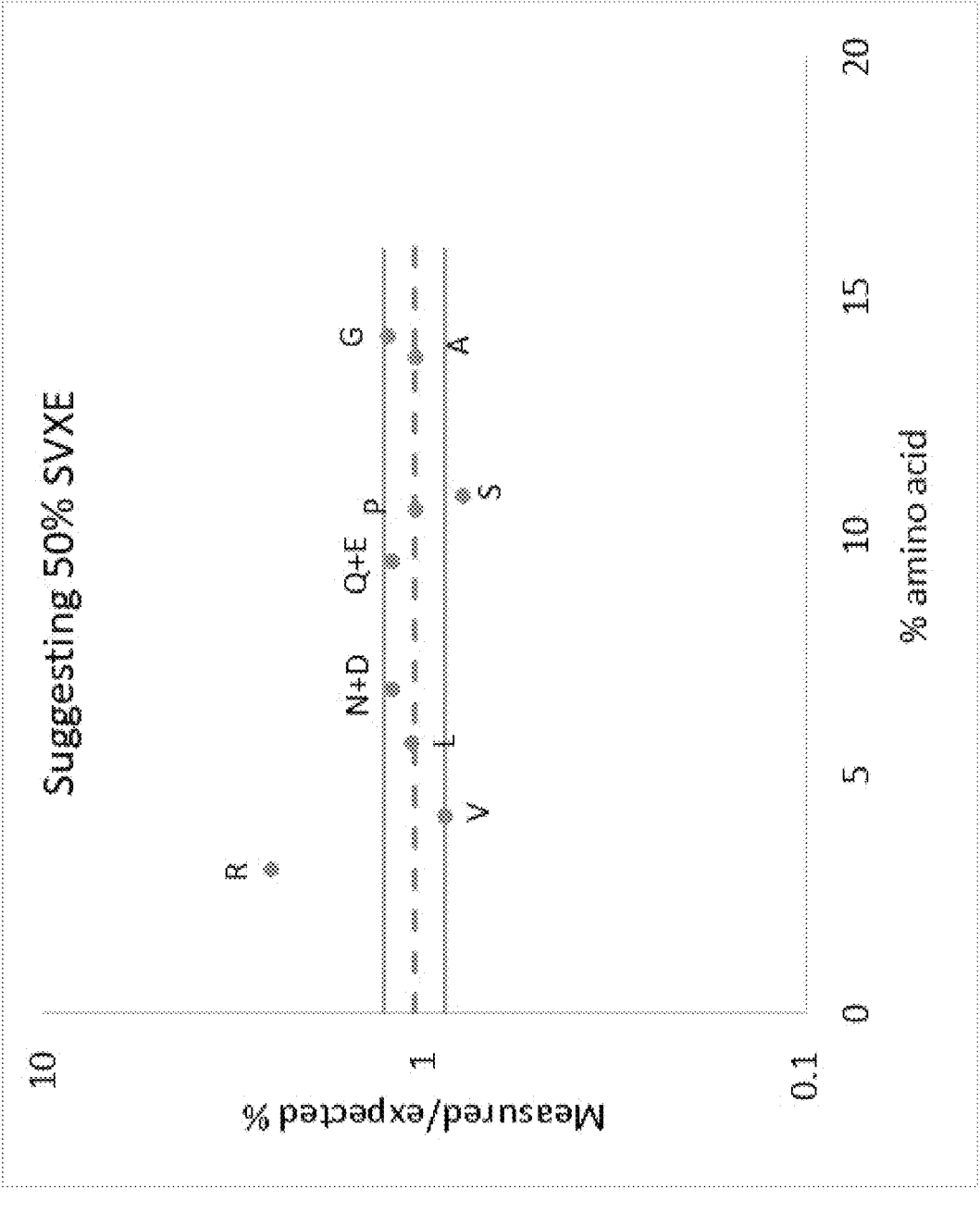

The amino acid content corresponds to the expected sequence (FIG. 1B).

Figure 1C:
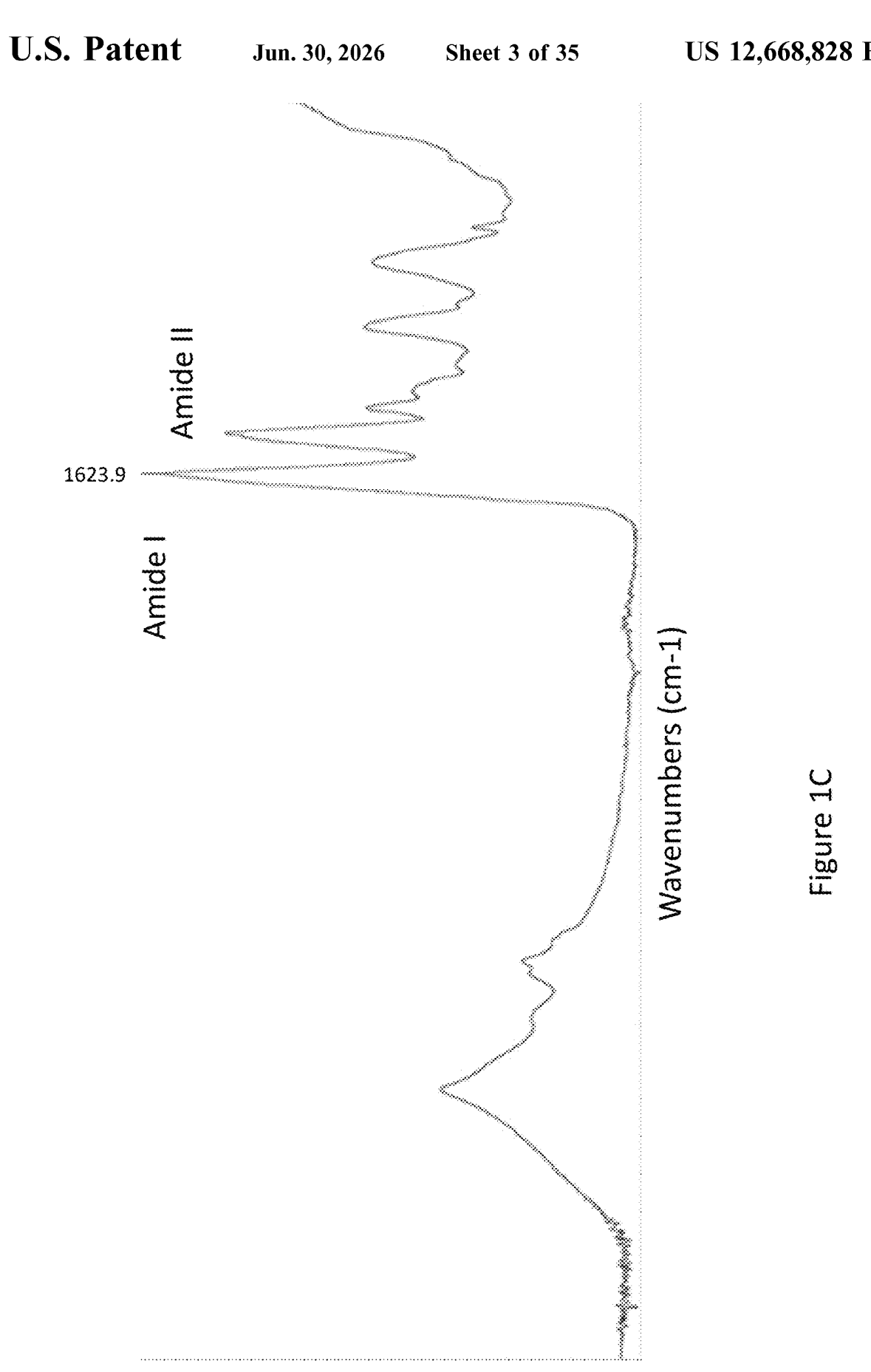

The FTIR spectrum shows the characteristic peaks of amide bond: Amide I and Amide II (FIG. 1C).

Figure 2:
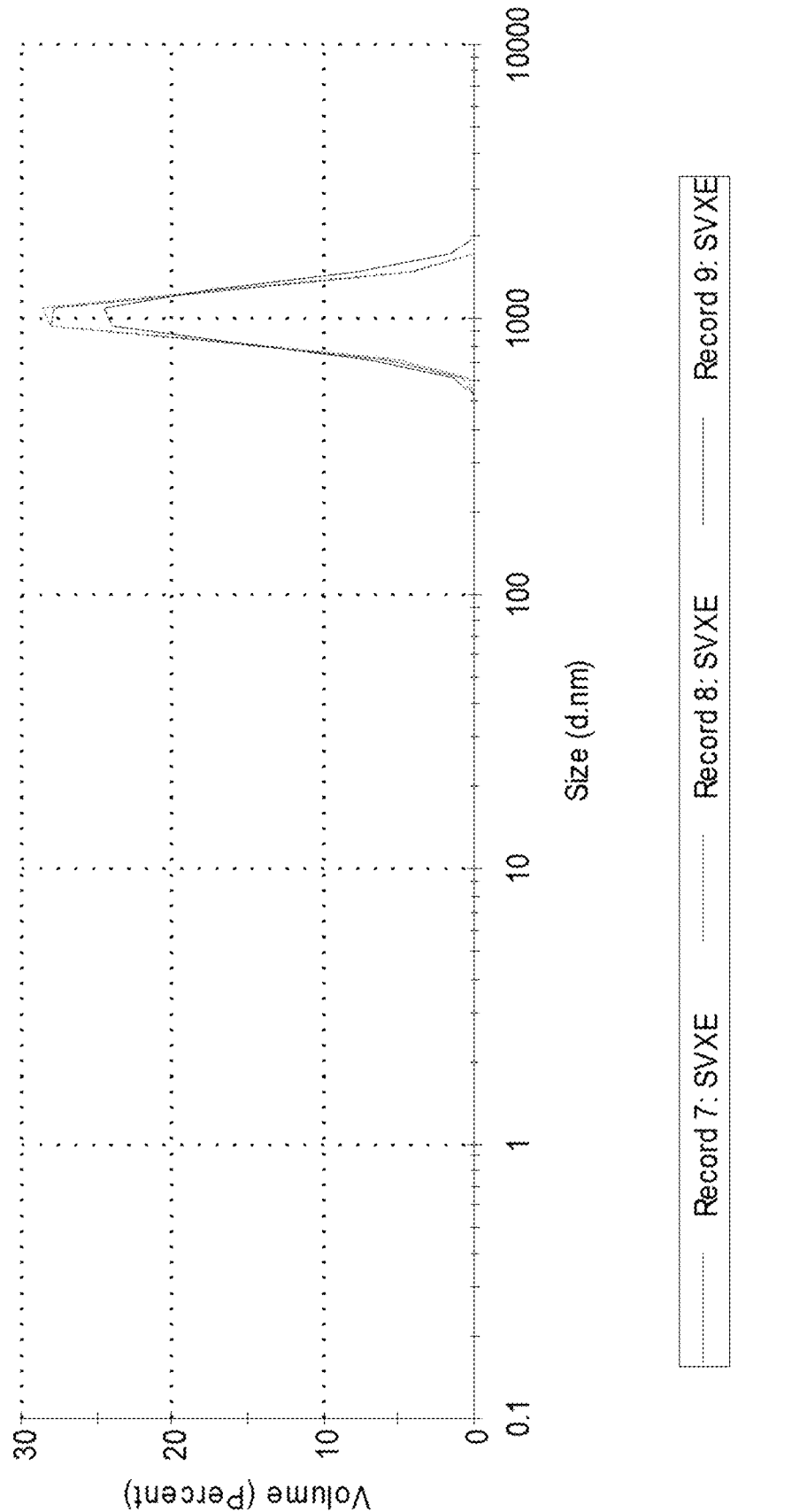
FIG. 2 is a graph exhibiting the particle size distribution of the proteins obtained using the described expression system.
Figure 3:
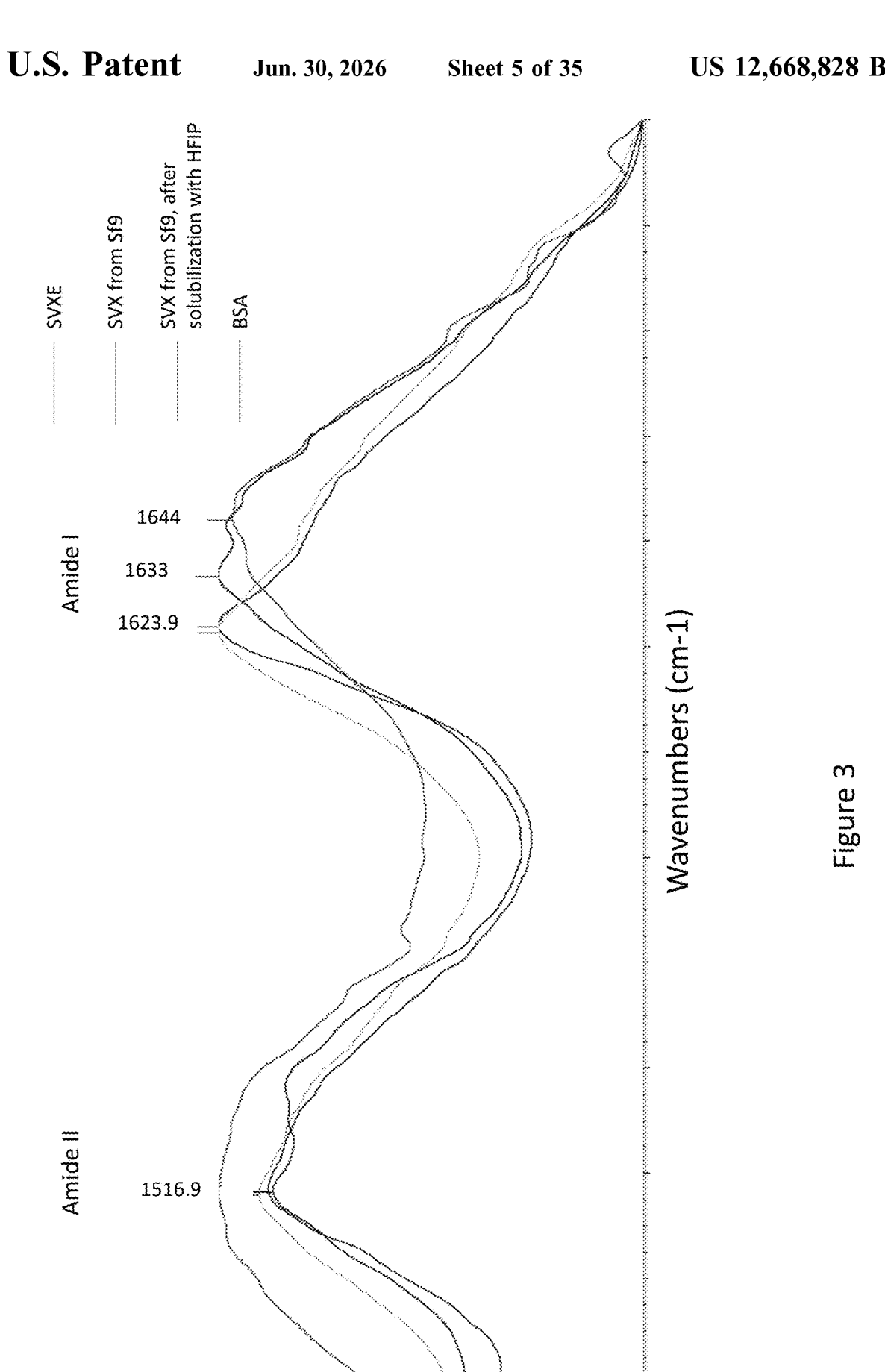
FIG. 3 is a FTIR analysis of the obtained particles.

The resulting product are particles containing β-sheets. Dynamic Light Scattering (DLS) was used and the determined particle size was 1.04±0.2 μm (FIG. 2), and FTIR analysis of the particles confirms the β-sheet structure (FIG. 3).

The Amide I peak of spider silk protein expressed in *E. coli* (SVXE) has a maximum at 1622 cm$^{-1}$, similar to a spider silk protein (SVX) from Sf9. This is the wavelength characteristic to β-sheets. SVX solubilized with HFIP (leading to α-helical conformation), or a native α-helix protein (BSA) show a shifted Amide I peak.

Figure 4:
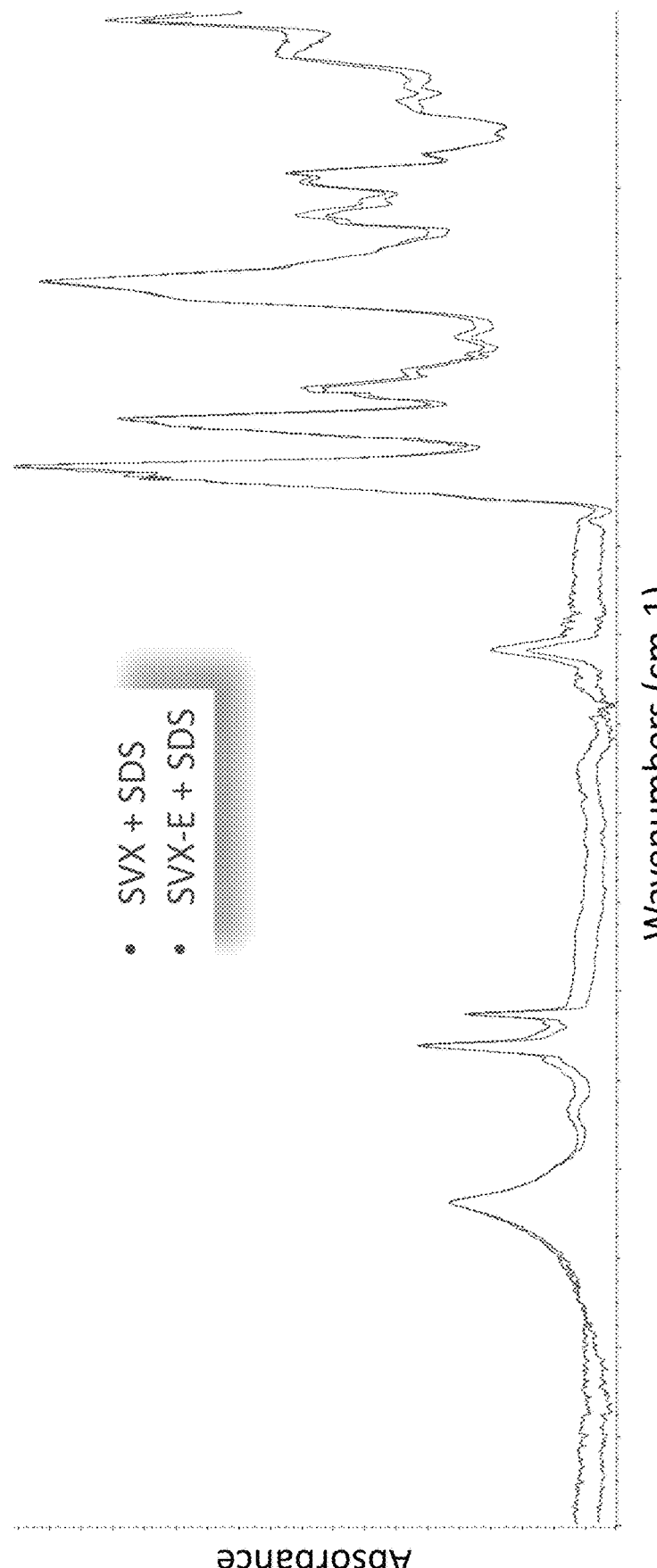
FIG. 4 is a FTIR spectrum of the spider silk protein expressed in bacteria (SVX-E) vs spider silk SVX expressed in Sf9 cells.

The FTIR spectrum of spider silk protein expressed in sf9 cells (SVX) was similar to spider silk protein expressed in *E. coli* (SVXE) (FIG. 4).

Figure 5:
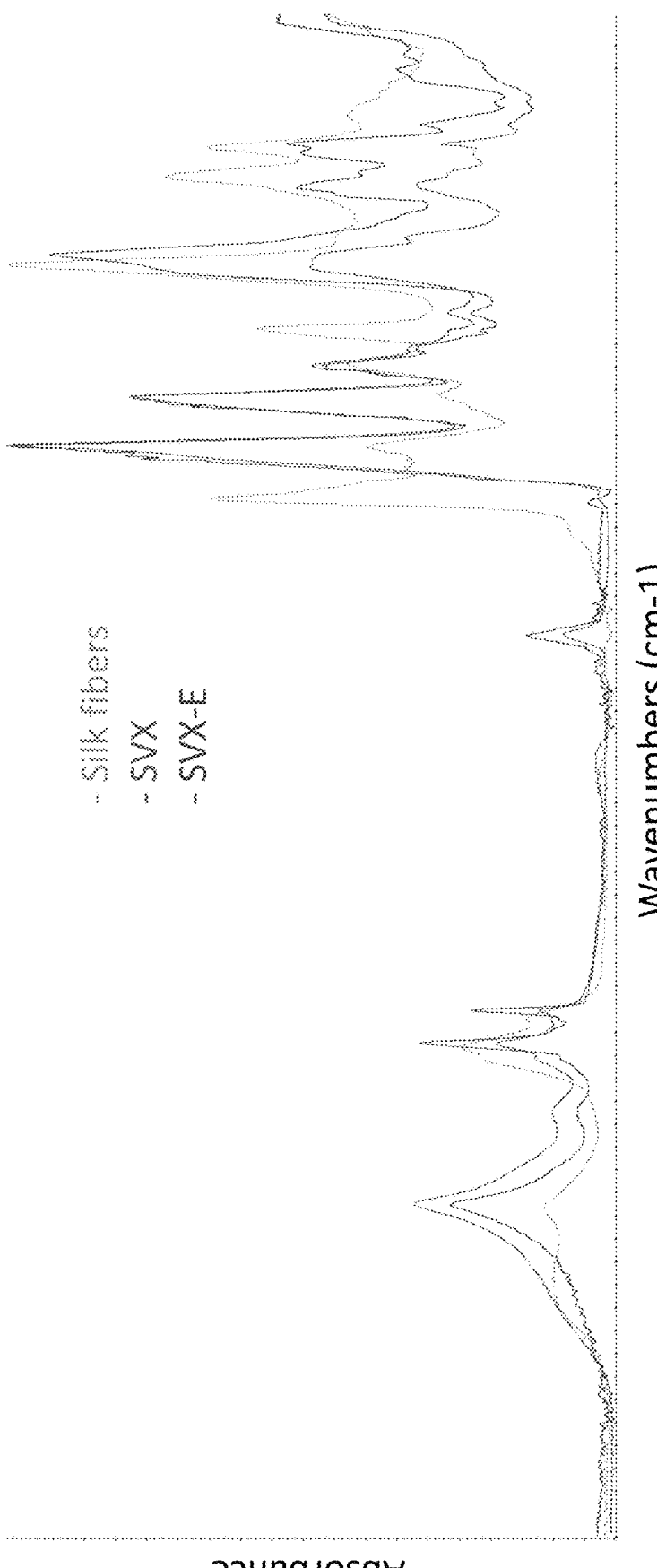
FIG. 5 is a FTIR spectrum of the spider silk protein expressed in bacteria (SVX-E) compared to spider silk expressed in Sf9 cells (SVX) and to silk fibers.

When compared to worm silk, the spectrum of worm silk shows unique peaks that are absent in the spectra of SVX and SVX-E (FIG. 5).

Differential Scanning calorimetry (DSC) of the particles confirms the crystalline structure.

Figure 6A:
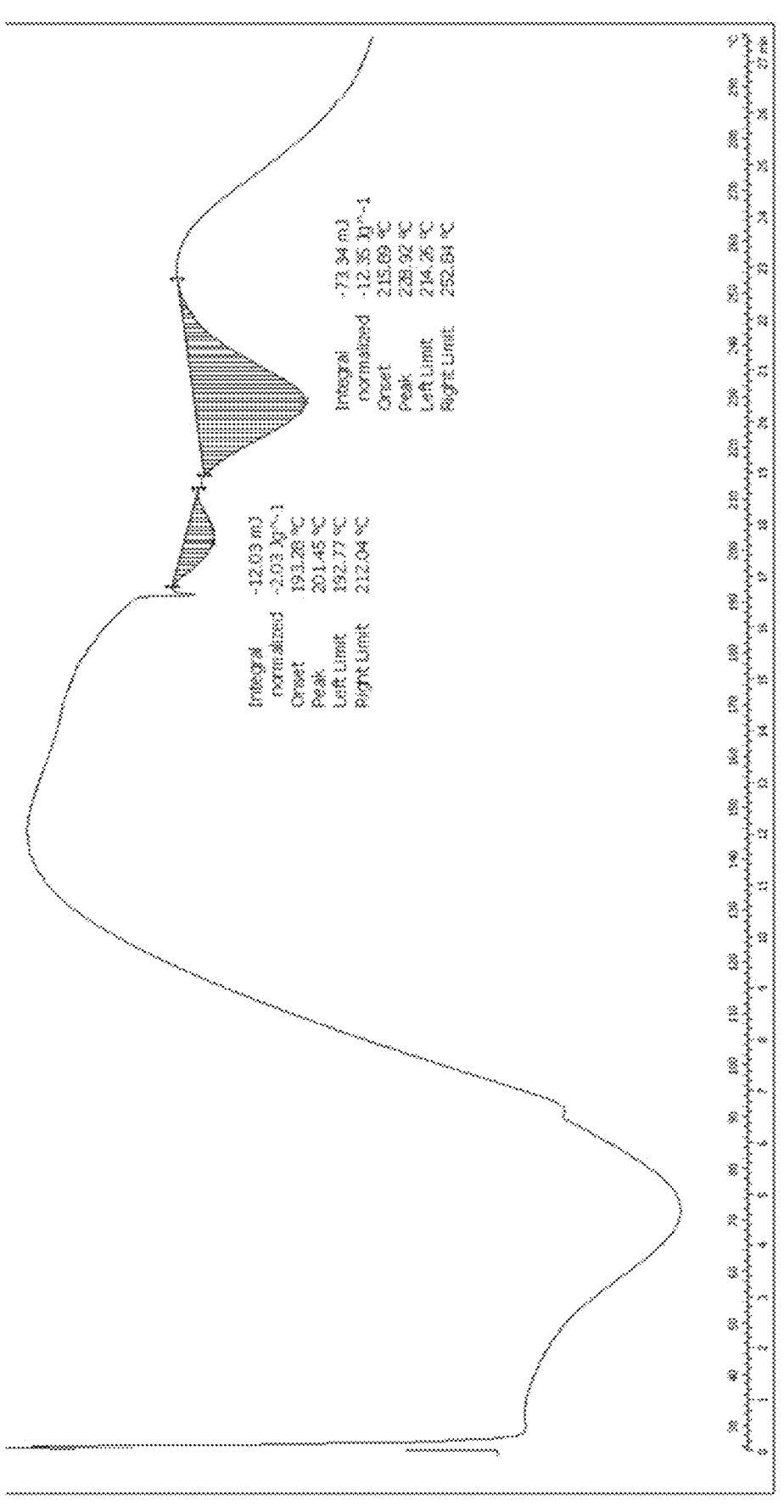
FIGS. 6A-C are Differential Scanning calorimetry (DSC) curves of the spider silk protein expressed in bacteria SVX-E (FIG. 6A and FIG. 6B) and DSC curve of SVX proteins (FIG. 6C)
Figure 6B:
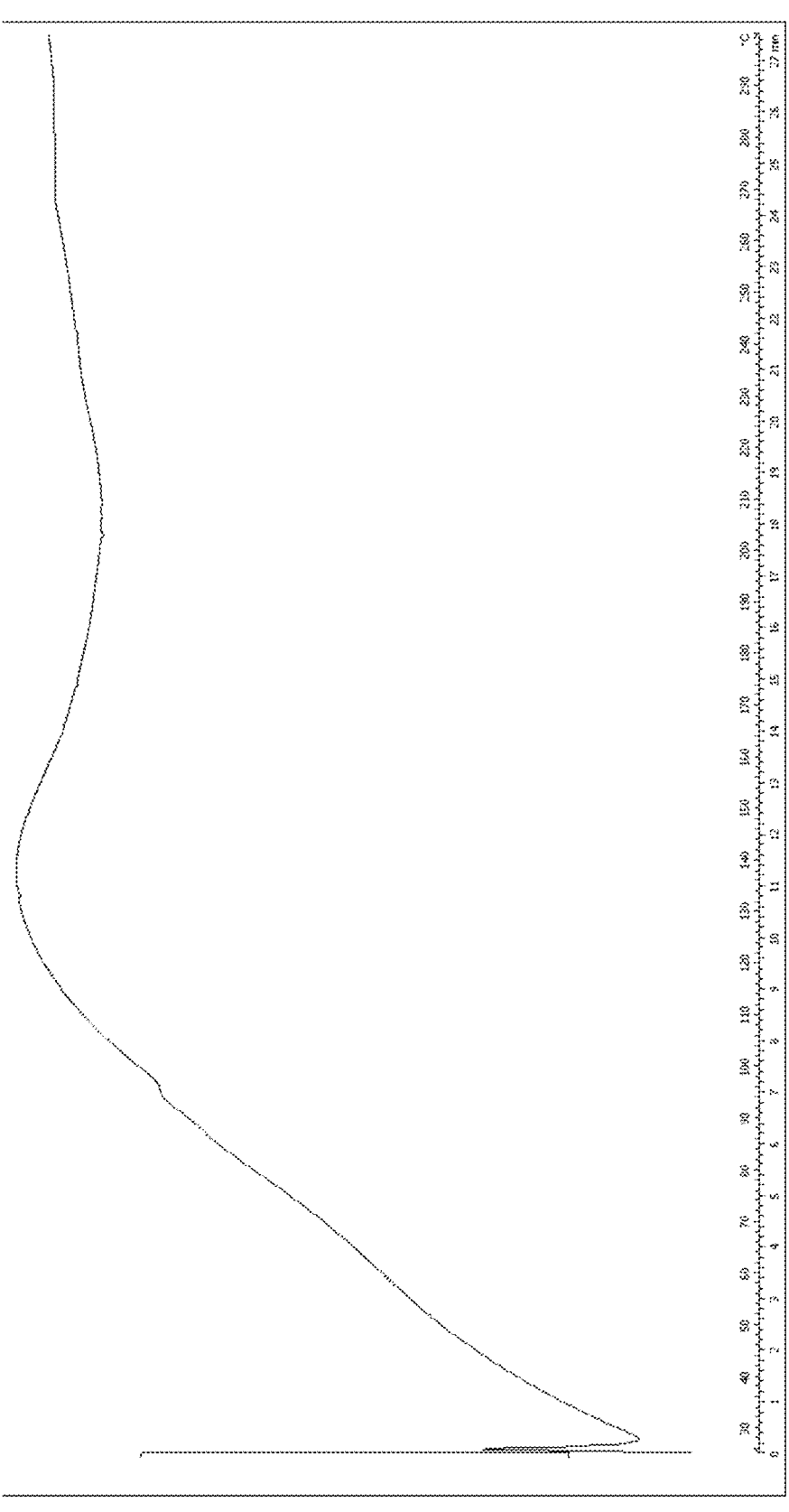

The particles have a phase transition at Tm=216° C. (FIG. 6A). The phase transition peak disappears in the protein denatured with 6 M guanidine SCN (FIG. 6B).

Figure 6C:
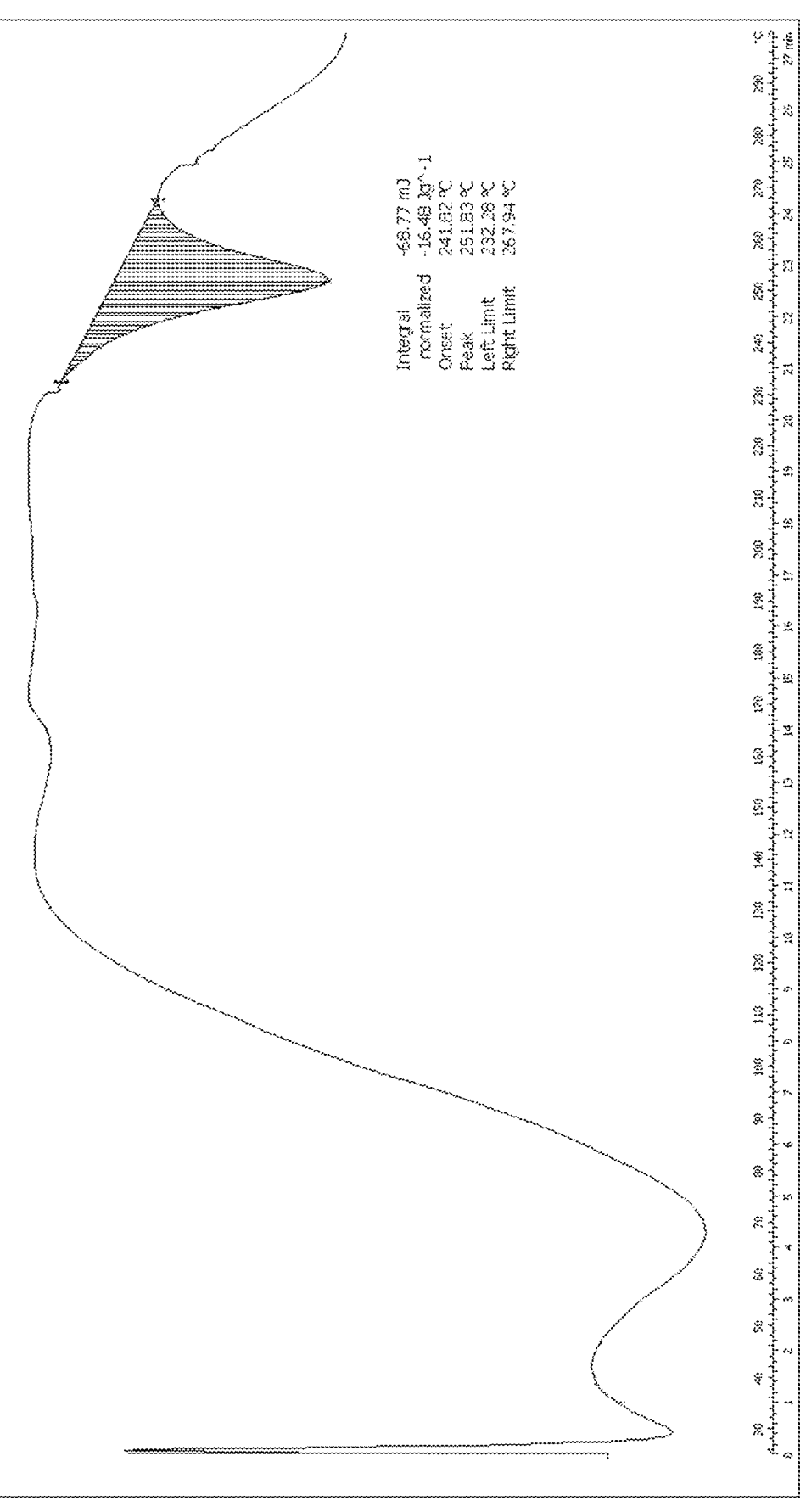

The fibers from Sf9 have a phase transition at Tm=242° C. (FIG. 6C).

Figure 7A:
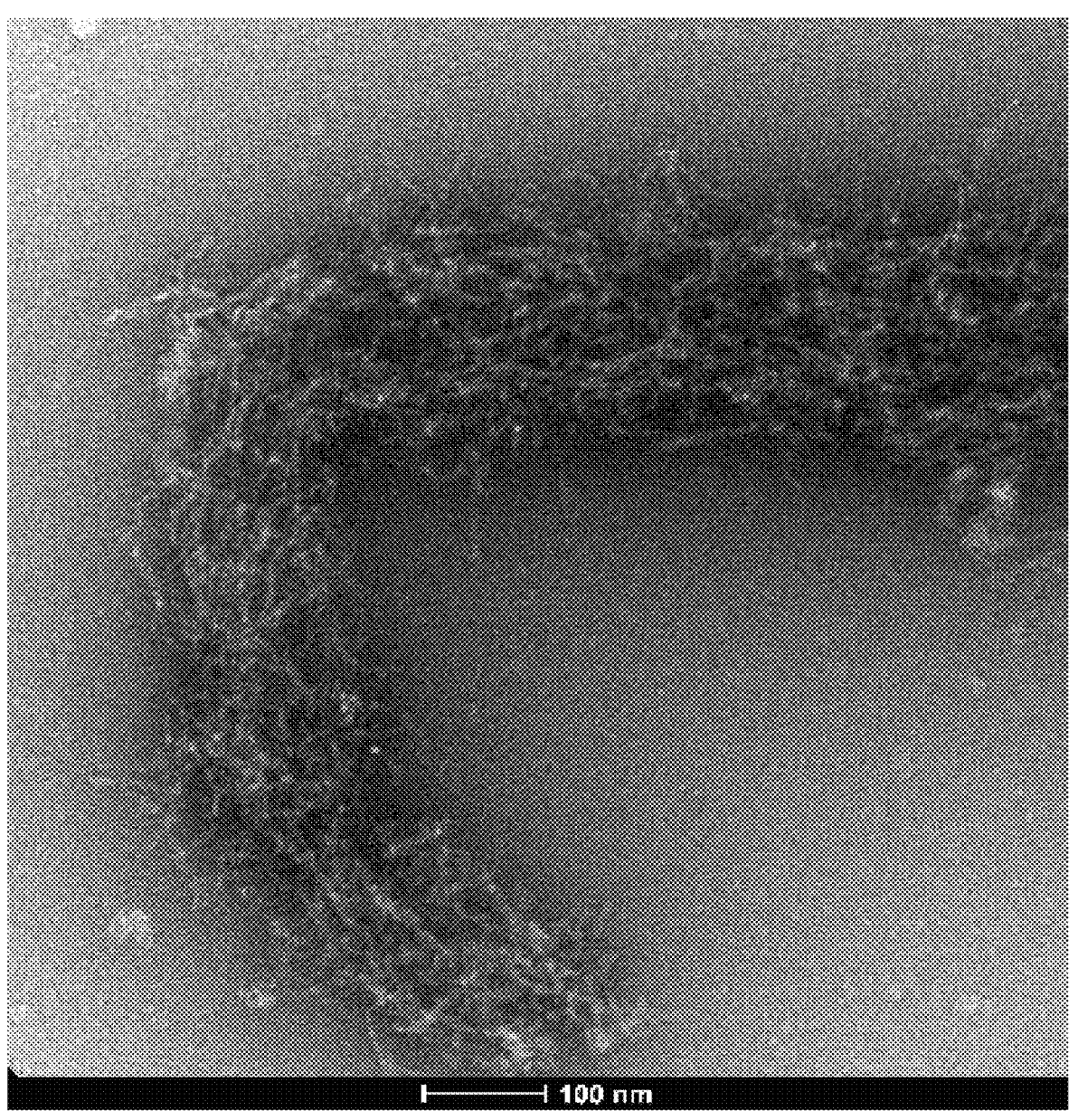
FIGS. 7A-B are images of Transmission Electron Microscopy of SVXE (FIG. 7B), compared to SVX from Sf9 (FIG. 7A).
Figure 7B:
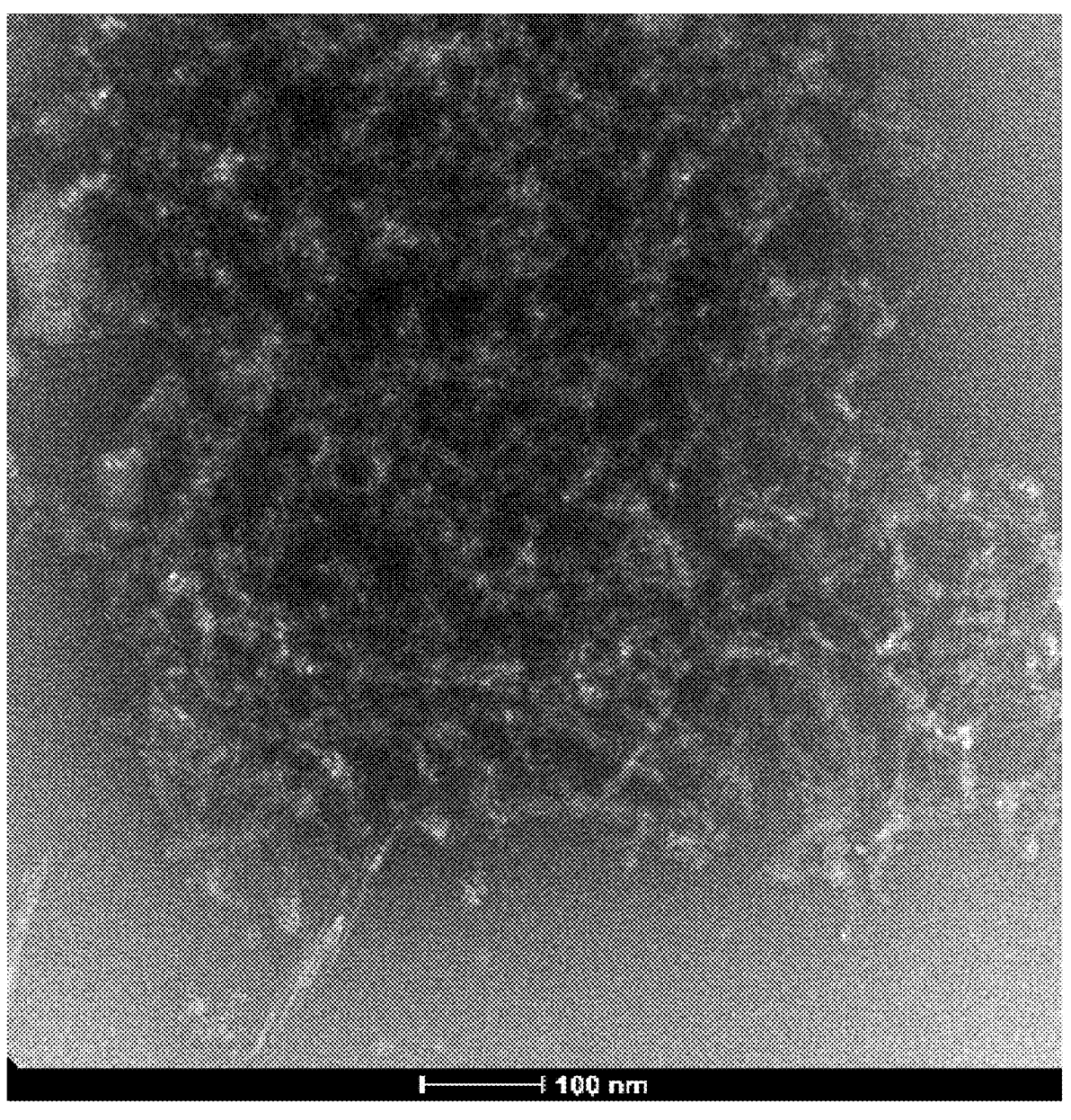
Figure 21C:
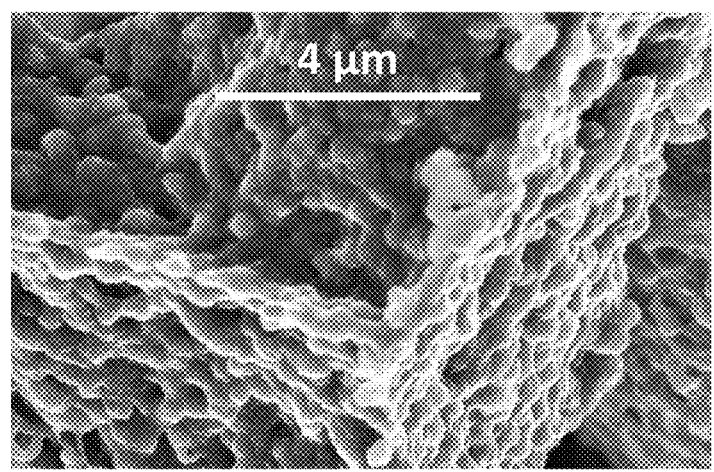
Figure 21D:
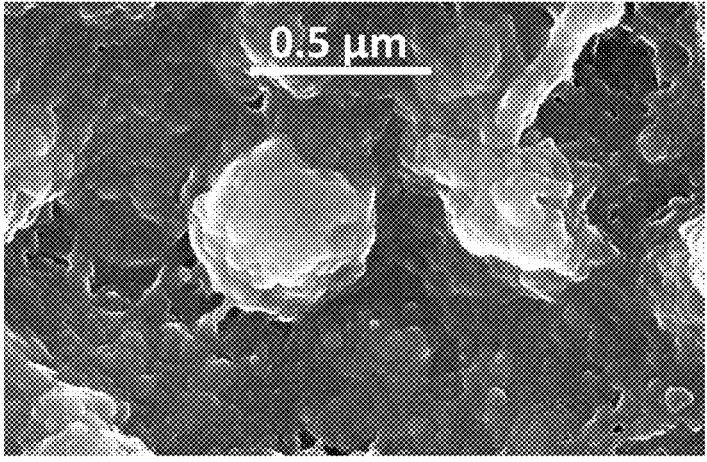

The TEM of SVXE particles reveals its fine structure that does not appear in common inclusion bodies (FIGS. 7A-B). Furthermore, SEM images of porous SVXE particles (FIGS. 21A-B) represents fibers composed of nanofibrils (represented by an arrow 1 at FIG. 21B), leading to very porous particle. When aggregation occurs, the porosity of the particles is apparently reduced (FIGS. 21C-D).

Figure 21E:
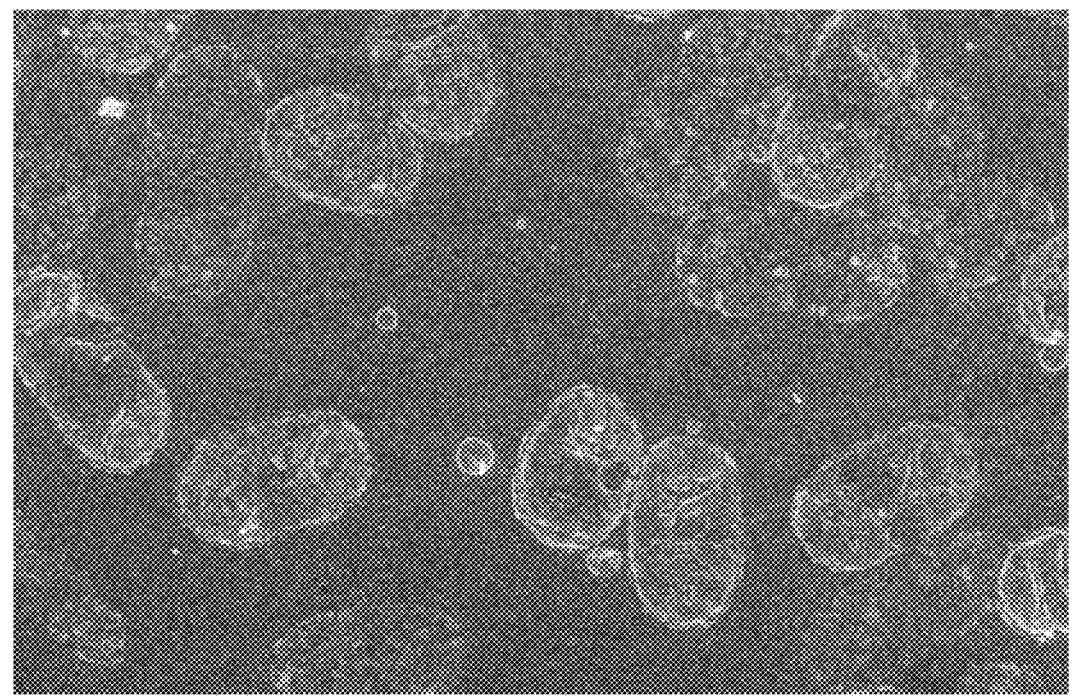

FIG. 21E represents a SEM image of a purified fermentation product resulting from expression of a different construct having an amino acid sequence as set forth in SEQ ID NO: 10 (MSYYHHHHHHDYDIPTTENLYFQGAMPRK-SPFPRPEL). Although, the fibers obtained from the expression of the different construct are in a form of a particle, however these fibers are substantially devoid of nanofibrils and lack any porous structure.

FTIR spectra (data not shown) of SVXE fibers (such as represented by FIGS. 21A-B) and of fibers obtained from the expression of the different construct having a sequence as set forth in SEQ ID NO: 10 (such as in represented by FIG. 21E), demonstrates that SVXE fibers are characterized by substantially increased amount of beta sheets, compared to the fibers having a sequence as set forth in SEQ ID NO: 10.

Example 2

Polymer Enrichment with Spider Silk Protein Expressed in Bacteria

In exemplary experiments, polyurethane P490RSJT was enriched with increasing amounts of SVX-E (Table 2).

TABLE 2

| Parameter | Polymer P490RSJT composite | | | | |
|---|---|---|---|---|---|
| | Control | 5% SVXE | 10% SVXE | 20% SVXE | 30% SVXE |
| Young's Modulus (MPa) | 42.5 ± 2.9 | 54.9 ± 1.1 | 70.9 ± 1.2 | 94.2 ± 1.1 | 151.4 ± 2.4 |
| UTS | 73.2 ± 3.7 | 61.4 ± 1 | 45.2 ± 3.3 | 52.7 ± 6.6 | 35.5 ± 2 |
| Percentage Total Elongation at Fracture | 1197 ± 157 | 911 ± 83 | 603 ± 67 | 709 ± 119 | 386 ± 8 |
| Toughness (J/mm³) | 466 ± 90 | 278 ± 38 | 138 ± 28 | 203 ± 52 | 85 ± 4 |
| Tensile strength | 72 | 60 | 45 | 52 | 35 |

Figure 8B:
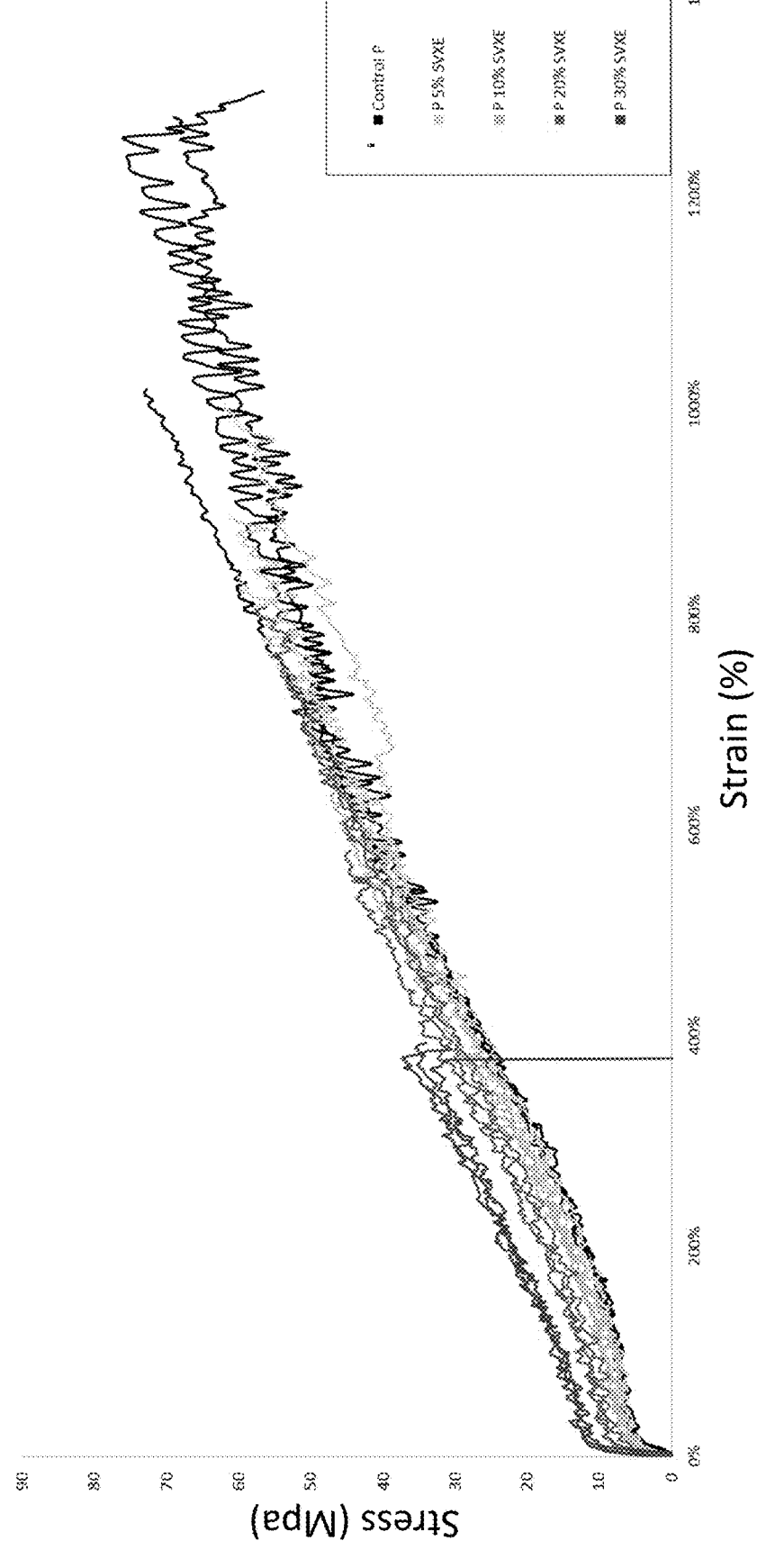
Figure 9E:
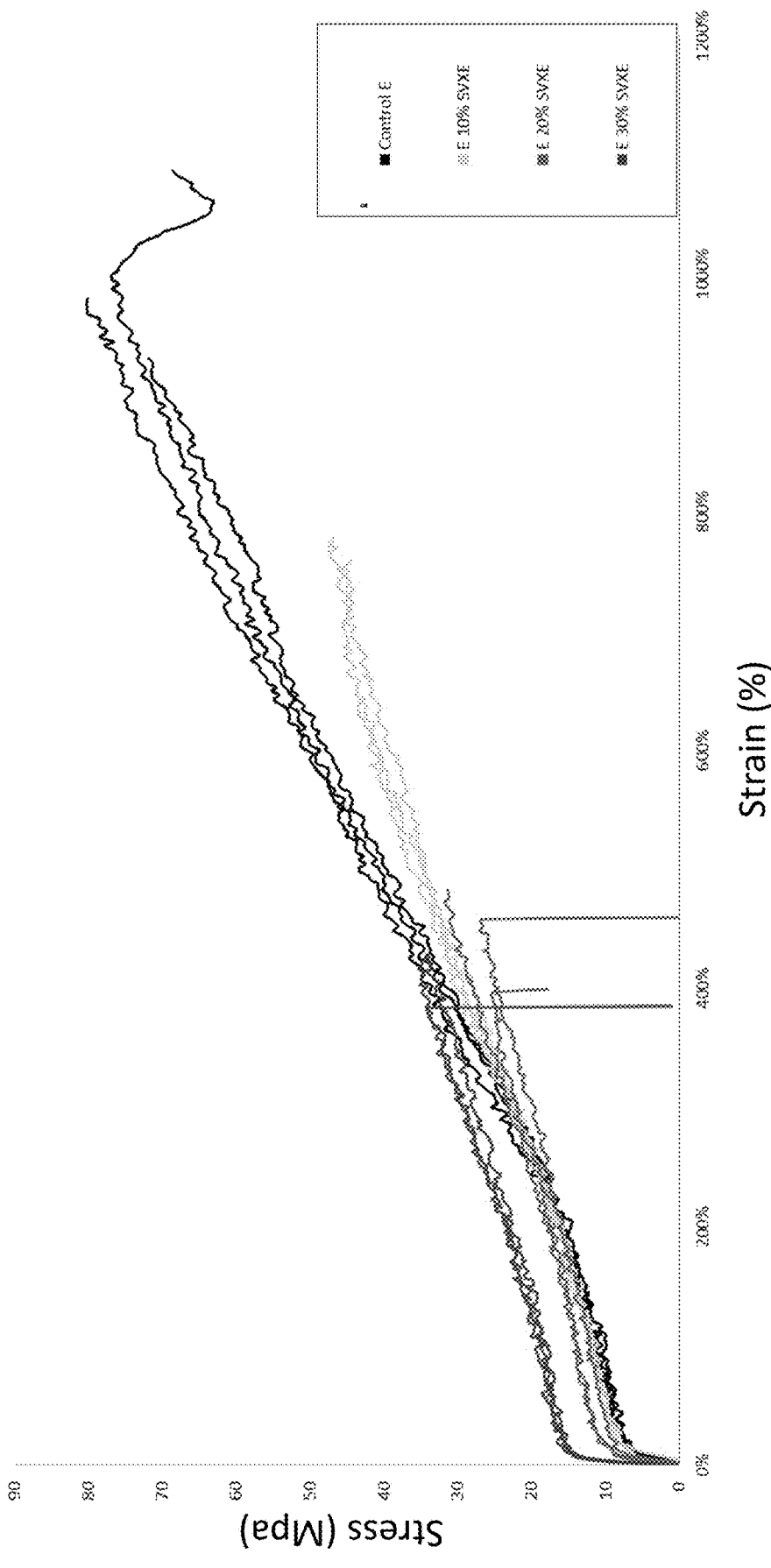
Figure 10E:
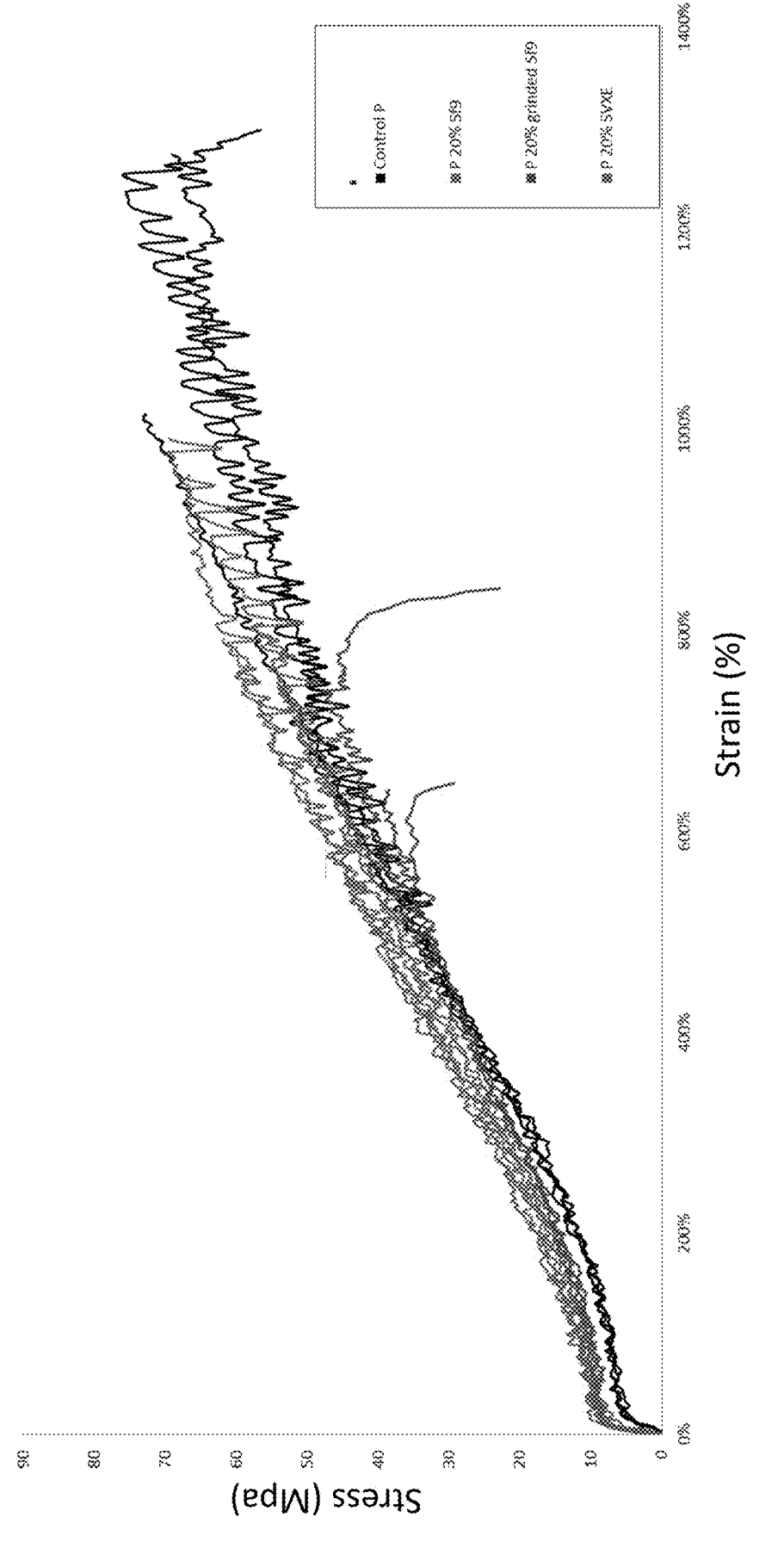
Figure 11A:
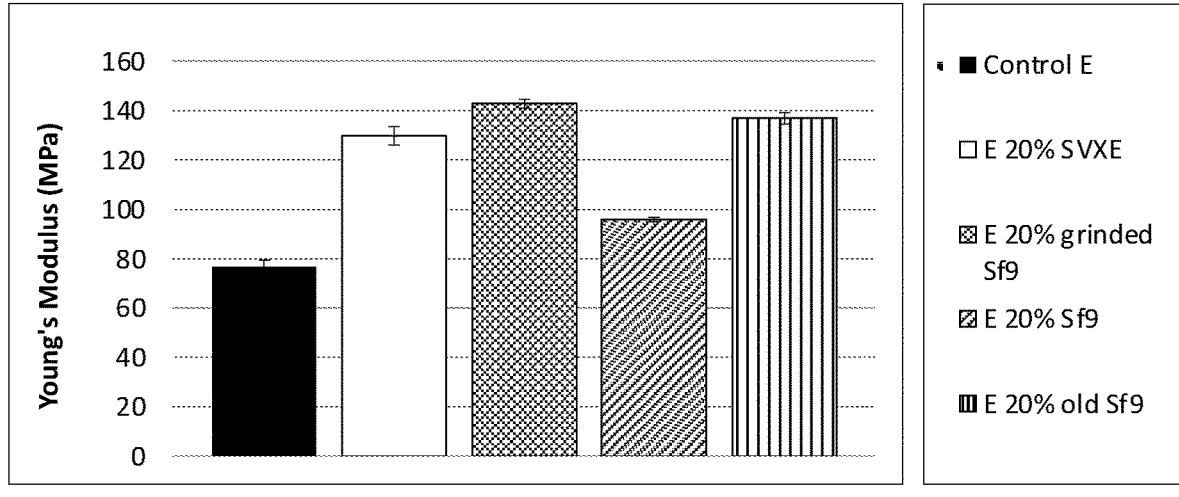
FIGS. 11A-E are graphs representing the comparison of mechanical properties of a polymer E394POTA PU and composites enriched with 20% SVX, grinded SVX & SVX-E respectively.
Figure 11B:
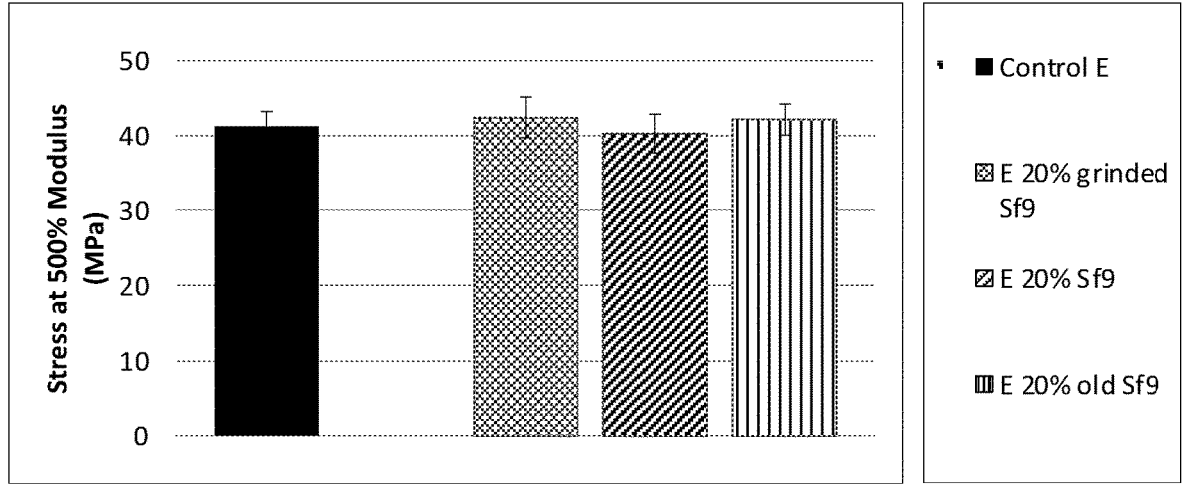
Figure 11C:
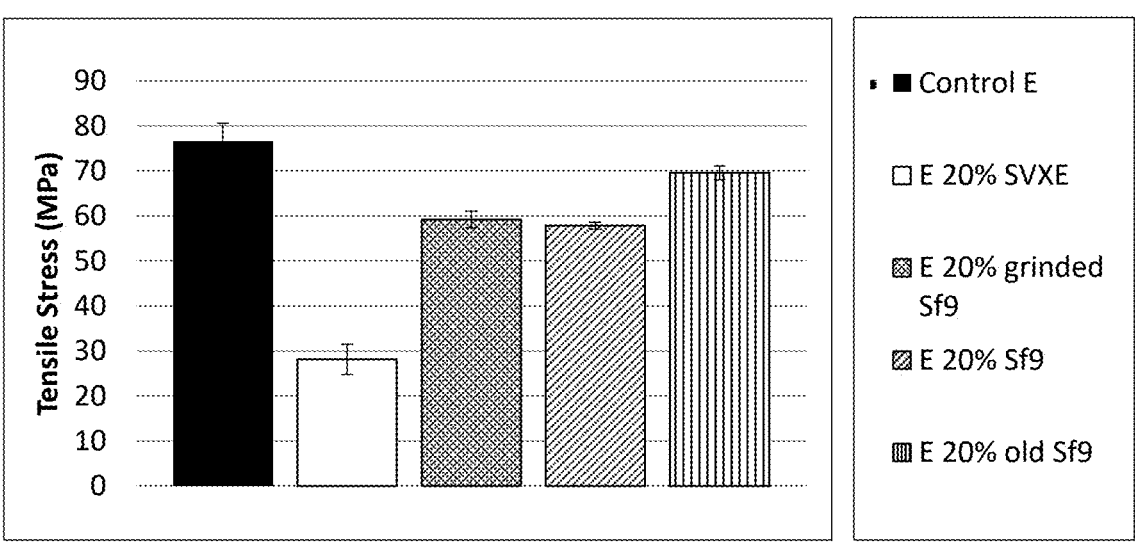
Figure 11D:
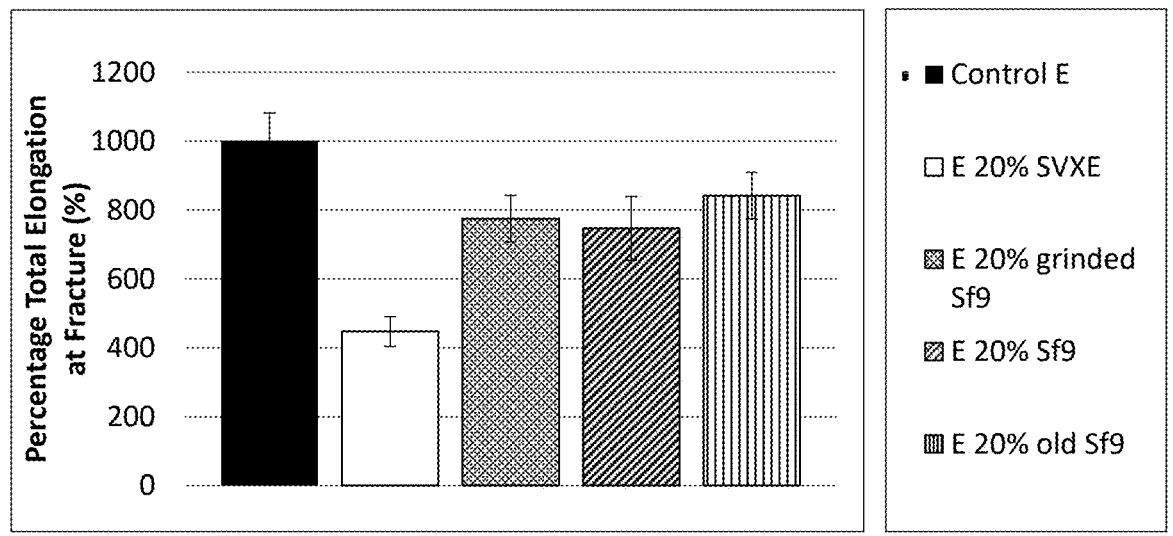
Figure 11E:
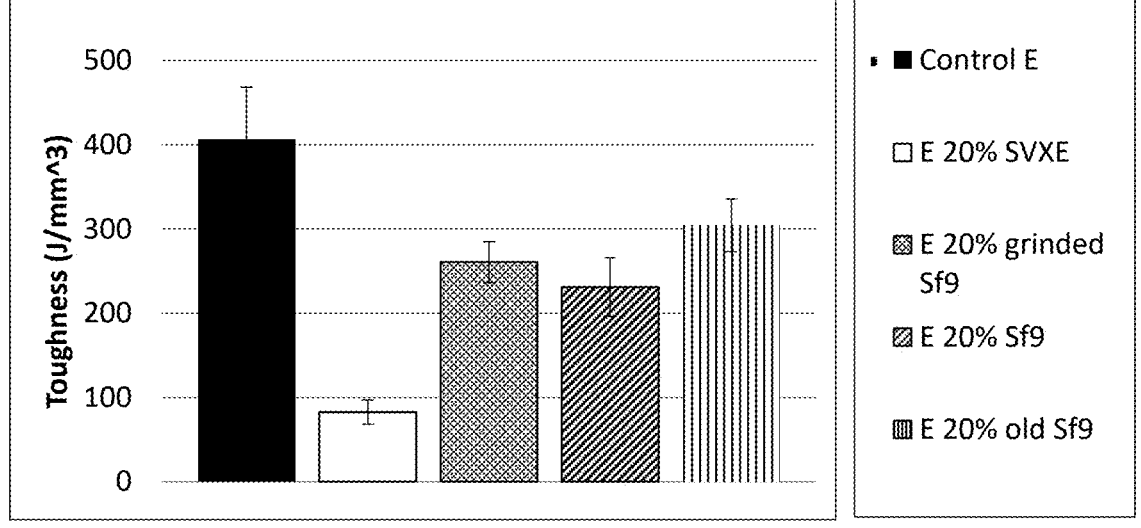

The results suggest a dose dependent response, where the Young Modulus increases with increasing % SVX-E, while the UTS, % elongation at break and toughness are decreased (FIGS. 8A-B).

A similar experiment was performed with the polymer E394POTA enriched with various concentrations of SVX-E. The results show a dose dependent response, where the Young Modulus increases with increasing % SVX-E, while the UTS, % elongation at break and toughness are decreased (FIGS. 9A-E).

FIGS. 10A-E present graphs of a comparison of composites made from polyurethane P490RSJT containing 20% SVX or SVX-E. Both SVX and SVX-E made the polymer stiffer as is evident by the increased Young Modulus compared to control. There was no difference between SVX and SVX-E in that regard. Both SVX and SVX-E decreased the tensile strength, % elongation and toughness compared to control. SVX-E showed a larger effect than SVX.

FIGS. 11A-E present graphs of a comparison of composites made from polyurethane E394POTA containing 20% SVX or SVX-E. Both SVX and SVX-E made the polymer stiffer as is evident by the increased Young Modulus compared to control. There was no difference between SVX and SVX-E in that regard. Both SVX and SVX-E decreased the tensile strength, % elongation and toughness compared to control. The strain-stress curve (not shown) showed a similar behavior, as in FIGS. 8B, 9E and 10E. SVX-E showed a larger effect than SVX.

Table 3 describes a comparison of composites made from polyurethane P409RSJT containing 20% SVX or SVX-E, and a comparison of composites made from polyurethane PU399 containing 5% & 10% SVX or SVX-E.

TABLE 3

| Parameter | Polymer P490RSJT composite | | | Polymer PU399 composite | | | | |
|---|---|---|---|---|---|---|---|---|
| | Control | 20% SVX-E | 20% SVX | Control | 5% SVX-E | 5% SVX | 10% SVX-E | 10% SVX |
| Young's Modulus (MPa) | 42.1 ± 2.2 | 117 ± 5 | 102.3 ± 2.1 | 1.6 ± 0.1 | 4.7 ± 1.1 | 5.7 ± 0.5 | 3.8 ± 0.3 | 4.5 ± 0.4 |
| UTS | 60.9 ± 5.2 | 47.9 ± 1.6 | 62.2 ± 5.4 | 35.8 ± 12.1 | 39.5 ± 4.5 | 23.2 ± 5.3 | 45.3 ± 1.1 | 35.8 ± 4.9 |
| Total Elongation at Fracture, % | 965 ± 101 | 633 ± 47 | 690 ± 49 | 751 ± 157 | 652 ± 72 | 629 ± 59 | 730 ± 141 | 822 ± 114 |
| Toughness (J/mm³) | 303 ± 56 | 169 ± 16 | 230 ± 39 | 65.2 ± 33.8 | 82.8 ± 16 | 54.5 ± 12.4 | 114.2 ± 8.8 | 115.6 ± 28 |

Additional polymers have been enriched with SVX-E fibers and the mechanical properties of the resulting materials have been examined. The results are summarized herein below (Table 3A), showing a significant increase (between 130 and 1160%, including any range between) in Young's modulus of the SVX-E enriched polymeric compositions.

TABLE 3A

| Polymer | SVXE % w/w | Young's modulus (MPa) | Young's modulus Increase |
|---|---|---|---|
| TPU Pe-399 (Huntsman) | 0% | 3.6 | — |
| | 15% | 45.6 | 1167% |
| TPU SG-60D (Lubrizol) | 0% | 76 | — |
| | 15% | 179 | 136% |
| PEVA | 0% | 53 | — |
| | 10% | 204 | 285% |

Furthermore, film forming agents have been enriched with 10% w/w SVX-E fibers and the mechanical properties of the resulting materials have been examined. The results are summarized in FIG. 14, showing a significant increase (between 73 and 145%) in Young's modulus and in UTS of the film formers (pullulan and Liftonin Xpress®) enriched with SVX-E. Additionally, a significant increase (between 10 and 500%, including any range between) in storage modulus and a significant increase (between 10 and 60%, including any range between) in loss modulus of the tested film formers (pullulan, Liftonin Xpress®, Intansyl®, SKI Nacture®, TriK Fision®, LiftLiss SB®, Gosulin Agave®) enriched with SVX-E has been obtained, as demonstrated in FIG. 14.

Example 3

Loading and Release of Hyaluronic Acid

Spider silk fibers (SVX) or spider silk fibers expressed in bacteria (SVX-E) washed twice with ethanol and then with water (as described hereinabove). 10 mg of hyaluronic acid (HA) were added to 10 mg of SVX dispersed in 1-20 mL water. pH was adjusted with HCl or Phosphate Buffer and water added so as to reach the desired volume. The mixture was shaken and centrifuged. The supernatant was discarded, and a small sample of pellet was dried on glass slide, resulting in HA+SVX-E or HA+SVX pellets. The pelletes have been subsequently tested by FTIR (Nicolet iS5 FTIR Spectrometer, Thermo Fisher Scientific). The remaining pellet was resuspended in water, and the suspension was shaken for 1-30 mins at 200 rpm at 25° C. This process was repeated for several times. For each pellet sample analyzed by FTIR, the fraction of HA out of the total dry weight was calculated by dividing the intensity of a peak unique to HA by the intensity of a peak unique to the polymers (Table 4). These results confirm the capability of MaSp-based fibers (e.g. SVX or SVX-E) to stably encapsulate an additional compound (e.g. HA), wherein the w/w ratio of the encapsulated compound to the fiber (e.g. SVX or SVX-E) is about 1:1.

TABLE 4

| Mixture | HA peak | polymer peak |
|---|---|---|
| HA + SVX or HA + SVX-E | 1040 cm$^{-1}$ | 1640 cm$^{-1}$ |
| HA + silk | 1040 cm$^{-1}$ | 1550 cm$^{-1}$ |

Example 4

Effect of pH on Formation of SVX-E in *E. coli*

Figure 15:
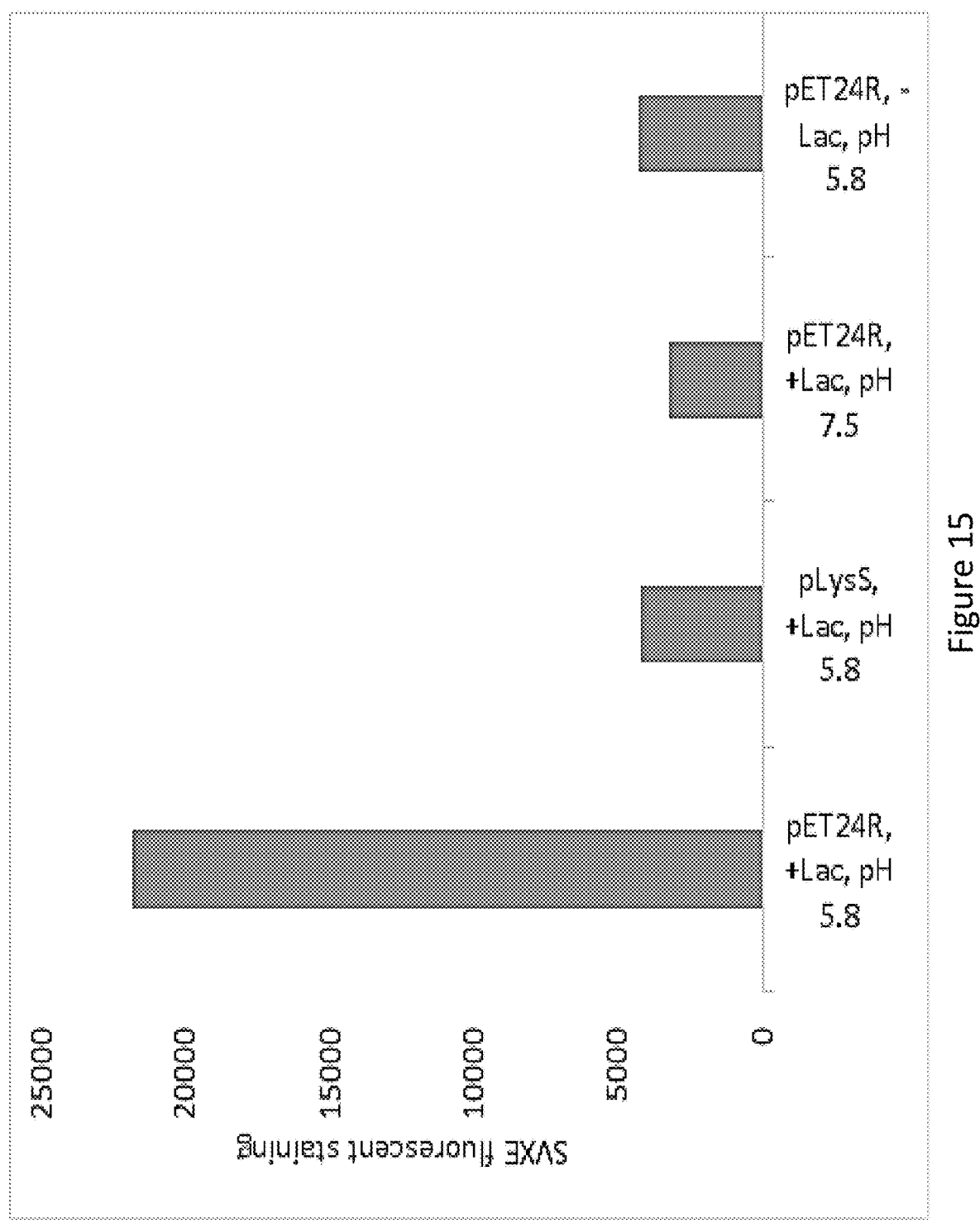
FIG. 15 is a graph of the amount of SVX-E at 30 hours culture in *E. coli*; the SVX-E was determined using a specific beta sheet crystal binding fluorescent dye.

The following example shows that the formation of SVX-E in *E. coli* is dependent on the medium pH (FIG. 15). The detection of SVX-E was done using a beta-sheet specific fluorescent dye that binds only self-assembled spider silk but not soluble spider silk.

The data also shows that SVX-E is expressed only in the presence of lactose (which is the inducer for SVX-E expression) and the expression plasmid for SVX-E.

Figure 16:
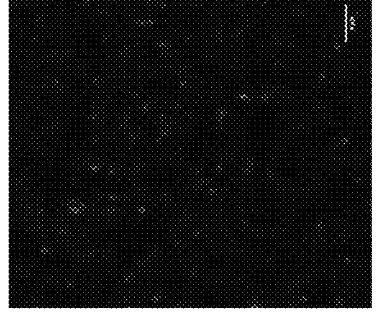
FIG. 16 are pictures of SVX-E staining at different culture times in pH 5.8 and pH 7.5; the green spots are due to specific beta crystal binding fluorescent dye entering the cells.

FIG. 16 shows the staining images taken with a confocal microscope at different time points, in cultures grown at either pH 7.5 or pH 5.8.

Example 5

Expression of SVX-E has a Biphasic Kinetics Pattern

The following example shows that SVX-E is produced in its final insoluble form at a delay following the induction of recombinant spider silk protein. Since protein synthesis is not induced at a certain time by adding an inducer (for example lactose or IPTG) but rather the inducer is present in the growth media from the beginning (in the presence of a little glucose as the preferred carbon source, once it is consumed lactose is utilized and recombinant protein synthesis begins). The way to follow the kinetics of recombinant protein synthesis is by comparing the growth rates of 2 cultures, one with lactose (the expressing culture) and another without lactose (the control culture). The difference between the growth rate (measured absorbance at 600 nm) of the 2 cultures shows that the lactose containing culture had a slower growth rate than the control culture without lactose. Without being bound to any particular theory, this is interpreted as induction of expression of spider silk in the slower culture as it is known that when bacteria express recombinant protein their growth rate is slowed down due to harnessing the metabolic machinery to protein synthesis rather than to growth.

Figure 17:
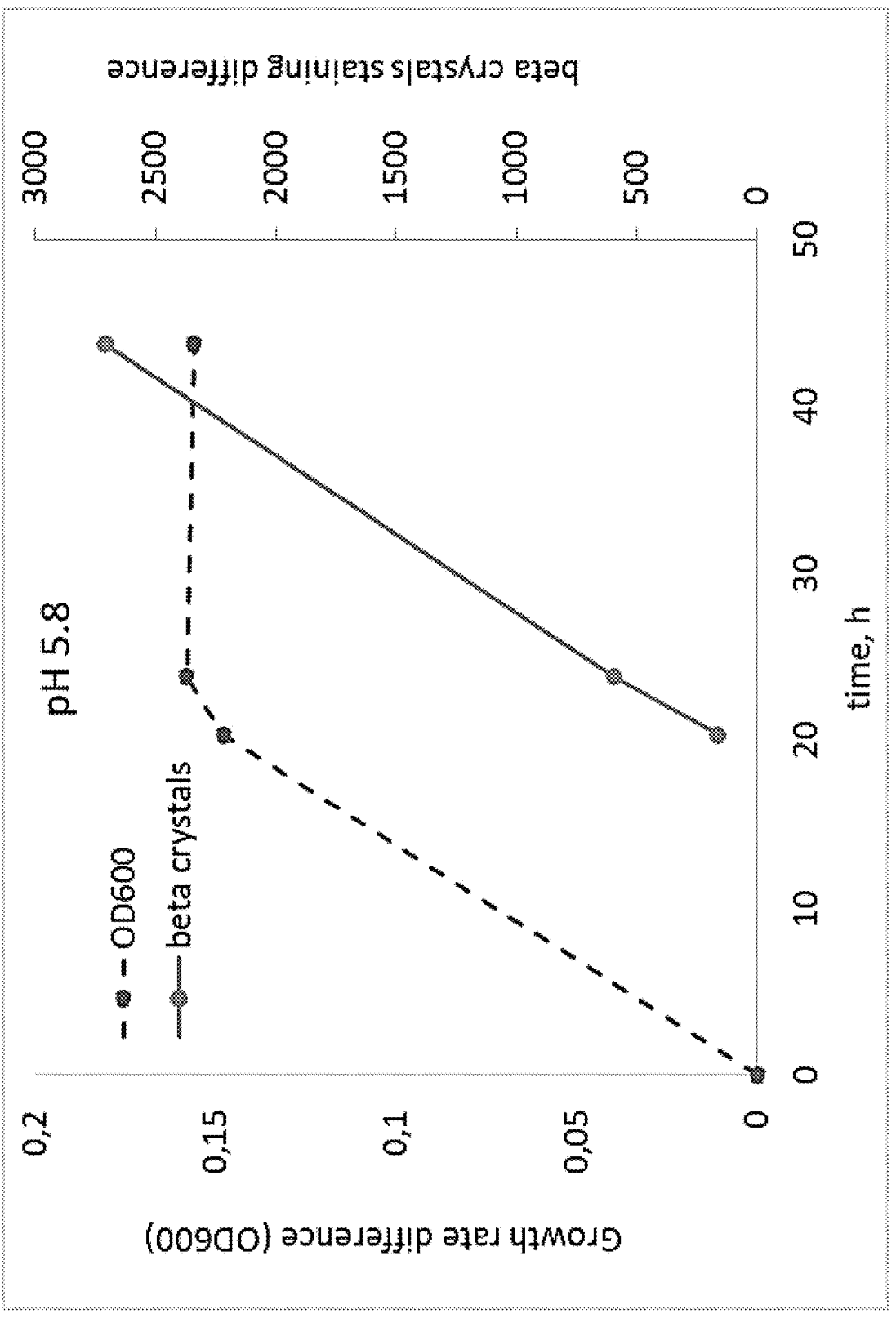
FIG. 17 is a graph of the growth rate and beta sheet crystals staining difference at pH 5.8, over a period of time.

FIG. 17 demonstrates that, the protein expressing window of time is when the expressing culture is lagging behind the control culture. The inventors have used a specific probe to beta sheet crystals, the structure that form as beta sheets stack against each other (pleated beta sheets)—a well-known property of natural and artificial spider silk (such as SVX-E) but not of soluble spider silk protein (spidroin).

Figure 18:
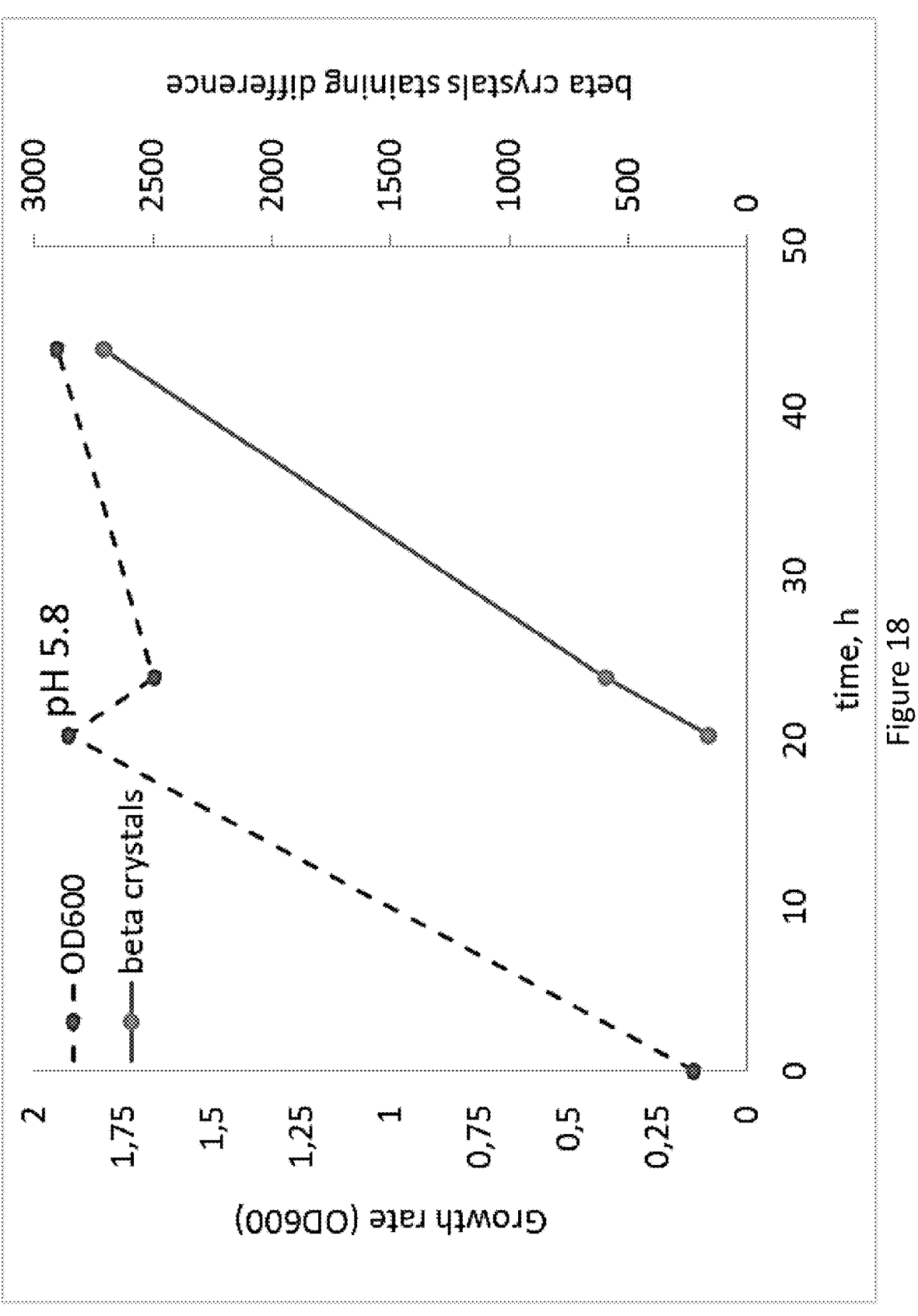
FIG. 18 is a graph of the absolute growth curves at a pH 5.8, over a period of time.

The increase in insoluble SVX-E happens after the 2 cultures achieved equal growth rate at around 20 hours, at this time the bacteria no longer expresses SVX-E. Moreover, by looking at the absolute growth curves (FIG. 18), it can be seen that the formation of insoluble SVX-E starts only after the bacteria have reached the stationary phase, when recombinant proteins are usually not expressed anymore Taken together, the results indicate that at pH 5.8, the production of recombinant spider silk has a bi-phasic kinetics, where in the first phase the soluble spidroin protein is formed, and in the second phase, once a critical intracellular concentration of the soluble protein has accumulated, self-assembly of the SVX-E takes place, stabilized by intra- and intermolecular beta sheets and beta sheet crystals.

Figure 19:
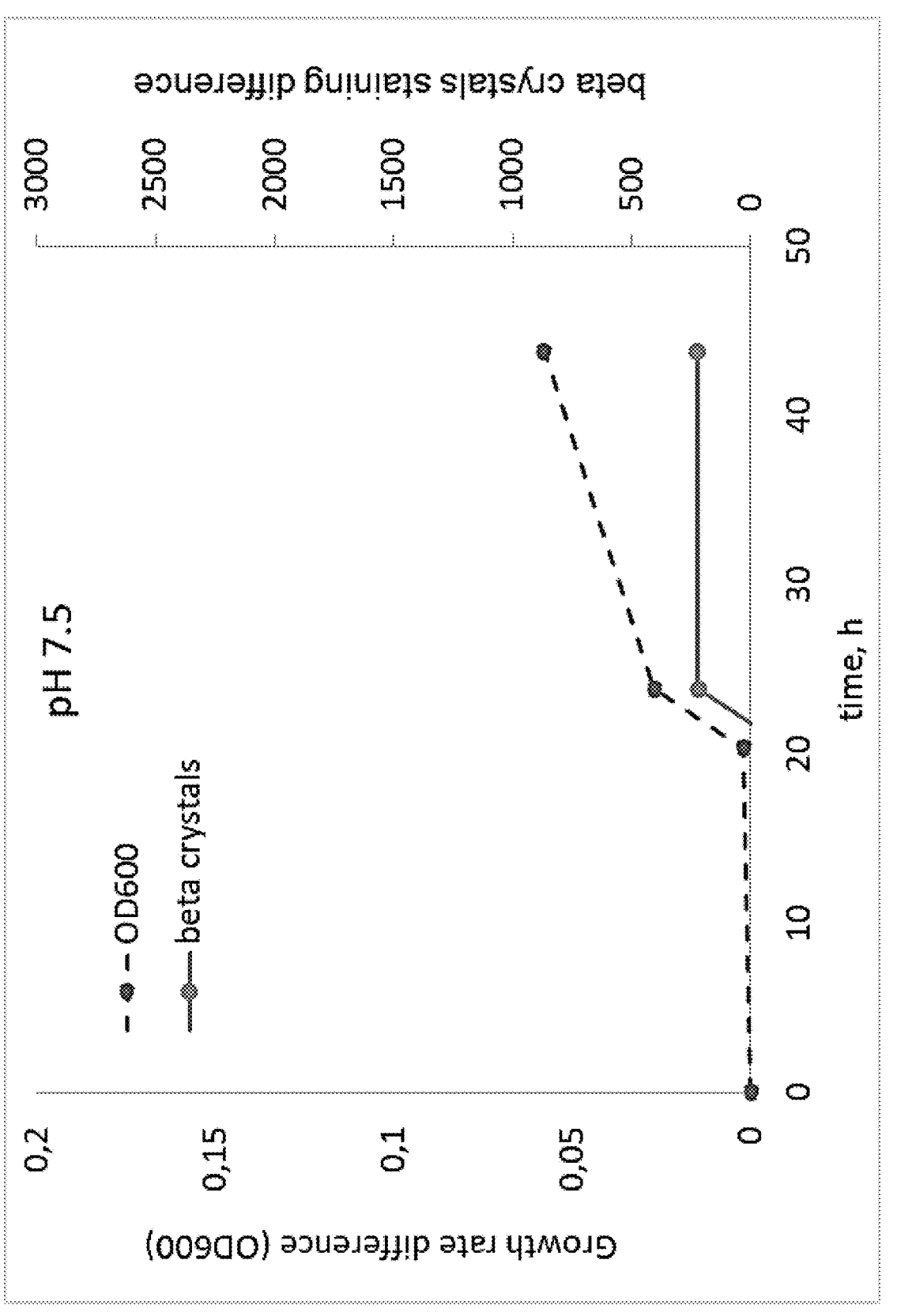
FIG. 19 is a graph of the growth rate and beta sheet crystals staining difference at pH 7.5, over a period of time.
Figure 20:
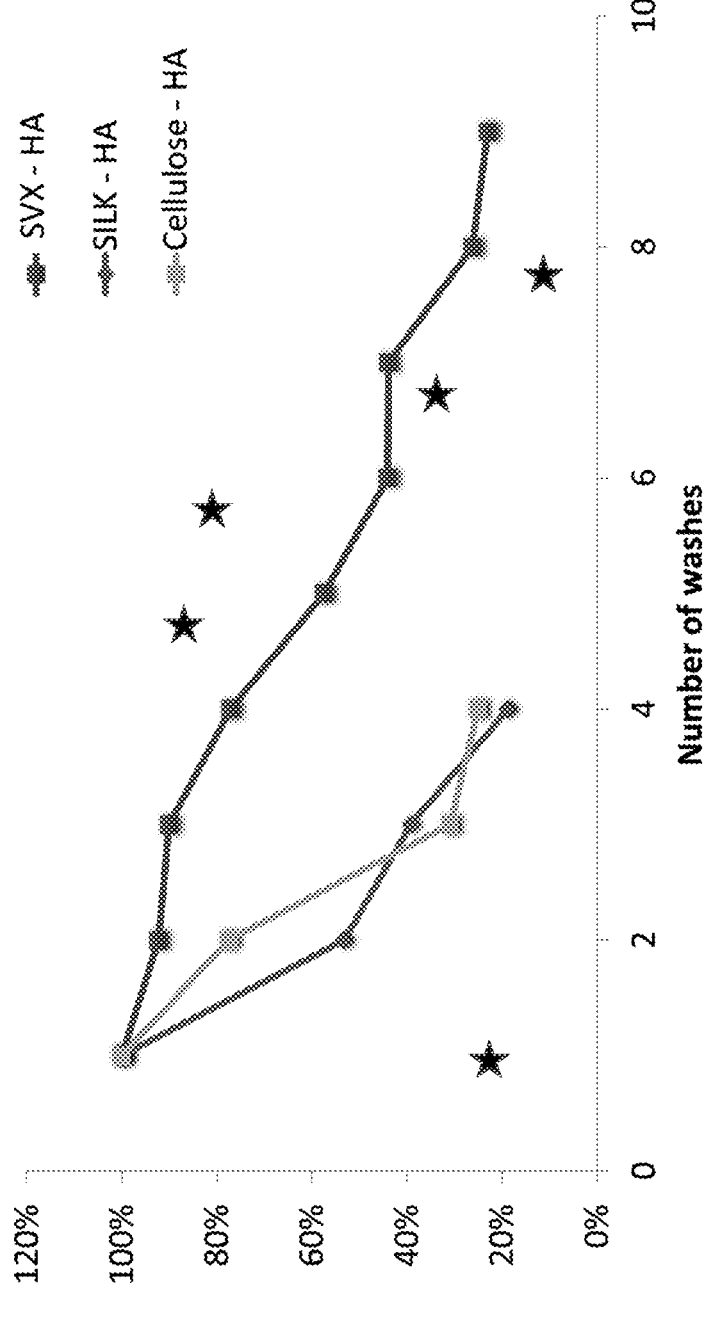
FIG. 20 is a graph representing the release of hyaluronic acid (HA) from SVX-E fiber, compared to Cellulose, and Silk. The graph shows the calculated ratio between HA specific peak and SVX-E/silk/cellulose specific peak (Y axis) vs. the wash number (X axis).

At pH 7.5 (FIG. 19) none of the above happens. No insoluble SVX is detected (phase 2) and there is no indication of differential growth and soluble protein expression at phase 1.

The inventors have seen a similar phenomenon in SF9 cells expressing SVX. Appearance of SVX as detected by the same beta sheet crystals specific staining is seen 70 hours after the culture has been infected with baculovirus, at this stage cells have reached the stationary phase and they are not dividing. These results, again, point to a biphasic kinetics of SVX production in insect cells as well.

Example 6

Dissolution Profiles of SVX and SVX-E in Various Denaturing Agents

Table 5 summarizes experimental data, showing that SVX and SVX-E have a similar dissolution profile in well-known denaturing agents (DA) urea (not shown), guanidinium chloride and guanidinium thiocyanate. Table 5 represents a molar concentration of a particular denaturing agent ($C_{1/2}$ (DA)) required for dissolution of 50% w/w of the total amount of any one of the fibers (SVX and SVX-E). As represented by Table 5, similar concentrations of various DAs are required for dissolution of both fibers (SVX and SVX-E).

TABLE 5

| Denaturing | $C_{1/2}$ (DA) [M] | |
|---|---|---|
| agent (DA) | SVX | SVX-E |
| guaSCN | 2.4 | 2.4 |
| guaHCl | 4.6 | 4.9 |

The data suggests that both have a similar chemical composition, and that the difference in dispersibility is due to the smaller size of SVX-E which results in a higher surface area.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A composition comprising a synthetic major ampullate spidroin protein (MaSp)-based polymer in the form of particles having an average size in the range of 0.5 µm to 1.5 µm; wherein said MaSp-based polymer is a MaSp1 protein comprising a single N-terminal region, a single C-terminal region and a repetitive region comprising 10-20 repeats, wherein at least one of: (i) each of said repeats is between 5 and 60 amino acids long; and (ii) each of said repeats has at least 70% homology to a repetitive sequence derived from the repetitive region of *Araneus diadematus* fibroin 4 (ADF4) protein, wherein the repetitive region of the ADF4 protein comprises the amino acid sequence as set forth in SEQ ID NO: 1 (AAAAAAASGSGGYG-PENQGPSGPVAYGPGGPVSSAAAAAAAGSGPG-GYGPENQ GPSGPGGYGPGGSGS-SAAAAAAAAASGPGGYGPGSQGPSGPGGSGGYG PGSQGPSG PGASSAAAAAAAAASGPG-GYGPGSQGPSGPGAYGPGGPGSSAAASGPG-GYGPGSQ GPSGPGGSGGYGPGSQGPSGPGGP-GASAAAAAAAAAASGPGGYGPGSQGPSGPGA YGPGGPGSSAAASGPGGYGPGSQGPSGP-GAYGPGGPGSSAAAAAAAGSGPGGYG PGNQGPSGPGGYGPGGPGSSAAAAAAASGPG-GYGPGSQGPSGPGVYGPGGPGSSA AAAAAAGSGPGGYGPGNQGPSGPG-GYGPGGSGSSAAAAAAAAASGPGGYGPGSQ GPSGPGGSGGYGPGSQGPSGPGAS-SAAAAAAAAASGPGGYGPGSQGPSGPGAYGPG GPGSSAAASGPGGYGPGSQGPSGP-GAYGPGGPGSSAAAAAAAASGPGGYGPGSQGP SGPGGSRGYGPGSQGPGGP-GASAAAAAAAAASGPG-GYGPGSQGPSGPGYQGPSG PGAYGPSPSASAS).

2. The composition of claim 1, wherein at least one of: said particles are porous particles and are characterized by BET surface area of at least 10 m²/g; and said MaSp-based polymer is characterized by a DSC pattern exhibiting at least an endothermic peak in the range of from 200° C. to 280° C.

3. The composition of claim 1, further comprising an additional compound in contact with said MaSp-based polymer, and wherein said additional compound is selected from a biologically active agent, cosmetically active ingredient and a nutraceutical.

4. The composition of claim 3, wherein a weight per weight (w/w) ratio of said MaSp-based polymer to said additional compound is between 10:1 and 1:10.

5. The composition of claim 1, wherein each of said repeats comprises the amino acid sequence as set forth in any one of: SEQ ID NO: 2 (SGPGGYGPGSQGPSGPG-GYGPGGPGSS) and SEQ ID NO: 3 (AAAAAAAASGPG-GYGPGSQGPSGPGGYGPGGPGSS) or a variant having at least 90% sequence identity thereto.

6. The composition of claim 1, wherein said repetitive region comprises 10-20 repeats of SEQ ID NO: 3; and wherein said MaSp-based polymer is a water insoluble polymer.

7. The composition of claim 1, wherein said single N-terminal region consists of: SEQ ID NO: 4 (MSYYHHHHHHDYDIPTTENLYFQGAMDPE-FKGLRRRAQLV); and wherein said single C-terminal region consists of: SEQ ID NO: 7 (VAASRLSSPAASSRVS-SAVSSLVSSGPTNGAAVSGALNSLVSQ-ISASNPGLSGCD ALVQALLELVSALVAILSSAS-IGQVNVSSVSQSTQMISQALS).

8. The composition of claim 1, obtained by expression of MaSp in a bacterium.

9. A composition comprising the MaSp-based polymer of claim 1 non-covalently bound to an additional polymer, wherein a w/w ratio of said MaSp-based polymer to said additional polymer is between 1:1 and 1:100.

10. The composition of claim 9, wherein a w/w concentration of said additional polymer is 50% to 95% (w/w) of the total composition.

11. The composition of claim 9, wherein said additional polymer is selected from a synthetic polymer, a thermoplastic polymer, a thermoset, a film forming agent, an epoxy, a polyester a polyamide, a polyol, a polyurethane, polyethylene, a silicon, liquid crystal polymers, maleic anhydride grafted polypropylene, a polyacrylate, a polycarbonate, polyamides, Nylon 4,6, Nylon 6, Nylon 6,6, Nylon 11, Nylon 12, poly(arylamide), polyethylene, polybutylene terephthalate, polyethylene terephthalate, polyphenylene sulfide, polyphthalamide, polypropylene, poly(vinylidene fluoride), Poly(2-hydroxyethyl methacrylate) (pHEMA), polyurethane, polyvinyl butyral, ethylene vinyl alcohol copolymer, polylactide acid (PLA) or a copolymer thereof, polycaprolactone (PCL), xanthan, cellulose, collagen, elastin, keratin, cotton, rubber, cellulose, wool, and any combination thereof.

12. The composition of claim 10, wherein a w/w ratio between said film forming agent and said MaSp based fiber is from 5:1 to 50:1.

13. The composition of claim 9, characterized by at least one improved mechanical property as compared to the property for the additional polymer free of said MaSp-based polymer, wherein said property is selected from the group consisting of: Young's modulus, storage modulus, loss modulus, tensile strength, fracture strain, yield point, toughness, work to failure, impact strength, tear strength, flexural modulus, flexural strain and stress at a specific percentage elongation, and abrasion.

14. An article comprising the composition of claim 1, being in a form of film, a suture, surgical mesh, medical adhesive strips, electrospun mesh, skin grafts, fat grafts, cosmetics, dermal fillers, drug eluting/delivery device, replacement ligaments, clothing fabric, bullet-proof vest lining, cable, tube, film, rope, fishing line, tires, sports equipment, and reinforced plastics.

15. A recombinant bacterium having the ability to express a MaSp-based polymer comprising the amino acid sequence as set forth in SEQ ID NO: 2 (SGPGGYGPGSQGPSGPG-GYGPGGPGSS).

16. A process, comprising:
(i) providing the recombinant bacterium of claim 15;
(ii) providing conditions for expression of the MaSp by the bacterium;
(iii) isolating the expressed proteins, and optionally,
(iv) drying of said synthetic dragline spider silk
thereby fabricating the synthetic dragline spider silk.

17. The process of claim 16, wherein said step (ii) comprises one or more of: (a) providing a solution with a pH in the range of 5 to 6.5; (b) providing an expression inducer; (c) waiting during a period of time to obtain an insoluble polymer.

18. The process of claim 16, further comprising an enrichment step with an additional polymer comprises mixing a solution of said synthetic dragline spider silk, with solution of said additional polymer.

\* \* \* \* \*